US008759064B2

(12) United States Patent
Mitchell et al.

(10) Patent No.: US 8,759,064 B2

(45) Date of Patent: Jun. 24, 2014

(54) CELLOBIOHYDROLASE VARIANTS

(75) Inventors: Vesna Mitchell, San Jose, CA (US); Grzegorz Wojciechowski, Livermore, CA (US); Oscar Alvizo, Fremont, CA (US)

(73) Assignee: Codexis, Inc., Redwood City, CA (US)

( * ) Notice: Subject to any disclaimer, the term of this patent is extended or adjusted under 35 U.S.C. 154(b) by 64 days.

(21) Appl. No.: 13/107,849

(22) Filed: May 13, 2011

(65) Prior Publication Data

US 2012/0003703 A1 Jan. 5, 2012

Related U.S. Application Data

(60) Provisional application No. 61/345,023, filed on May 14, 2010.

(51) Int. Cl.
*C12N 9/42* (2006.01)
*C13K 1/02* (2006.01)

(52) U.S. Cl.
USPC .......................................... 435/209; 426/49

(58) Field of Classification Search
None
See application file for complete search history.

(56) References Cited

U.S. PATENT DOCUMENTS 6,117,679 A 9/2000 Stemmer
6,376,246 B1 4/2002 Crameri et al.
6,586,182 B1 7/2003 Patten et al.
7,783,428 B2 8/2010 Gustafsson et al.
7,923,236 B2 4/2011 Gusakov et al.
2004/0197890 A1 10/2004 Lange et al.
2007/0238155 A1 10/2007 Gusakov et al.
2008/0220990 A1 9/2008 Fox
2009/0280105 A1 11/2009 Gusakov et al.
2009/0311755 A1 12/2009 Harris et al.
2009/0312196 A1 12/2009 Colbeck et al.
2010/0267089 A1 10/2010 Yang et al.

FOREIGN PATENT DOCUMENTS

WO 03/000941 A2 1/2003
WO 2006/074005 A2 7/2006
WO 2008/025164 A1 3/2008
WO 2008/095033 A2 8/2008
WO 2008/153903 A2 12/2008
WO 2008/153925 A2 12/2008
WO 2010/066411 A2 6/2010
WO 2010/118058 A2 10/2010
WO 2010/120557 A1 10/2010
WO 2010/141325 A1 12/2010
WO 2010/141779 A1 12/2010
WO 2011/050037 A1 4/2011

(Continued)

OTHER PUBLICATIONS

Federova, N. D., et al., 2008, "Genomic islands in the pathogenic filamentous fungus *Aspergillus fumigatis*", PLoS Genetics, vol. 4, No. 4, entry e1000046.*

(Continued)

*Primary Examiner* — Manjunath Rao
*Assistant Examiner* — William W Moore
(74) *Attorney, Agent, or Firm* — Kilpatrick Townsend & Stockton LLP

(57) ABSTRACT

The invention relates to recombinant expression of variant forms of C1 CBH1a and homologs thereof, having improved thermostability, low-pH tolerance, specific activity and other desirable properties. Also provided are methods for producing ethanol and other valuable organic compounds by combining cellobiohydrolase variants with cellulosic materials.

16 Claims, 6 Drawing Sheets

(56) References Cited

FOREIGN PATENT DOCUMENTS

| | | | |
|---|---|---|---|
| WO | 2011/080317 | A2 | 7/2011 |
| WO | 2011/098580 | A1 | 8/2011 |
| WO | 2012/044915 | A2 | 4/2012 |

OTHER PUBLICATIONS

Gusakov, A. V., et al., 2005, "Purification, cloning and characterization of two forms of thermostable and highly active cellobiohydrolase I (Cel7A) produced by the industrial strain of *Chrysosporium lucknowense*", Enzyme and Microbial Technology, vol. 36, No. 1, pp. 57-69.*

Gusakov, A. V., et al., 2007, "Design of highly efficient cellulose mixtures for enzymatic hydrolysis of cellulose", Biotechnology and Bioengineering, vol. 97, No. 5, pp. 1028-1038.*

Fox, R., "Directed molecular evolution by machine learning and the influence of nonlinear interactions," J. Theor. Bioi., 234(2):187-199, 2005.

Fox, R., et al., "Optimizing the search algorithm for protein engineering by directed evolution," Protein Eng., 16 (8):589-597, 2003.

International Search Report and Written Opinion, date of mailing Oct. 31, 2011, PCT application No. PCT/US11/36544, 7 page.

* cited by examiner

Alignment of *H. grisea* var. thermoidea cellobiohydrolase (H.g.) (SEQ ID NO:39) and C1 CBH1a (C1) (SEQ ID NO:41)

```
H.g.    4    AKFATLAALVASAAAQQACSLTTERHPSLSWKKCTAGGQCQTVQASITLDSNWRWTHQVS   63
             AKFATLAALVA AAAQ AC+LT E HPSL+W KCT+GG C +VQ SIT+D+NWRWTH+
C1      3    AKFATLAALVAGAAAQNACTLTAENHPSLTWSKCTSGGSCTSVQGSITIDANWRWTHRTD   62

H. g.   64   GSTNCYTGNKWDTSICTDAKSCAQNCCVDGADYTSTYGITTNGDSLSLKFVTKGQYSTNV   123
              +TNCY GNKWDTS C+D  SCA  CC+DGADY+STYGITT+G+SL+LKFVTKGQYSTN+
C1      63   SATNCYEGNKWDTSYCSDGPSCASKCCIDGADYSSTYGITTSGNSLNLKFVTKGQYSTNI   122

H. g.   124  GSRTYLMDGEDKYQTFELLGNEFTFDVDVSNIGCGLNGALYFVSMDADGGLSRYPGNKAG   183
             GSRTYLM+ + KYQ F+LLGNEFTFDVDVSN+GCGLNGALYFVSMDADGG+S+Y GNKAG
C1      123  GSRTYLMESDTKYQMFQLLGNEFTFDVDVSNLGCGLNGALYFVSMDADGGMSKYSGNKAG   182

H. g.   184  AKYGTGYCDAQCPRDIKFINGEANIEGWTGSTNDPNAGAGRYGTCCSEMDIWEANNMATA   243
             AKYGTGYCD+QCPRD+KFINGEAN+E W  STND NAG G+YG+CCSEMD+WEANNMA A
C1      183  AKYGTGYCDSQCPRDLKFINGEANVENWQSSTNDANAGTGKYGSCCSEMDVWEANNMAAA   242

H. g.   244  FTPHPCTIIGQSRCEGDSCGGTYSNERYAGVCDPDGCDFNSYRQGNKTFYGKGMTVDTTK   303
             FTPHPCT+IGQSRCEGDSCGGTYS +RYAG+CDPDGCDFNSYRQGNKTFYGKGMTVDTTK
C1      243  FTPHPCTVIGQSRCEGDSCGGTYSTDRYAGICDPDGCDFNSYRQGNKTFYGKGMTVDTTK   302

H. g.   304  KITVVTQFLKDANGDLGEIKRFYVQDGKIIPNSESTIPGVEGNSITQDWCDRQKVAFGDI   363
             KITVVTQFLK++ G+L EIKRFYVQ+GK+IPNSESTIPGVEGNSITQDWCDRQK AFGD+
C1      303  KITVVTQFLKNSAGELSEIKRFYVQNGKVIPNSESTIPGVEGNSITQDWCDRQKAAFGDV   362

H. g.   364  DDFNRKGGMKQMGKALAGPMVLVMSIWDDHASNMLWLDSTFPVDAAGKPGAERGACPTTS   423
              DF  KGGM QMGKALAGPMVLVMSIWDDHA NMLWLDST+P+D AGKPGAERGACPTTS
C1      363  TDFQDKGGMVQMGKALAGPMVLVMSIWDDHAVNMLWLDSTWPIDGAGKPGAERGACPTTS   422

H. g.   424  GVPAEVEAEAPNSNVVFSNIRFGPIGSTVAGLPGAGNGGNNGGNPPPPTTTTSSAPATTT   483
             GVPAEVEAEAPNSNV+FSNIRFGPIGSTV+GLP  G+G  N           +SS  ++ +
C1      423  GVPAEVEAEAPNSNVIFSNIRFGPIGSTVSGLPDGGSGNPNPPVSSSTPVPSSSTTSSGS   482

H. g.   484  TASAGPK--AGRWQQCGGIGFTGPTQCEEPYTCTKLNDWYSQCL   525
             +   G    A  ++QCGGIGFTGPTQCE PYTCTKLNDWYSQCL
C1      483  SGPTGGTGVAKHYEQCGGIGFTGPTQCESPYTCTKLNDWYSQCL   526
```

*FIG. 6*

CELLOBIOHYDROLASE VARIANTS

CROSS-REFERENCES TO RELATED APPLICATIONS

This application claims benefit of U.S. provisional application No. 61/345,023, filed May 14, 2010, the entire content of which is incorporated herein by reference.

FIELD OF THE INVENTION

The invention relates to expression of recombinant cellobiohydrolase variants and their use in the production of fermentable sugars from cellulosic biomass.

BACKGROUND OF THE INVENTION

Cellulosic biomass is a significant renewable resource for the generation of fermentable sugars. These sugars can be used as reactants in various metabolic processes, including fermentation, to produce biofuels, chemical compounds, and other commercially valuable end-products. While the fermentation of simple sugars such as glucose to ethanol is relatively straightforward, the efficient conversion of cellulosic biomass to fermentable sugars is challenging. See, e.g., Ladisch et al., 1983, *Enzyme Microb. Technol.* 5:82. Cellulose may be pretreated chemically, mechanically, enzymatically or in other ways to increase the susceptibility of cellulose to hydrolysis. Such pretreatment may be followed by the enzymatic conversion of cellulose to cellobiose, cello-oligosaccharides, glucose, and other sugars and sugar polymers, using enzymes that break down the β-1-4 glycosidic bonds of cellulose. These enzymes are collectively referred to as "cellulases."

Cellulases are divided into three sub-categories of enzymes: 1,4-β-D-glucan glucanohydrolase ("endoglucanase" or "EG"); 1,4-β-D-glucan cellobiohydrolase ("exoglucanase", "cellobiohydrolase", or "CBH"); and β-D-glucoside-glucohydrolase ("β-glucosidase", "cellobiase" or "BGL"). Endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetrose. There are two main types of cellobiohydrolases: Type 1 cellobiohydrolases are members of the Glycoside Hydrolase Family 7, and cleave processively from the reducing end of cellulose chains. Type 2 cellobiohydrolases cleave processively from the non-reducing end of cellulose. β-glucosidases split cellobiose into glucose monomers.

Cellulases with improved properties for use in processing cellulosic biomass would reduce costs and increase the efficiency of production of biofuels and other commercially valuable compounds.

BRIEF SUMMARY OF THE INVENTION

In one aspect, the present invention provides recombinant cellobiohydrolase variants that exhibit improved properties. In some embodiments, the cellobiohydrolase variants are superior to naturally occurring cellobiohydrolases under conditions required for saccharification of cellulosic biomass.

In some embodiments, a recombinant cellobiohydrolase variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 and comprises an amino acid substitution at one or more positions selected from 2, 4, 22, 24, 30, 32, 39, 48, 49, 58, 64, 66, 69, 79, 82, 90, 98, 102, 116, 117, 118, 122, 126, 155, 177, 192, 205, 209, 212, 218, 221, 240, 241, 242, 264, 265, 267, 273, 286, 294, 343, 381, 394, 401, 402, 403, 405, 417, 432, 448, 452, 475, 483, 486, 490, 492, 502, 508, 512, and 526, wherein the position is numbered with reference to a wild-type C1 CBH1a pre-protein (e.g., SEQ ID NO:4). In some embodiments, the variant comprises one or more amino acid substitutions selected from X2H, X4Q, X22H, X24F/I/K/L/N/R/V, X30P, X32M, X39R, X48W, X49V, X58I/N, X64S/T, X66C/P, X69C/D/N/T, X79P, X82K/M, X90L/V, X98L, X102H, X116T, X117N, X118G/H, X122V, X126V, X155P, X177P, X192A, X205C/G, X209G, X212P, X218H, X221H/Q/W, X240S, X241T, X242V, X264L, X265W, X267K, X273P, X286M, X294P, X343P, X381G, X394A/D/G/L/Q/S, X401D, X402G, X403F/Y, X405V, X417P, X432F, X448D, X452E, X475G, X483D/K/L, X486I/V/Y, X490F/M, X492V, X502R, X508H/S, X512G, and X526A. In some embodiments, a recombinant cellobiohydrolase variant is encoded by a polynucleotide that hybridizes at high stringency to the complement of SEQ ID NO:1 and comprises one or more amino acid substitutions as described herein.

In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 and comprises an amino acid substitution at one or more positions selected from Y2, K4, T22, T24, S30, T32, G39, S48, I49, T58, A64, N66, E69, S79, P82, I90, T98, T102, G116, Q117, Y118, I122, T126, G155, S177, S192, A205, N209, S212, N218, T221, A240, A241, A242, T264, Y265, T267, I273, Q286, K294, E343, P381, V394, S401, T402, W403, I405, A417, A432, G448, S452, S475, S483, T486, G490, A492, G502, Q508, P512, and L526, wherein the position is numbered with reference to a wild-type C1 CBH1a pre-protein (e.g., SEQ ID NO:4). In some embodiments, the variant comprises one or more amino acid substitutions selected from Y2H, K4Q, T22H, T24F/I/K/L/N/R/V, S30P, T32M, G39R, S48W, I49V, T58I/V, A64S/T, N66C/P, E69C/D/N/T, S79P, P82K/M, I90L/V, T98L, T102H, G116T, Q117N, Y118G/H, I122V, T126V, G155P, S177P, S192A, A205C/G, N209G, S212P, N218H, T221H/Q/W, A240S, A241T, A242V, T264L, Y265W, T267K, I273P, Q286M, K294P, E343P, P381G, V394A/D/G/L/Q/S, S401D, T402G, W403F/Y, I405V, A417P, A432F, G448D, S452E, S475G, S483D/K/L, T486I/V/Y, G490F/M, A492V, G502R, Q508H/S, P512G, and L526A. In some embodiments, a recombinant cellobiohydrolase variant is encoded by a polynucleotide that hybridizes at high stringency to the complement of SEQ ID NO:1 and comprises one or more amino acid substitutions as described herein.

In some embodiments, the variant comprises at least about 90%, at least about 91%, at least about 92%, at least about 93%, at least about 94%, at least about 95%, at least about 96%, at least about 97%, at least about 98%, or at least about 99% identity to SEQ ID NO:2 and comprises mutations at positions 155 and 212, wherein the positions are numbered with reference to a wild-type C1 CBH1a pre-protein (e.g., SEQ ID NO:4). In some embodiments, the amino acid residue at position 155 is glycine (G155) and the amino acid residue at position 212 is serine (S212). In some embodiments, the amino acid residue at G155 is replaced with proline (G155P) and the amino acid residue at S212 is replaced with proline (S212P). In some embodiments, the variant further comprises a mutation at position 294, wherein the position is numbered with reference to a wild-type C1 CBH1a pre-protein (e.g., SEQ ID NO:4). In some embodiments, the amino acid residue at position 294 is lysine (K294). In some embodiments, the amino acid residue at K294 is replaced with proline (K294P). In some embodiments, the variant further comprises mutations at one or more of positions 79 and 343, wherein the position is numbered with reference to a wild-type C1 CBH1a pre-protein (e.g., SEQ ID NO:4). In some embodiments, the amino acid residue at position 79 is serine (S79) and the amino acid residue at position 343 is glutamic acid (E343). In some embodiments, the amino acid residue at S79 is replaced with proline (S79P) and the amino acid residue at E343 is replaced with proline (E343P). In some embodiments, the variant comprises a combination of amino acid substitutions selected from:

(i) S79P; G155P; S177P; S212P; K294P; E343P;
(ii) S79P; Q117N; G155P; S177P; S212P; K294P; E343P; P381G; A417P;
(iii) S30P; T58I; S79P; P82M; Q117N; G155P; S177Q; S212P; K294P; E343P; P381G; A417P;
(iv) S30P; T58I; S79P; P82M; I90V; Q117N; G155P; S177P; N209G; S212P; T221W; Q286M; K294P; E343P; P381G; A417P;
(v) S30P; T58I; S79P; P82M; I90V; Q117N; G155P; S177P; N209G; S212P; T221W; Q286M; K294P; E343P; P381G; S401D; A417P; and
(vi) S30P; T58I; S79P; I90L; Q117N; G155P; S177P; N209G; S212P; T221W; Q286M; K294P; E343P; P381G; V394A; S401D; A417P.

In some embodiments, the variant comprises one or more amino acid substitutions selected from S79P, G155P, S212P, K294P, and E343P. In some embodiments, the variant comprises one or more amino acid substitutions selected from K4Q, N209G, S212P, A240S, A241T, and K294P. In some embodiments, the variant comprises one or more amino acid substitutions selected from T24F/I/K/N/R/V, S48W, E69C, T126V, N209G, and I273P. In some embodiments, the variant comprises one or more amino acid substitutions selected from T58I, Q117N, T221H, P381G, and A417P. In some embodiments, the variant comprises one or more amino acid substitutions selected from Y118H, T267K, I273P, T402G, A432F, and G448D. In some embodiments, the variant comprises one or more amino acid substitutions selected from, T24L, T58L, I90V, G116T, I122V, T221W, H392P, and G502R. In some embodiments, the variant comprises one or more amino acid substitutions selected from T24I/K/L/N/V, E69C, I90V, G116T, N209G, Q286M, and G502R. In some embodiments, the variant comprises one or more amino acid substitutions selected from T24I/K, E69C, G116T, Y118H, A205C/G, V394L, A492V, G502R, and Q508H. In some embodiments, the variant comprises one or more amino acid substitutions selected from T24F/I/V, N66C, G116T, N218H, and A242V.

In some embodiments, the variant comprises an amino acid substitution at one or more positions selected from S79, G155, S177, S212, K294, and E343. In some embodiments, the variant comprises one or more amino acid substitutions selected from S79P, G155P, S177P, S212P, K294P, and E343P. In some embodiments, the variant comprises the amino acid substitutions S79P, G155P, S177P, S212P, K294P, and E343P. In some embodiments, the variant has the amino acid sequence of SEQ ID NO:28.

In some embodiments, the variant comprises an amino acid substitution at one or more positions selected from S30, T58, S79, P82, Q117, G155, S177, S212, K294, E343, P381, and A417. In some embodiments, the variant comprises one or more amino acid substitutions selected from S30P, T58I, S79P, P82M, Q117N, G155P, S177Q, S212P, K294P, E343P, P381G, and A417P. In some embodiments, the variant comprises the amino acid substitutions S30P, T58I, S79P, P82M, Q117N, G155P, S177Q, S212P, K294P, E343P, P381G, and A417P. In some embodiments, the variant has the amino acid sequence of SEQ ID NO:32.

In some embodiments, the variant comprises an amino acid substitution at one or more positions selected from S30, T58, S79, P82, I90, Q117, G155, S177, N209, S212, T221, Q286, K294, E343, P381, and A417. In some embodiments, the variant comprises one or more amino acid substitutions selected from S30P, T58I, S79P, P82M, I90V, Q117N, G155P, S177P, N209G, S212P, T221W, Q286M, K294P, E343P, P381G, and A417P. In some embodiments, the variant comprises the amino acid substitutions S30P, T58I, S79P, P82M, I90V, Q117N, G155P, S177P, N209G, S212P, T221W, Q286M, K294P, E343P, P381G, and A417P. In some embodiments, the variant has the amino acid sequence of SEQ ID NO:34.

In some embodiments, the variant comprises an amino acid substitution at one or more positions selected from S30, T58, S79, P82, I90, Q117, G155, S177, N209, S212, T221, Q286, K294, E343, P381, S401, and A417. In some embodiments, the variant comprises one or more amino acid substitutions selected from S30P, T58I, S79P, P82M, I90V, Q117N, G155P, S177P, N209G, S212P, T221W, Q286M, K294P, E343P, P381G, S401D, and A417P. In some embodiments, the variant comprises the amino acid substitutions S30P, T58I, S79P, P82M, I90V, Q117N, G155P, S177P, N209G, S212P, T221W, Q286M, K294P, E343P, P381G, S401D, and A417P. In some embodiments, the variant has the amino acid sequence of SEQ ID NO:36.

In some embodiments, the variant comprises an amino acid substitution at one or more positions selected from S30, T58, S79, I90, Q117, G155, S177, N209, S212, T221, Q286, K294, E343, P381, V394, S401, and A417. In some embodiments, the variant comprises one or more amino acid substitutions selected from S30P, T58I, S79P, I90L, Q117N, G155P, S177P, N209G, S212P, T221W, Q286M, K294P, E343P, P381G, V394A, S401D, and A417P. In some embodiments, the variant comprises the amino acid substitutions S30P, T58I, S79P, I90L, Q117N, G155P, S177P, N209G, S212P, T221W, Q286M, K294P, E343P, P381G, V394A, S401D, and A417P. In some embodiments, the variant has the amino acid sequence of SEQ ID NO:38.

In some embodiments, the variant comprises a C-terminal deletion of 1-35 residues. In some embodiments, the variant comprises one or more substitutions in the cellulose binding module (CBM) that:

(a) prevents the CBM from binding cellulose;
(b) replaces a residue corresponding to W521 and/or Y522 in a wild-type C1 CBH1a pre-protein (e.g., SEQ ID NO:4) with a non-aromatic residue; or
(c) prevents formation of (i) a disulfide bond between the residues corresponding to C498 and C509 in the wild-type C1 CBH1a pre-protein (e.g., SEQ ID NO:4); (ii) a disulfide bond between the residues corresponding to C515 and C525 in the wild-type C1 CBH1a pre-protein (e.g., SEQ ID NO:4); or (iii) both (i) and (ii).

In some embodiments, the variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:2 and comprises a pair of amino acid substitutions selected from A205C and V207C, and C78V and A205C, wherein the position is numbered with reference to a wild-type C1 CBH1a pre-protein (e.g., SEQ ID NO:4). In some embodiments, the variant comprises the amino acid substitutions A205C and V207C. In some embodiments, the variant comprises the amino acid substitutions C78V and A205C. In some embodiments, the variant is encoded by a polynucleotide that hybridizes at high stringency to the complement of SEQ ID NO:1 and comprises one or more amino acid substitutions as described herein.

In some embodiments, a recombinant cellobiohydrolase variant as described herein has increased thermostability and/or thermoactivity in comparison to secreted wild-type C1 CBH1a (SEQ ID NO:2). In some embodiments, the variant exhibits at least a 1-fold, at least a 2-fold, at least a 3-fold, at least a 4-fold, at least a 5-fold, at least a 6-fold, at least a 7-fold, at least an 8-fold or higher increase in thermostability relative to secreted wild-type C1 CBH1a (SEQ ID NO:2). In some embodiments, the variant has increased thermostability after incubation at pH 4.4 and 66° C. for 2 hours in comparison to secreted wild-type C1 CBH1a (SEQ ID NO:2).

In some embodiments, a recombinant cellobiohydrolase variant as described herein comprises at least about 90%, at least about 91%, at least about 92%, at least about 93%, at least about 94%, at least about 95%, at least about 96%, at least about 97%, at least about 98%, or at least about 99% identity to a cellobiohydrolase type 1 from C1 (SEQ ID NO:2), *Thielavia australiensis* (SEQ ID NO:5), *Humicola grisea* (SEQ ID NO:6), *Chaetomium thermophilum* (SEQ ID NO:7), *Sordaria macrospora* (SEQ ID NO:8), *Chaetomidium pingtungium* (SEQ ID NO:9), *Botryosphaeria rhodina* (SEQ ID NO:10), *Trichophaea saccata* (SEQ ID NO:11), *Aspergillus nidulans* (SEQ ID NO:12), *Schizophyllum commune* (SEQ ID NO:13), or *Agaricus bisporus* (SEQ ID NO:14).

In another aspect, the present invention provides polynucleotides encoding cellobiohydrolase variants that exhibit improved properties. In some embodiments, the polynucleotide encodes an amino acid sequence that comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:2 and comprises an amino acid substitution at one or more positions selected from 2, 4, 22, 24, 30, 32, 39, 48, 49, 58, 64, 66, 69, 79, 82, 90, 98, 102, 116, 117, 118, 122, 126, 155, 177, 192, 205, 209, 212, 218, 221, 240, 241, 242, 264, 265, 267, 273, 286, 294, 343, 381, 394, 401, 402, 403, 405, 417, 432, 448, 452, 475, 483, 486, 490, 492, 502, 508, 512, and 526, wherein the position is numbered with reference to a wild-type C1 CBH1a pre-protein (e.g., SEQ ID NO:4). In some embodiments, the polynucleotide encodes an amino acid sequence that comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:2 and comprises an amino acid substitution at one or more positions selected from Y2, K4, T22, T24, S30, T32, G39, S48, I49, T58, A64, N66, E69, S79, P82, I90, T98, T102, G116, Q117, Y118, I122, T126, G155, S177, S192, A205, N209, S212, N218, T221, A240, A241, A242, T264, Y265, T267, I273, Q286, K294, E343, P381, V394, S401, T402, W403, I405, A417, A432, G448, S452, S475, S483, T486, G490, A492, G502, Q508, P512, and L526, wherein the position is numbered with reference to SEQ ID NO:4. In some embodiments, the polynucleotide encodes an amino acid sequence that comprises one or more amino acid substitutions selected from Y2H, K4Q, T22H, T24F/I/K/L/N/R/V, S30P, T32M, G39R, S48W, I49V, T58I/V, A64S/T, N66C/P, E69C/D/N/T, S79P, P82K/M, I90L/V, T98L, T102H, G116T, Q117N, Y118G/H, I122V, T126V, G155P, S177P, S192A, A205C/G, N209G, S212P, N218H, T221H/Q/W, A240S, A241T, A242V, T264L, Y265W, T267K, I273P, Q286M, K294P, E343P, P381G, V394A/D/G/L/Q/S, S401D, T402G, W403F/Y, I405V, A417P, A432F, G448D, S452E, S475G, S483D/K/L, T486I/V/Y, G490F/M, A492V, G502R, Q508H/S, P512G, and L526A. In some embodiments, the polynucleotide hybridizes at high stringency to the complement of SEQ ID NO:1 and encodes a cellobiohydrolase variant comprising one or more amino acid substitutions as described herein.

In still another aspect, the present invention provides expression vectors comprising a polynucleotide encoding a cellobiohydrolase variant as described herein.

In yet another aspect, the present invention provides host cells transformed with a polynucleotide or vector encoding a cellobiohydrolase variant as described herein. In some embodiments, the host cell expresses a non-naturally occurring cellobiohydrolase having the amino acid sequence of a cellobiohydrolase variant as described herein. In some embodiments, the host cell is a yeast or filamentous fungus.

In another aspect, the present invention provides enzyme compositions comprising a recombinant cellobiohydrolase variant as described herein. In some embodiments, the enzyme composition is used in a composition for a saccharification application. In some embodiments, the enzyme composition comprising a cellobiohydrolase variant of the present invention will comprise other enzymes (e.g., one or more other cellulases).

In still another aspect, the present invention provides methods of producing a cellobiohydrolase variant comprising culturing a host cell transformed with a polynucleotide or vector encoding a cellobiohydrolase variant as described herein under conditions sufficient for the production of the cellobiohydrolase variant by the cell. In some embodiments, the cellobiohydrolase variant polypeptide is secreted by the cell and obtained from the cell culture medium.

In yet another aspect, the present invention provides methods of producing a fermentable sugar, comprising contacting a cellulosic biomass with a β-glucosidase (Bgl), an endoglucanase (EG) such as a type 2 endoglucanase (EG2), a type 2 cellobiohydrolase (CBH2) such as a type 2b cellobiohydrolase (CBH2b), a glycoside hydrolase 61 protein (GH61), and a CBH1a variant as described herein under conditions in which the fermentable sugar is produced.

In yet another aspect, the present invention provides methods of producing an end-product from a cellulosic substrate, comprising (a) contacting the cellulosic substrate with a β-glucosidase (Bgl), an endoglucanase (EG) such as a type 2 endoglucanase (EG2), a type 2 cellobiohydrolase (CBH2) such as a type 2b cellobiohydrolase (CBH2b), a glycoside hydrolase 61 protein (GH61), and a CBH1a variant as described herein under conditions in which fermentable sugars are produced; and (b) contacting the fermentable sugars with a microorganism in a fermentation to produce the end-product. In some embodiments, prior to step (a), the cellulosic substrate is pretreated to increase its susceptibility to hydrolysis. In some embodiments, the end-product is an alcohol, an amino acid, an organic acid, a diol, or glycerol. In some embodiments, the end-product is an alcohol (e.g., ethanol or butanol). In some embodiments, the microorganism is a yeast. In some embodiments, the process comprises a simultaneous saccharification and fermentation process. In some embodiments, the saccharification and fermentation steps are consecutive. In some embodiments, the enzyme production is simultaneous with saccharification and fermentation.

BRIEF DESCRIPTION OF THE DRAWINGS

FIG. 6 shows an alignment between C1 CBH1a (SEQ ID NO:41) and a *Humicola grisea* cellobiohydrolase (SEQ ID NO:39). The consensus sequence is SEQ ID NO:40.

DEFINITIONS

Figure 1:
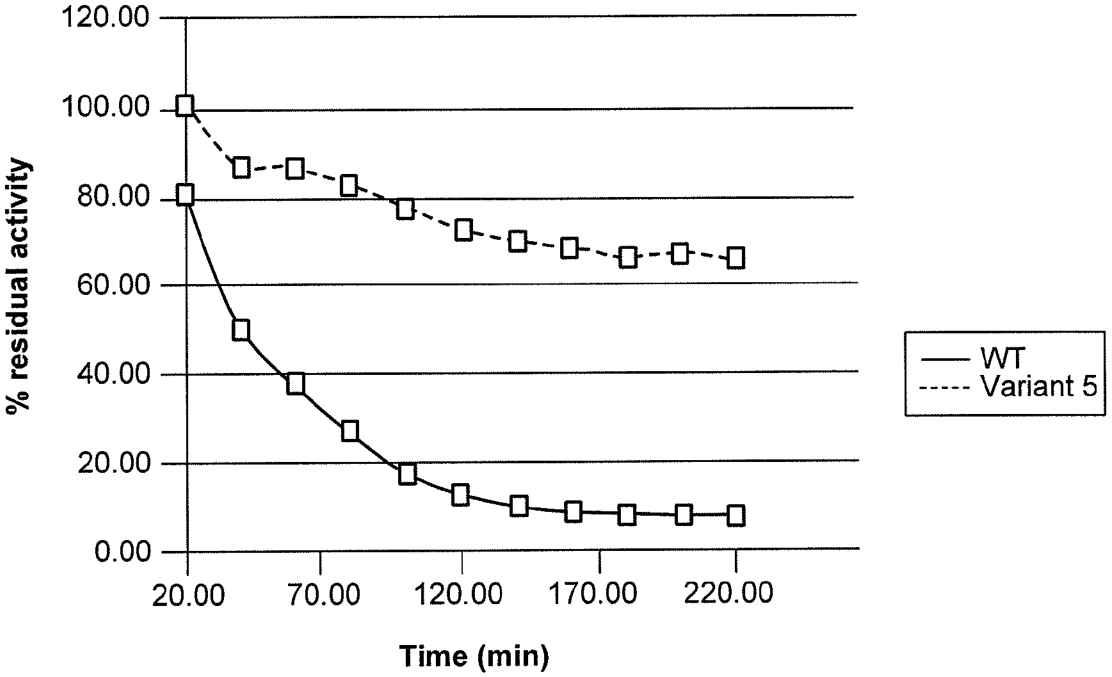
FIG. 1 shows the residual activity and half-life of C1 CBH1a Variant 5 as compared to wild-type C1 CBH1a. The plot depicts a decrease in activity after incubation at pH 4.4 and 63° C. as determined by a 4-methylumbelliferyl β-D-lactopyranoside (MUL) assay at pH 4.4, 62° C. for 1 hour as described in Example 4. Half-life was calculated based on the decay in residual activity after incubation at the indicated pH and temperature.
Figure 2:
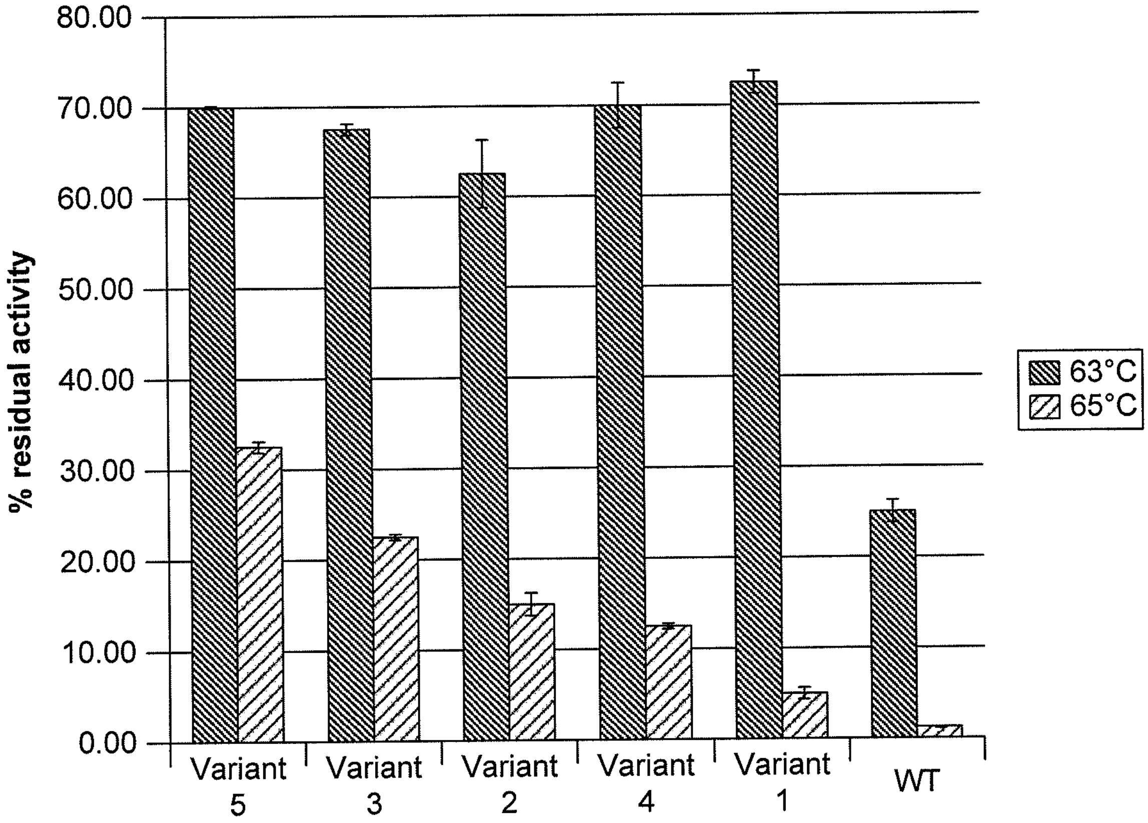
FIG. 2 shows the residual activity of wild-type C1 CBH1a and C1 CBH1a variants 1, 2, 3, 4, and 5 produced in yeast shake flask, after 2 hour pre-incubation at pH 4.4 and 63 or 65° C., as determined by a MUL assay at pH 4.4, 62° C. for 2 hours as described in Example 4. n=3, error bars represent ±1 std dev.
Figure 3:
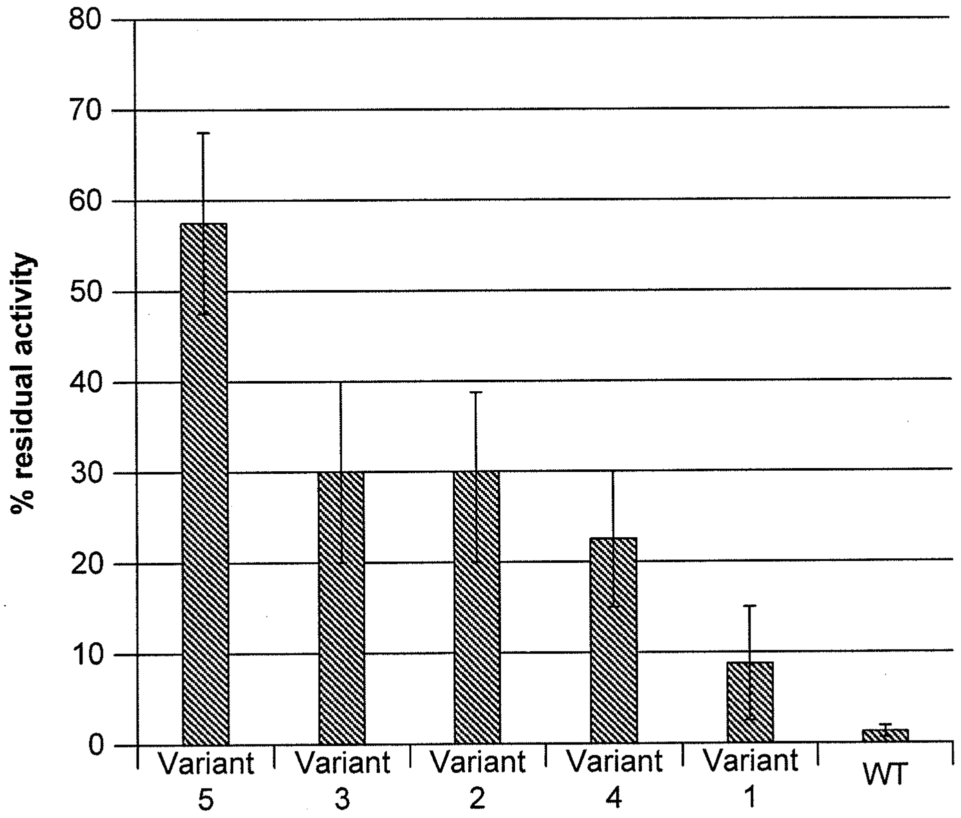
FIG. 3 shows the residual activity of wild-type C1 CBH1a and C1 CBH1a variants 1, 2, 3, 4, and 5 produced in C1, after 2 hour pre-incubation at pH 4.4 and 63° C., as determined by a MUL assay at pH 5, 50° C. for 10 minutes as described in Example 4. n=36, error bars represent ±1 std dev.
Figure 4:
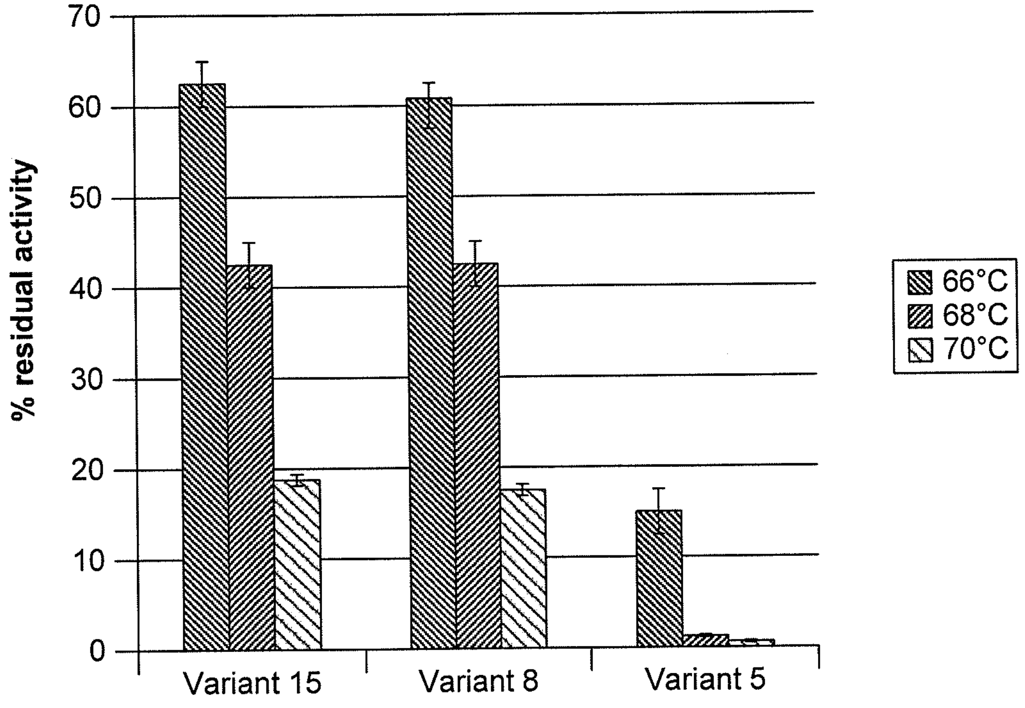
FIG. 4 shows the residual activity of an improved C1 CBH1a variant from a wobble library, after 2 hour pre-incubation at pH 4.4, 68-70° C., as determined by a MUL assay at pH 4.4, 62° C. for 2 hours as described in Example 5. n=3, error bars represent ±1SD.

Unless defined otherwise, all technical and scientific terms used herein generally have the same meaning as commonly understood by one of ordinary skill in the art to which this invention belongs. Generally, the nomenclature used herein and the laboratory procedures in analytical chemistry, cell culture, molecular genetics, organic chemistry and nucleic acid chemistry and hybridization described below are those well known and commonly employed in the art. As used herein, "a," "an," and "the" include plural references unless the context clearly dictates otherwise.

The terms "biomass," "biomass substrate," "cellulosic biomass," "cellulosic feedstock," and "cellulosic substrate" refer to materials that contain cellulose. Biomass can be derived from plants, animals, or microorganisms, and may include agricultural, industrial, and forestry residues, industrial and municipal wastes, and terrestrial and aquatic crops grown for energy purposes. Examples of cellulosic substrate include, but are not limited to, wood, wood pulp, paper pulp, corn fiber, corn grain, corn cobs, crop residues such as corn husks, corn stover, grasses, wheat, wheat straw, barley, barley straw, hay, rice straw, switchgrass, waste paper, paper and pulp processing waste, woody or herbaceous plants, fruit or vegetable pulp, distillers grain, rice hulls, cotton, hemp, flax, sisal, sugar cane bagasse, sorghum, soy, components obtained from milling of grains, trees, branches, roots, leaves, wood chips, sawdust, shrubs and bushes, vegetables, fruits, and flowers and mixtures thereof. In some embodiments, the biomass substrate is "pretreated," or treated using methods known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms) and combinations thereof, to increase the susceptibility of cellulose to hydrolysis.

"Saccharification" refers to the process in which substrates (e.g., cellulosic biomass) are broken down via the action of cellulases to produce fermentable sugars (e.g. monosaccharides such as but not limited to glucose).

"Fermentable sugars" refers to simple sugars (monosaccharides, disaccharides and short oligosaccharides) such as but not limited to glucose, xylose, galactose, arabinose, mannose and sucrose. Fermentable sugar is any sugar that a microorganism can utilize or ferment.

The term "fermentation" is used broadly to refer to the cultivation of a microorganism or a culture of microorganisms that use simple sugars, such as fermentable sugars, as an energy source to obtain a desired product.

As used herein, the term "cellulase" refers to a category of enzymes capable of hydrolyzing cellulose (β-1,4-glucan or β-D-glucosidic linkages) to shorter cellulose chains, oligosaccharides, cellobiose and/or glucose.

As used herein, the term "cellobiohydrolase" or "CBH" refers to a category of cellulases (EC 3.2.1.91) that hydrolyze glycosidic bonds in cellulose. In some embodiments, the cellobiohydrolase is a "type 1 cellobiohydrolase," a cellobiohydrolase belonging to the glycoside hydrolase family 7 (GH7) family of cellulases and which is also commonly called "the Cell family." Cellobiohydrolases of the GH7 family are described, for example, in the Carbohydrate Active Enzymes (CAZY) database, accessible at www.cazy.org/GH7.html.

As used herein, the term "endoglucanase" or "EG" refers to a category of cellulases (EC 3.2.1.4) that catalyze the hydrolysis of internal β-1,4 glucosidic bonds of cellulose.

As used herein, the term "β-glucosidase," "cellobiase," or "BGL" refers to a category of cellulases (EC 3.2.1.21) that catalyze the hydrolysis of cellobiose to glucose.

As used herein, the term "C1" refers to a fungal strain described by Garg, A., 1966, "An addition to the genus *Chrysosporium corda*" *Mycopathologia* 30: 3-4. "*Chrysosporium lucknowense*" includes the strains described in U.S. Pat. Nos. 6,015,707, 5,811,381 and 6,573,086; US Pat. Pub. Nos. 2007/0238155, US 2008/0194005, US 2009/0099079; International Pat. Pub. Nos., WO 2008/073914 and WO 98/15633, and include, without limitation, *Chrysosporium lucknowense* Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophila*. Other C1 strains include cells deposited under accession numbers ATCC 44006, CBS (Centraalbureau voor Schimmelcultures) 122188, CBS 251.72, CBS 143.77, CBS 272.77, CBS 122190, CBS 122189, and VKM F-3500D. Exemplary C1 derivatives include modified organisms in which one or more endogenous genes or sequences have been deleted or modified and/or one or more heterologous genes or sequences have been introduced. Derivatives include UV18#100f Δalpl, UV18#100f Δpyr5 Δalp1, UV18#100.f Δalp1 Δpep4 Δalp2, UV18#100.f Δpyr5 Δalp1 Δpep4 Δalp2 and UV18#100.f Δpyr4 Δpyr5 Δalp1 Δpep4 Δalp2, as described in WO2008073914 and WO2010107303, each of which is incorporated herein by reference.

As used herein, the term "cellobiohydrolase polypeptide" refers to a polypeptide having cellobiohydrolase activity.

As used herein, the term "cellobiohydrolase polynucleotide" refers to a polynucleotide encoding a polypeptide having cellobiohydrolase activity.

As used herein, the term "wild-type C1 cellobiohydrolase type 1a" or "wild-type C1 CBH1a" refers to SEQ ID NO:2, the mature peptide sequence lacking a signal peptide) of cellobiohydrolase type 1a that is expressed by the naturally occurring fungal strain C1.

As used herein, the term "variant" refers to a cellobiohydrolase polypeptide or polynucleotide encoding a cellobiohydrolase polypeptide comprising one or more modifications relative to wild-type C1 CBH1a or the wild-type polynucleotide encoding C1 CBH1a such as substitutions, insertions, deletions, and/or truncations of one or more amino acid residues or of one or more specific nucleotides or codons in the polypeptide or polynucleotide, respectively.

The term "pre-protein" refers to a protein including an amino-terminal signal peptide (or leader sequence) region attached. The signal peptide is cleaved from the pre-protein by a signal peptidase prior to secretion to result in the "mature" or "secreted" protein.

The terms "improved" or "improved properties," as used in the context of describing the properties of a cellobiohydrolase variant, refers to a cellobiohydrolase variant polypeptide that exhibits an improvement in a property or properties as compared to the wild-type C1 CBH1a (SEQ ID NO:2) or a specified reference polypeptide. Improved properties may include increased protein expression, increased thermoactivity, increased thermostability, increased pH activity, increased stability (e.g., increased pH stability), increased product specificity, increased specific activity, increased substrate specificity, increased resistance to substrate or end-product inhibition, increased chemical stability, reduced inhibition by glucose, increased resistance to inhibitors (e.g., acetic acid, lectins, tannic acids, and phenolic compounds), and altered pH/temperature profile.

As used herein, the term "improved thermoactivity," "increased thermoactivity," "improved specific activity," or "increased specific activity" refers to a variant enzyme displaying an increase, relative to a reference enzyme (e.g., a wild-type cellobiohydrolase), in the amount of cellobiohydrolase enzymatic activity (e.g., substrate hydrolysis) in a specified time under specified reaction conditions. Exemplary methods for measuring cellobiohydrolase activity are provided in the Examples and include, but are not limited to, measuring cellobiose production from crystalline cellulose as measured by colorimetric assay or HPLC. To compare cellobiohydrolase activity of two recombinantly expressed proteins, the specific activity (activity per mole enzyme or activity per gram enzyme) can be compared. Alternatively, cells expressing and secreting the recombinant proteins can be cultured under the same conditions and the cellobiohydrolase activity per volume culture medium can be compared.

As used herein, the term "improved thermostability" or "increased thermostability" refers to a variant enzyme displaying an increase in "residual activity" relative to a reference enzyme (e.g., a wild-type cellobiohydrolase). Residual activity is determined by (1) exposing the variant enzyme or wild-type enzyme to stress conditions of elevated temperature, optionally at lowered pH, for a period of time and then determining cellobiohydrolase activity; (2) exposing the variant enzyme or wild-type enzyme to unstressed conditions for the same period of time and then determining cellobiohydrolase activity; and (3) calculating residual activity as the ratio of activity obtained under stress conditions (1) over the activity obtained under unstressed conditions (2). For example, the cellobiohydrolase activity of the enzyme exposed to stress conditions ("a") is compared to that of a control in which the enzyme is not exposed to the stress conditions ("b"), and residual activity is equal to the ratio a/b. A variant with increased thermostability will have greater residual activity than the wild-type enzyme. In one embodiment the enzymes are exposed to stress conditions of 66° C. at pH 4.4 for 2 hr, but other cultivation conditions, such as conditions described herein, can be used.

As used herein, the term "reference enzyme" refers to an enzyme to which a variant enzyme of the present invention is compared in order to determine the presence of an improved property in the variant enzyme being evaluated, including but not limited to improved thermoactivity, improved thermostability, or improved stability. In some embodiments, a reference enzyme is a wild-type enzyme (e.g., wild-type C1 CBH1a). In some embodiments, a reference enzyme is another variant enzyme (e.g., another variant enzyme of the present invention).

As used herein, "polynucleotide" refers to a polymer of deoxyribonucleotides or ribonucleotides in either single- or double-stranded form, and complements thereof.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen, 1993, "Laboratory Techniques in Biochemistry and Molecular Biology-Hybridization with Nucleic Acid Probes," Part I, Chapter 2 (Elsevier, New York), which is incorporated herein by reference. For polynucleotides of at least 100 nucleotides in length, low to very high stringency conditions are defined as follows: prehybridization and hybridization at 42° C. in 5×SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS 50° C. (low stringency), at 55° C. (medium stringency), at 60° C. (medium-high stringency), at 65° C. (high stringency), or at 70° C. (very high stringency).

The terms "peptide," "polypeptide," and "protein" are used interchangeably herein to refer to a polymer of amino acid residues.

The term "amino acid" refers to naturally occurring and synthetic amino acids, as well as amino acid analogs. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

A "conservative substitution" as used with respect to amino acids, refers to the substitution of an amino acid with a chemically similar amino acid. Amino acid substitutions which often preserve the structural and/or functional properties of the polypeptide in which the substitution is made are known in the art and are described, for example, by H. Neurath and R. L. Hill, 1979, in "The Proteins," Academic Press, New York. The most commonly occurring exchanges are isoleucine/valine, tyrosine/phenylalanine, aspartic acid/glutamic acid, lysine/arginine, methionine/leucine, aspartic acid/asparagine, glutamic acid/glutamine, leucine/isoleucine, methionine/isoleucine, threonine/serine, tryptophan/phenylalanine, tyrosine/histidine, tyrosine/tryptophan, glutamine/arginine, histidine/asparagine, histidine/glutamine, lysine/asparagine, lysine/glutamine, lysine/glutamic acid, phenylalanine/leucine, phenylalanine/methionine, serine/alanine, serine/asparagine, valine/leucine, and valine/methionine. In some embodiments, there may be at least 1, at least 2, at least 3, at least 4, at least 5, at least 6, at least 7, at least 8, at least 9, at least 10, at least 15, at least 20, at least 25, at least 30, at least 35, or at least 40 conservative substitutions.

The following nomenclature may be used to describe substitutions in a reference sequence relative to a reference sequence or a variant polypeptide or nucleic acid sequence: "R-#-V," where # refers to the position in the reference sequence, R refers to the amino acid (or base) at that position in the reference sequence, and V refers to the amino acid (or base) at that position in the variant sequence. In some embodiments, an amino acid (or base) may be called "X," by which is meant any amino acid (or base). As a non-limiting example, for a variant polypeptide described with reference to a wild-type cellobiohydrolase type 1a pre-protein (SEQ ID NO:4), "T58V" indicates that in the variant polypeptide, the threonine at position 58 of the reference sequence is replaced by valine, with amino acid position being determined by optimal alignment of the variant sequence with SEQ ID NO:4. Similarly, "T58I/V" describes two variants: a variant in which the threonine at position 58 of the reference sequence is replaced by isoleucine and a variant in which the threonine at position 58 of the reference sequence is replaced by valine.

The term "amino acid substitution set" or "substitution set" refers to a group of amino acid substitutions. A substitution set can have 1, 2, 3, 4, 5, 6, 7, 8, 9, 10, 11, 12, 13, 14, 15, or more amino acid substitutions. In some embodiments, a substitution set refers to the set of amino acid substitutions that is present in any of the variant cellobiohydrolases listed in Table 3, Table 4, Table 5, Table 6, and/or Table 7. For example, the substitution set for Variant 5 (Table 3) consists of the amino acid substitutions S79P, G155P, S177P, S212P, K294P, and E343P.

The term "isolated" refers to a nucleic acid, polynucleotide, polypeptide, protein, or other component that is partially or completely separated from components with which it is normally associated (other proteins, nucleic acids, cells, etc.). In some embodiments, an isolated polypeptide or protein is a recombinant polypeptide or protein.

A nucleic acid (such as a polynucleotide), a polypeptide, or a cell is "recombinant" when it is artificial or engineered, or derived from or contains an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Identity" or "percent identity," in the context of two or more polypeptide sequences, refers to two or more sequences or subsequences that are the same or have a specified percentage of amino acid residues that are the same (e.g., share at least about 70%, at least about 75%, at least about 80%, at least about 85%, at least about 88% identity, at least about 89%, at least about 90%, at least about 91%, at least about 92%, at least about 93%, at least about 94%, at least about 95%, at least about 96%, at least about 97%, at least about 98%, or at least about 99% identity) over a specified region to a reference sequence, when compared and aligned for maximum correspondence over a comparison window, or designated region as measured using a sequence comparison algorithms or by manual alignment and visual inspection.

Optimal alignment of sequences for comparison and determination of sequence identity can be determined by a sequence comparison algorithm or by visual inspection (see, generally, Ausubel et al., infra). When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters.

An algorithm that may be used to determine whether a variant cellobiohydrolase has sequence identity to SEQ ID NO:2 is the BLAST algorithm, which is described in Altschul et al., 1990, *J. Mol. Biol.* 215:403-410, which is incorporated herein by reference. Software for performing BLAST analyses is publicly available through the National Center for Biotechnology Information (on the worldwide web at ncbi.nlm.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a word size (W) of 3, an expectation (E) of 10, and the BLOSUM62 scoring matrix (see Henikoff & Henikoff, 1989, *Proc. Natl. Acad. Sci. USA* 89:10915). Other programs that may be used include the Needleman-Wunsch procedure, J. Mol. Biol. 48: 443-453 (1970), using blosum62, a Gap start penalty of 7 and gap extend penalty of 1; and gapped BLAST 2.0 (see Altschul, et al. 1997, Nucleic Acids Res., 25:3389-3402) both available to the public at the National Center for Biotechnology Information Website.

Multiple sequences can be aligned with each other by visual inspection or using a sequence comparison algorithm, such as PSI-BLAST (Altschul, et al., 1997, supra) or "T-Coffee" (Notredame et al., 2000, J. Mol. Bio. 302:205-17). T-Coffee alignments may be carried out using default parameters (T-Coffee Technical Documentation, Version 8.01, July 2009, WorldWideWeb .tcoffee.org), or Protein Align. In Protein Align, alignments are computed by optimizing a function based on residue similarity scores (obtained from applying an amino acid substitution matrix to pairs of aligned residues) and gap penalties. Penalties are imposed for introducing an extending gaps in one sequence with respect to another. The final optimized function value is referred to as the alignment score. When aligning multiple sequences, Protein Align optimizes the "sum of pairs" score, i.e., the sum of all the separate pairwise alignment scores.

The phrase "substantial sequence identity" or "substantial identity," in the context of two nucleic acid or polypeptide sequences, refers to a sequence that has at least 70% identity to a reference sequence. Percent identity can be any integer from 70% to 100%. Two nucleic acid or polypeptide sequences that have 100% sequence identity are said to be "identical." A nucleic acid or polypeptide sequence are said to have "substantial sequence identity" to a reference sequence when the sequences have at least about 70%, at least about 75%, at least 80%, at least 85%, at least 90%, at least 91%, at least 92%, at least 93%, at least 94%, at least 95%, at least 96%, at least 97%, at least 98%, or at least 99% or greater sequence identity as determined using the methods described herein, such as BLAST using standard parameters as described above. For an alignment that extends along the entire length of SEQ ID NO:2, there may be at least 357, at least 382, at least 407, at least 433, at least 459, at least 464, at least 469, at least 474, at least 479, at least 484, at least 489, at least 494, at least 499, or at least 504 amino acids identical between a variant sequence and SEQ ID NO:2.

A "vector" is a DNA construct for introducing a DNA sequence into a cell. A vector may be an expression vector that is operably linked to a suitable control sequence capable of effecting the expression in a suitable host of the polypeptide encoded in the DNA sequence. An "expression vector" has a promoter sequence operably linked to the DNA sequence (e.g., transgene) to drive expression in a host cell, and in some embodiments a transcription terminator sequence.

The term "expression" includes any step involved in the production of the polypeptide including, but not limited to, transcription, post-transcriptional modification, translation, post-translational modification, and secretion.

The term "operably linked" refers to a configuration in which a control sequence is appropriately placed at a position relative to the coding sequence of the DNA sequence such that the control sequence influences the expression of a polypeptide.

An amino acid or nucleotide sequence (e.g., a promoter sequence, signal peptide, terminator sequence, etc.) is "heterologous" to another sequence with which it is operably linked if the two sequences are not associated in nature.

The terms "transform" or "transformation," as used in reference to a cell, means a cell has a non-native nucleic acid sequence integrated into its genome or as an episome (e.g., plasmid) that is maintained through multiple generations.

The term "culturing" refers to growing a population of microbial cells under suitable conditions in a liquid or solid medium.

The term "introduced," as used in the context of inserting a nucleic acid sequence into a cell, means conjugated, transfected, transduced or transformed (collectively "transformed") or otherwise incorporated into the genome of, or maintained as an episome in, the cell.

DETAILED DESCRIPTION OF THE INVENTION

I. Introduction

Fungi, bacteria, and other organisms produce a variety of cellulases and other enzymes that act in concert to catalyze decrystallization and hydrolysis of cellulose to yield fermentable sugars. One such fungus is C1, which was described by Garg, 1966, "An addition to the genus *Chrysosporium corda*" *Mycopathologia* 30: 3-4; see also U.S. Pat. Nos. 6,015,707 and 6,573,086, which are incorporated herein by reference for all purposes. One C1 cellulase of interest is the cellobiohydrolase referred to as "C1 cellobiohydrolase type 1a" or "CBH1a".

The cellobiohydrolase variants described herein are useful for the production of fermentable sugars from cellulosic biomass. In one aspect, the present invention relates to cellobiohydrolase variants that have improved properties, relative to wild-type C1 CBH1a, under process conditions used for saccharification of biomass. Exemplary properties include increased thermostability and/or increased thermoactivity and/or increased pH tolerance. In another aspect, the invention provides a host cell containing a recombinant nucleic acid sequence encoding a variant cellobiohydrolase. In another aspect, the present invention provides a method for expressing a variant cellobiohydrolase by maintaining the cell under conditions in which the cellobiohydrolase protein is expressed and, preferably, secreted. In another aspect, the present invention provides methods of generating fermentable sugars from cellulosic biomass, by contacting the biomass with a cellulase composition comprising a CBH1a variant as described herein under conditions suitable for the production of fermentable sugars. As described in greater detail below, recombinant host cells expressing cellobiohydrolase variants of the invention may be combined with a cellulosic biomass or other cellobiohydrolase substrate under conditions in which the cellobiohydrolase is expressed and/or secreted by the cells as part of a saccharification process. Alternatively, a substantially or partially purified recombinant cellobiohydrolase protein may be contacted with cellulosic biomass or other cellobiohydrolase substrate.

Various aspects of the invention are described in the following sections.

II. Cellobiohydrolase Type 1 Variants

Properties of Cellobiohydrolase Variants

In one aspect, the present invention provides C1 CBH1a variants having improved properties over a wild-type cellobiohydrolase. In some embodiments, the CBH1a variants of the present invention exhibit increased thermostability and/or increased thermoactivity in comparison to a wild-type type 1 cellobiohydrolase (e.g., a C1 CBH1a having the amino acid sequence of SEQ ID NO:2) under conditions relevant to commercial cellulose hydrolysis processes.

In some embodiments, the present invention provides a recombinant C1 CBH1a variant comprising at least about 70% (or at least about 75%, at least about 80%, at least about 85%, at least about 90%, at least about 95%, at least about 96%, at least about 97%, at least about 98%, or at least about 99%) sequence identity to SEQ ID NO:2 and comprising an amino acid substitution at one or more positions selected from Y2, K4, T22, T24, S30, T32, G39, S48, I49, T58, A64, N66, E69, S79, P82, I90, T98, T102, G116, Q117, Y118, I122, T126, G155, S177, S192, A205, N209, S212, N218, T221, A240, A241, A242, T264, Y265, T267, I273, Q286, K294, E343, P381, V394, S401, T402, W403, I405, A417, A432, G448, S452, S475, S483, T486, G490, A492, G502, Q508, P512, and L526, wherein the position is numbered with reference to a wild-type C1 CBH1a pre-protein (e.g., SEQ ID NO:4), and wherein the variant has increased thermostability and/or thermoactivity in comparison to secreted wild-type C1 CBH1a (SEQ ID NO:2). In some embodiments, a CBH1a variant of the present invention has an amino acid sequence that is encoded by a nucleic acid that hybridizes under stringent conditions to the complement of SEQ ID NO:1 (e.g., over substantially the entire length of a nucleic acid exactly complementary to SEQ ID NO:1) and comprises an amino acid substitution at one or more positions selected from Y2, K4, T22, T24, S30, T32, G39, S48, I49, T58, A64, N66, E69, S79, P82, I90, T98, T102, G116, Q117, Y118, I122, T126, G155, S177, S192, A205, N209, S212, N218, T221, A240, A241, A242, T264, Y265, T267, I273, Q286, K294, E343, P381, V394, S401, T402, W403, I405, A417, A432, G448, S452, S475, S483, T486, G490, A492, G502, Q508, P512, and L526, wherein the position is numbered with reference to a wild-type C1 CBH1a pre-protein (e.g., SEQ ID NO:4).

In some embodiments, the present invention provides a recombinant C1 CBH1a variant comprising at least about 70% (or at least about 75%, at least about 80%, at least about 85%, at least about 90%, at least about 95%, at least about 96%, at least about 97%, at least about 98%, or at least about 99%) sequence identity to SEQ ID NO:2 and comprising one or more amino acid substitutions selected from Y2H, K4Q, T22H, T24F/I/K/L/N/R/V, S30P, T32M, G39R, S48W, I49V, T58I/N, A64S/T, N66C/P, E69C/D/N/T, S79P, P82K/M, I90L/V, T98L, T102H, G116T, Q117N, Y118G/H, I122V, T126V, G155P, S177P, S192A, A205C/G, N209G, S212P, N218H, T221H/Q/W, A240S, A241T, A242V, T264L, Y265W, T267K, I273P, Q286M, K294P, E343P, P381G, V394A/D/G/L/Q/S, S401D, T402G, W403F/Y, I405V, A417P, A432F, G448D, S452E, S475G, S483D/K/L, T486I/V/Y, G490F/M, A492V, G502R, Q508H/S, P512G, and L526A, wherein the position is numbered with reference to a wild-type C1 CBH1a pre-protein (e.g., SEQ ID NO:4). In some embodiments, a CBH1a variant of the present invention has an amino acid sequence that is encoded by a nucleic acid that hybridizes under stringent conditions to the complement of SEQ ID NO:1 (e.g., over substantially the entire length of a nucleic acid exactly complementary to SEQ ID NO:1) and comprises one or more amino acid substitutions selected from Y2H, K4Q, T22H, T24F/I/K/L/N/R/V, S30P, T32M, G39R, S48W, I49V, T58I/V, A64S/T, N66C/P, E69C/D/N/T, S79P, P82K/M, I90L/V, T98L, T102H, G116T, Q117N, Y118G/H, I122V, T126V, G155P, S177P, S192A, A205C/G, N209G, S212P, N218H, T221H/Q/W, A240S, A241T, A242V, T264L, Y265W, T267K, I273P, Q286M, K294P, E343P, P381G, V394A/D/G/L/Q/S, S401D, T402G, W403F/Y, I405V, A417P, A432F, G448D, S452E, S475G, S483D/K/L, T486I/V/Y, G490F/M, A492V, G502R, Q508H/S, P512G, and L526A, wherein the position is numbered with reference to a wild-type C1 CBH1a pre-protein (e.g., SEQ ID NO:4).

In some embodiments, a CBH1a variant of the present invention exhibits at least about a 1.0 fold, at least about a 2.0 fold, at least about a 3.0 fold, at least about a 4.0 fold, at least about a 5.0 fold, at least about a 6.0 fold, at least about a 7.0 fold, at least about a 8.0 fold, at least about a 9.0 fold, at least about a 10 fold increase or more in thermostability relative to secreted wild-type C1 CBH1a (SEQ ID NO:2), as identified in Table 1, Table 2, Table 3, Table 4, or Table 5, wherein fold improvement in thermostability is measured as described in the Examples (i.e., expressed in *S. cerevisiae*).

In some embodiments, a CBH1a variant comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid residues which have been substituted (e.g., with substitutions described herein) as compared to the amino acid sequence of the wild-type cellobiohydrolase protein from which the cellobiohydrolase variant is derived.

In some embodiments, a CBH1a variant of the present invention comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:2 and comprises an amino acid substitution set selected from the substitution sets showing at least 1-, 2-, 3-, 4-, 5-, 6-, 7-, or -8 fold or higher improvement in thermostability over secreted wild-type C1 CBH1a (SEQ ID NO:2), as identified in Table 3.

In some embodiments, a CBH1a variant of the present invention comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:2 and comprises an amino acid substitution set selected from the substitution sets showing at least 1- to 4-fold or at least 4-fold or higher improvement in thermostability over the cellobiohydrolase variant 5 (SEQ ID NO:28), as identified in Table 4.

In some embodiments, a CBH1a variant of the present invention comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:2 and comprises an amino acid substitution set selected from the substitution sets showing at least 1- to 2-fold or at least 2-fold or higher improvement in thermostability over the cellobiohydrolase variant 15 (SEQ ID NO:32), as identified in Table 5.

In some embodiments, a CBH1a variant of the present invention comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:2 and comprises an amino acid substitution set selected from the substitution sets showing at least 1- to 1.5-fold or at least 1.5 fold or higher improvement in thermostability over the cellobiohydrolase variant 17 (SEQ ID NO:34), as identified in Table 6.

In some embodiments, a CBH1a variant of the present invention comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:2 and comprises an amino acid substitution set selected from the substitution sets showing at least 1.1- to 1.2-fold, 1.2- to 1.3-fold, or 1.3-fold or higher improvement in thermostability over the cellobiohydrolase variant 20 (SEQ ID NO:36), as identified in Table 7.

In some embodiments, the present invention encompasses any of the cellobiohydrolase proteins in Tables 1-5, as well as any variants that comprise an amino acid substitution set provided in Table 1, Table 2, Table 3, Table 4, or Table 5 and comprise at least 70% (or at least 75%, at least 80%, at least 85%, at least 90%, at least 91%, at least 92%, at least 93%, at least 94%, at least 95%, at least 96%, at least 97%, at least 98%, or at least 99%) sequence identity to secreted wild-type C1 CBH1a (SEQ ID NO:2).

Certain cellobiohydrolase variants comprise an amino acid substitution at one or more positions selected from S79, G155, S177, S212, K294, and E343. In some embodiments, a C1 CBH1a variant of the present invention comprises one or more amino acid substitutions selected from S79P, G155P, S177P, S212P, K294P, and E343P. In some embodiments, a C1 CBH1a variant of the present invention comprises the amino acid substitutions of variant 5, i.e., the amino acid substitutions S79P, G155P, S177P, S212P, K294P, and E343P. In some embodiments, the C1 CBH1a variant has the amino acid sequence of SEQ ID NO:28.

Certain cellobiohydrolase variants comprise an amino acid substitution at one or more positions selected from S30, T58, S79, P82, Q117, G155, S177, S212, K294, E343, P381, and A417. In some embodiments, a C1 CBH1a variant of the present invention comprises one or more amino acid substitutions selected from S30P, T58I, S79P, P82M, Q117N, G155P, S177Q, S212P, K294P, E343P, P381G, and A417P. In some embodiments, a C1 CBH1a variant of the present invention comprises the amino acid substitutions of variant 15, i.e., the amino acid substitutions S30P, T58I, S79P, P82M, Q117N, G155P, S177Q, S212P, K294P, E343P, P381G, and A417P. In some embodiments, the C1 CBH1a variant has the amino acid sequence of SEQ ID NO:32.

Certain cellobiohydrolase variants comprise an amino acid substitution at one or more positions selected from S30, T58, S79, P82, I90, Q117, G155, S177, N209, S212, T221, Q286, K294, E343, P381, and A417. In some embodiments, a C1 CBH1a variant of the present invention comprises one or more amino acid substitutions selected from S30P, T58I, S79P, P82M, I90V, Q117N, G155P, S177P, N209G, S212P, T221W, Q286M, K294P, E343P, P381G, and A417P. In some embodiments, a C1 CBH1a variant of the present invention comprises the amino acid substitutions of variant 17, i.e., the amino acid substitutions S30P, T58I, S79P, P82M, I90V, Q117N, G155P, S177P, N209G, S212P, T221W, Q286M, K294P, E343P, P381G, and A417P. In some embodiments, the C1 CBH1a variant has the amino acid sequence of SEQ ID NO:34.

Certain cellobiohydrolase variants comprise an amino acid substitution at one or more positions selected from S30, T58, S79, P82, I90, Q117, G155, S177, N209, S212, T221, Q286, K294, E343, P381, S401, and A417. In some embodiments, a C1 CBH1a variant of the present invention comprises one or more amino acid substitutions selected from S30P, T58I, S79P, P82M, I90V, Q117N, G155P, S177P, N209G, S212P, T221W, Q286M, K294P, E343P, P381G, S401D, and A417P. In some embodiments, a C1 CBH1a variant of the present invention comprises the amino acid substitutions of variant 20, i.e., the amino acid substitutions S30P, T58I, S79P, P82M, I90V, Q117N, G155P, S177P, N209G, S212P, T221W, Q286M, K294P, E343P, P381G, S401D, and A417P. In some embodiments, the C1 CBH1a variant has the amino acid sequence of SEQ ID NO:36.

Certain cellobiohydrolase variants comprise an amino acid substitution at one or more positions selected from S30, T58, S79, I90, Q117, G155, S177, N209, S212, T221, Q286, K294, E343, P381, V394, S401, and A417. In some embodiments, a C1 CBH1a variant of the present invention comprises one or more amino acid substitutions selected from S30P, T58I, S79P, I90L, Q117N, G155P, S177P, N209G, S212P, T221W, Q286M, K294P, E343P, P381G, V394A, S401D, and A417P. In some embodiments, a C1 CBH1a variant of the present invention comprises the amino acid substitutions of variant 32, i.e., the amino acid substitutions S30P, T58I, S79P, I90L, Q117N, G155P, S177P, N209G, S212P, T221W, Q286M, K294P, E343P, P381G, V394A, S401D, and A417P. In some embodiments, the C1 CBH1a variant has the amino acid sequence of SEQ ID NO:38.

In some embodiments, an amino acid substitution from glutamine at the position corresponding to residue 117 in wild-type C1 CBH1a pre-protein (e.g., SEQ ID NO:4) results in a significant increase in specific activity of the cellobiohydrolase protein. Thus, in one aspect, the present invention provides a method of increasing the specific activity of C1 CBH1a or a variant thereof by introducing an amino acid other than glutamine at position 117, wherein the position is numbered with reference to the wild-type C1 CBH1a pre-protein (e.g., SEQ ID NO:4). In some embodiments, the amino acid other than glutamine is asparagine.

In some embodiments, the present invention provides a recombinant C1 CBH1a variant comprising at least 70% (or at least 75%, at least 80%, at least 85%, at least 90%, at least 91%, at least 92%, at least 93%, at least 94%, at least 95%, at least 96%, at least 97%, at least 98%, or at least 99%) sequence identity to SEQ ID NO:2 and comprising a pair of amino acid substitutions selected from A205C and V207C, and C78V and A205C, wherein the position is numbered with reference to a wild-type C1 CBH1a pre-protein (e.g., SEQ ID NO:4). Without being bound to a particular theory, it is believed that introducing cysteine mutations in the amino acid sequence of C1 cellobiohydrolase results in the formation of disulfide bonds that enhance the stability of the C1 cellobiohydrolase protein. In some embodiments, a CBH1a variant of the present invention comprises a pair of amino acid substitutions at A205C and V207C. In some embodiments, a CBH1a variant of the present invention comprises a pair of amino acid substitutions at C78V and A205C.

ProSAR Analysis of Cellobiohydrolase Variants

Cellobiohydrolase variants having one or more amino acid substitutions relative to a wild-type cellobiohydrolase, such as C1 CBH1a, can be experimentally generated and characterized for improved properties such as increased thermostability or increased thermoactivity as compared to wild-type cellobiohydrolase. Such experimentally produced variants can subsequently be statistically analyzed in order to determine which amino acid substitution or substitutions are particularly beneficial or detrimental in conferring the desired property (e.g., improved thermostability or improved thermoactivity).

Sequence-activity analysis of variants was performed in accordance with the methods described in U.S. Pat. No. 7,793,428; R. Fox et al., 2003, "Optimizing the search algorithm for protein engineering by directed evolution," Protein Eng. 16(8):589-597, and R. Fox et al., 2005, "Directed molecular evolution by machine learning and the influence of nonlinear interactions," J. Theor. Biol. 234(2):187-199, all of which are incorporated herein by reference, to determine whether a mutation has a beneficial, neutral, or deleterious effect on stability or activity when combined with other mutations.

As described herein, substitutions at the following positions, numbered with reference to a wild-type C1 CBH1a pre-protein (e.g., SEQ ID NO:4), were identified as being beneficial for increasing thermostability and/or thermoactivity: K4, T24, S48, T58, N66, E69, S79, I90, G116, Q117, Y118, I122, T126, G155, A205, N209, S212, N218, T221, A240, A241, A242, T267, I273, Q286, K294, E343, P381, H392, V394, T402, A432, A417, G448, A492, G502, and Q508.

Certain cellobiohydrolase variants of the present invention have an amino acid sequence that includes at least one amino acid substitution at one or more amino acid residues selected from S79, G155, S212, K294, and E343, wherein the amino acid residues are numbered with reference to SEQ ID NO:1. Amino acid substitutions at one or more of these positions are predicted to be beneficial substitutions for increasing cellobiohydrolase thermostability and/or thermoactivity. In some embodiments, a cellobiohydrolase variant of the present invention has an amino acid sequence that comprises one or more amino acid substitutions selected from S79P, G155P, S212P, K294P, and E343P, which are predicted to be beneficial substitutions for increasing thermostability and/or thermoactivity.

Certain cellobiohydrolase variants of the present invention have an amino acid sequence that includes at least one amino acid substitution at one or more amino acid residues selected from K4, N209, S212, A240, A241, and K294, wherein the amino acid residues are numbered with reference to SEQ ID NO:1. Amino acid substitutions at one or more of these positions are predicted to be beneficial substitutions for increasing cellobiohydrolase thermostability and/or thermoactivity. In some embodiments, a cellobiohydrolase variant of the present invention has an amino acid sequence that comprises one or more amino acid substitutions selected from K4Q, N209G, S212P, A240S, A241T, and K294P, which are predicted to be beneficial substitutions for increasing thermostability and/or thermoactivity.

Certain cellobiohydrolase variants of the present invention have an amino acid sequence that includes at least one amino acid substitution at one or more amino acid residues selected from T24, S48, E69, T126, N209, and I273, wherein the amino acid residues are numbered with reference to SEQ ID NO:1. Amino acid substitutions at one or more of these positions are predicted to be beneficial substitutions for increasing cellobiohydrolase thermostability and/or thermoactivity. In some embodiments, a cellobiohydrolase variant of the present invention has an amino acid sequence that comprises one or more amino acid substitutions selected from T24F/I/K/N/R/V, S48W, E69C, T126V, N209G, and I273P, which are predicted to be beneficial substitutions for increasing thermostability and/or thermoactivity.

Certain cellobiohydrolase variants of the present invention have an amino acid sequence that includes at least one amino acid substitution at one or more amino acid residues selected from T58, Q117, T221, P381, and A417, wherein the amino acid residues are numbered with reference to SEQ ID NO:1. Amino acid substitutions at one or more of these positions are predicted to be beneficial substitutions for increasing cellobiohydrolase thermostability and/or thermoactivity. In some embodiments, a cellobiohydrolase variant of the present invention has an amino acid sequence that comprises one or more amino acid substitutions selected from T58I, Q117N, T221H, P381G, and A417P, which are predicted to be beneficial substitutions for increasing thermostability and/or thermoactivity.

Certain cellobiohydrolase variants of the present invention have an amino acid sequence that includes at least one amino acid substitution at one or more amino acid residues selected from Y118, T267, I273, T402, A432, and G448, wherein the amino acid residues are numbered with reference to SEQ ID NO:1. Amino acid substitutions at one or more of these positions are predicted to be beneficial substitutions for increasing cellobiohydrolase thermostability and/or thermoactivity. In some embodiments, a cellobiohydrolase variant of the present invention has an amino acid sequence that comprises one or more amino acid substitutions selected from Y118H, T267K, I273P, T402G, A432F, and G448D, which are predicted to be beneficial substitutions for increasing thermostability and/or thermoactivity.

Certain cellobiohydrolase variants of the present invention have an amino acid sequence that includes at least one amino acid substitution from one or more amino acid residues selected from T24, T58, I90, G116, I122, T221, H392, and G502, wherein the amino acid residues are numbered with reference to SEQ ID NO:1. Amino acid substitutions at one or more of these positions are predicted to be beneficial substitutions for increasing cellobiohydrolase thermostability and/or thermoactivity. In some embodiments, a cellobiohydrolase variant of the present invention has an amino acid sequence that comprises one or more amino acid substitutions selected from T24L, T58L, I90V, G116T, I122V, T221W, H392P, and G502R, which are predicted to be beneficial substitutions for increasing thermostability and/or thermoactivity.

Certain cellobiohydrolase variants of the present invention have an amino acid sequence that includes at least one amino acid substitution from one or more amino acid residues selected from T24, E69, I90, G116, N209, Q286, and G502, wherein the amino acid residues are numbered with reference to SEQ ID NO:1. Amino acid substitutions at one or more of these positions are predicted to be beneficial substitutions for increasing cellobiohydrolase thermostability and/or thermoactivity. In some embodiments, a cellobiohydrolase variant of the present invention has an amino acid sequence that comprises one or more amino acid substitutions selected from T241/K/L/N/V, E69C, I90V, G116T, N209G, Q286M, and G502R, which are predicted to be beneficial substitutions for increasing thermostability and/or thermoactivity.

Certain cellobiohydrolase variants of the present invention have an amino acid sequence that includes at least one amino acid substitution from one or more amino acid residues selected from T24, E69, G116, Y118, A205, V394, A492, G502, and Q508, wherein the amino acid residues are numbered with reference to SEQ ID NO:1. Amino acid substitutions at one or more of these positions are predicted to be beneficial substitutions for increasing cellobiohydrolase thermostability and/or thermoactivity. In some embodiments, a cellobiohydrolase variant of the present invention has an amino acid sequence that comprises one or more amino acid substitutions selected from T24I/K, E69C, G116T, Y118H, A205C/G, V394L, A492V, G502R, and Q508H, which are predicted to be beneficial substitutions for increasing thermostability and/or thermoactivity.

Certain cellobiohydrolase variants of the present invention have an amino acid sequence that includes at least one amino acid substitution from one or more amino acid residues selected from T24, N66, G116, N218, and A242, wherein the amino acid residues are numbered with reference to SEQ ID NO:1. Amino acid substitutions at one or more of these positions are predicted to be beneficial substitutions for increasing cellobiohydrolase thermostability and/or thermoactivity. In some embodiments, a cellobiohydrolase variant of the present invention has an amino acid sequence that comprises one or more amino acid substitutions selected from T24F/I/V, N66C, G116T, N218H, and A242V, which are predicted to be beneficial substitutions for increasing thermostability and/or thermoactivity.

III. Cellobiohydrolase Variants with C-Terminal Truncations and/or Disrupted Cellulose Binding Domains In some embodiments, a CBH1a variant of the present invention is truncated at the C-terminus. As described in Example 8, a variant in which the 16 C-terminal residues were deleted and replaced with a 7-mer exhibited significant thermostability and tolerance for low pH. Notably, an effect of this mutation was to disrupt disulfide bonds formed by cysteines at positions 498 and 515 (pair 1) and 509 and 525 (pair 2) corresponding to a wild-type C1 CBH1a pre-protein (e.g., SEQ ID NO:4). Without being bound to a particular theory, it is believed that the effect of these changes is to disrupt folding of the cellulose binding module (CBM). Additionally, two aromatic residues, W521 and Y522, positioned on the putative binding face, were removed. Thus, this CBH1a variant likely has a non-functional CBM which may be unable to bind substrate.

Accordingly, in one aspect the present invention provides a CBH1a variant wherein the CBM, or a substantial portion of the CBM, has been modified to disrupt folding and/or template binding. Such a modified CBM or deleted CBM is likely to beneficial for thermostability and tolerance for low pH. In some embodiments, the CBM modification is a substitution (to a non-cysteine residue) of one or more of C498, C515, C509, and C525, wherein the positions are numbered with reference to a wild-type C1 CBH1a pre-protein (e.g., SEQ ID NO:4). In some embodiments, the modification is a substitution of either or both of C498 and C509. In some embodiments, the modification is a substitution of either or both of C515 and C525. In some embodiments, the modification is a substitution of either or both C498 and C509 and a substitution of either or both of C515 and C525. In some embodiments, the CBM modification is a deletion of W521 or the replacement of W521 with a non-aromatic residue. In some embodiments, the CBM modification is a deletion of Y522 or the replacement of Y522 with a non-aromatic residue. In some embodiments, the CBM modification is a deletion of W521 or the replacement of W521 with a non-aromatic residue and the deletion of Y522 or the replacement of Y522 with a non-aromatic residue.

In some embodiments, one or more of these modifications in the CBM is combined with one or more substitutions described herein (e.g., an individual substitution or a substitution set listed in Table 1, Table 2, Table 3, Table 4, or Table 5).

The C1 CBH1a CBM comprises residues 491-526 of SEQ ID NO:4. In some embodiments, a CBH1a variant of the present invention comprises the entire length of the CBM (optionally with the above-described modifications and optionally with other substitutions and/or modifications as described herein). In some embodiments, the CBH1a variant has a C-terminal deletion of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 residues. In some embodiments, the CBH1a variant has a C-terminal deletion of 1-10, 5-20, or 10-35 residues. In some embodiments, the CBH1a variant comprises a C-terminal deletion as described herein and further comprises one or more non-CBM residues appended to the C-terminus of the variant polypeptide. As a non-limiting example, in one embodiment the CBH1a variant has a C-terminal deletion of 16 residues and a 7-mer is appended to the C-terminus of the polypeptide. In some embodiments, the 7-mer is ARTLAPS (SEQ ID NO:22).

IV. Exemplary Substitutions in Cellobiohydrolase Homologs

In another aspect, the present invention provides cellobiohydrolase proteins that are variants of naturally occurring cellobiohydrolases of fungal species other than C1 which comprise a substitution or modification at least one position corresponding to a position of a substitution or modification of a C1 CBH1a described herein, and which have improved properties relative the naturally occurring fungal cellobiohydrolase.

In particular, analogous substitutions may be made in fungal cellobiohydrolases with significant sequence similarity to C1 CBH1a. For example, many fungi (including but not limited to *Thielavia, Humicola, Chaetomium, Neurospora, Chaetomidium, Botryosphaeria, Trichophaea, Aspergillus, Schizophyllum, Agaricus, Sporotrichium, Corynascus, Myceliophthora, Acremonium, Thermoascus, Alternaria, Botryotinia, Phanerochaete, Claviceps, Cochliobolus, Cryphonectria, Emericella, Fusarium, Gibberella, Hypocrea, Irpex, Magnaporthe, Nectria, Neosartorya, Penicillium, Phanerochaete, Pleurotus, Podospora, Polyporus, Sclerotinia, Sordaria, Talaromyces, Trichoderma*, and *Volvariella* species) express cellobiohydrolases that are structurally homologous to the C1 CBH1a. For example, structurally similar cellobiohydrolases include *Acremonium thermophilum* CAM98445.1; *Agaricus bisporus* Q92400.1; *Alternaria alternate* AAF05699.1; *Aspergillus aculeatus* O59843.1; *Aspergillus clavatus* XP_001268257.1; *Aspergillus flavus* XP_001818879.1; *Aspergillus fumigatus* XP_751044.1; *Aspergillus nidulans* XP_662780.1; *Aspergillus niger* Q9UVS8.1; *Aspergillus oryzae* XP_001727881.1; *Aspergillus terreus* XP_001214180.1; *Botryotinia fuckeliana* XP_001555330.1; *Chaetomium thermophilum* CAM98448.1; *Phanerochaete Chrysosporium* 1GPI_A;

*Claviceps purpurea* CAA68840.1; *Cochliobolus carbonum* Q00328.1; *Cryphonectria parasitica* Q00548.1; *Emericella nidulans* AAM54069.1; *Fusarium oxysporum* P46238.1; *Fusarium poae* AAX60003.1; *Fusarium venenatum* AAX60001.1; *Gibberella avenacea* AAS82857.1; *Gibberella pulicaris* AAS82858.1; *Gibberella zeae* XP_380747.1; *Humicola grisea* P15828.2; *Hypocrea koningii* P62694.1; *Hypocrea lixii* Q9P8P3.1; *Hypocrea virens* ACF93800.1; *Irpex lacteus* BAA76365.1; *Magnaporthe grisea* 70-15XP_370337.1; *Nectria haematococca* EEU36278.1; *Neosartorya fischeri* XP_001258278.1; *Neurospora crassa* XP_962498.1; *Penicillium chrysogenum* AAV65115.1; *Penicillium decumbens* ACV95805.1; *Penicillium funiculosum* CAC85737.1; *Penicillium janthinellum* Q06886.1; *Penicillium marneffei* ATCC 18224; XP_002149324.1; *Penicillium occitanis* AAT99321.1; *Penicillium oxalicum* ACE60553.1; *Phanerochaete chrysosporium* CAA82762.1; *Pleurotus* sp. 'Florida' CAK18913.1; *Podospora anserine* XP_001903333.1; *Polyporus arcularius* BAF80326.1; *Sclerotinia sclerotiorum* XP_001596118.1; *Sordaria macrospora* CBI53288.1; *Talaromyces emersonii* AAL33603.2; *Talaromyces stipitatus* XP_002484839.1; *Thermoascus aurantiacus* CAM98447.1; *Trichoderma* sp. XST1ACH96125.1; *Trichoderma viride* CAA37878.1; *Trichoderma reseipdb*|1CEL|A; *Volvariella volvacea* AAT64007.1. (Accession numbers, where given, are from GenBank, Protein Data Bank, SwissProt, Protein Research Foundation or Protein Information Resource databases.)

In some embodiments, a recombinant cellobiohydrolase of the present invention is derived from a fungal protein shown in Table 1.

TABLE 1

Cellobiohydrolase homologs having significant sequence identity to C1 CBH1a

| Organism | Accession No. | % identity to SEQ ID NO: 2 | Protein length (aa)* | SEQ ID NO |
|---|---|---|---|---|
| C1 | | 100 | 526 | 2 |
| *Thielavia australiensis* | gi\|29160311\|emb\|CAD79782.1\| | 82 | 538 | 5 |
| *Humicola grisea* | gi\|950686\|dbj\|BAA09785.1\| | 81 | 525 | 6 |
| *Chaetomium thermophilum* | gi\|156712282\|emb\|CAM98448.1\| | 79 | 532 | 7 |
| *Sordaria macrospora* | emb\|CBI55936.1\| | 75 | 522 | 8 |
| *Chaetomidium pingtungium* | gi\|29160357\|emb\|CAD79795.1\| | 65 | 532 | 9 |
| *Botryosphaeria rhodina* | gi\|29160339\|emb\|CAD79786.1\| | 65 | 454 | 10 |
| *Trichophaea saccata* | gi\|29160341\|emb\|CAD79787.1\| | 64 | 458 | 11 |
| *Aspergillus nidulans* | gi\|40747437\|gb\|EAA66593.1\| | 64 | 526 | 12 |
| *Schizophyllum commune* | gi\|61743603\|gb\|AAX55505.1\| | 63 | 455 | 13 |
| *Agaricus bisporus* | gi\|1679595\|emb\|CAA90422.1\| | 61 | 506 | 14 |

*including signal peptide sequence

It is within the ability of one of ordinary skill in the art to identify other examples of structurally homologous proteins. The present invention provides variants of these and other homologous cellobiohydrolase proteins in which substitutions are made at residues corresponding to those identified herein in the C1 CBH1a protein.

To produce CBH1a homologs with improved properties, the sequences of C1 CBH1a and the cellobiohydrolase homolog (e.g., a homolog listed in Table 1) can be aligned in a pairwise manner as described supra. Based on the alignment, a residue in a position in the homolog that corresponds, based on the alignment, with a specified position in C1 CBH1a is identified.

Thus, in some embodiments, the present invention provides a recombinant cellobiohydrolase variant comprising at least 50% (or at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%) sequence identity to SEQ ID NO:2 and comprising one or more amino acid substitutions selected from X2H, X4Q, X22H, X24F/I/K/L/N/R/V, X30P, X32M, X39R, X48W, X49V, X58I/V, X64S/T, X66C/P, X69C/D/N/T, X79P, X82K/M, X90L/V, X98L, X102H, X116T, X117N, X118G/H, X122V, X126V, X155P, X177P, X192A, X205C/G, X209G, X212P, X218H, X221H/Q/W, X240S, X241T, X242V, X264L, X265W, X267K, X273P, X286M, X294P, X343P, X381G, X394A/D/G/L/Q/S, X401D, X402G, X403F/Y, X405V, X417P, X432F, X448D, X452E, X475G, X483D/K/L, X486I/V/Y, X490F/M, X492V, X502R, X508H/S, X512G, and X526A, wherein the position is numbered with reference to a wild-type C1 CBH1a pre-protein (e.g., SEQ ID NO:4), and wherein the cellobiohydrolase variant has increased thermostability and/or thermoactivity in comparison to secreted wild-type CBH1a (SEQ ID NO:2). In some embodiments, the cellobiohydrolase variant of the present invention is derived from a protein from a fungal strain. In some embodiments, the isolated cellobiohydrolase variant comprises at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a cellobiohydrolase type 1 from C1 (SEQ ID NO:2), *Thielavia australiensis* (SEQ ID NO:5), *Humicola grisea* (SEQ ID NO:6), *Chaetomium thermophilum* (SEQ ID NO:7), *Sordaria macrospora* (SEQ ID NO:8), *Chaetomidium pingtungium* (SEQ ID NO:9), *Botryosphaeria rhodina* (SEQ ID NO:10), *Trichophaea saccata* (SEQ ID NO:11), *Aspergillus nidulans* (SEQ ID NO:12), *Schizophyllum commune* (SEQ ID NO:13), or *Agaricus bisporus* (SEQ ID NO:14).

As a non-limiting example, FIG. 6 shows an alignment between C1 CBH1a and an *H. grisea* cellobiohydrolase. The residues located at positions of substitution in C1 variant 15 are shown in bold and underlined. Table 2 shows the equivalent positions of substitution in C1 CBH1a and *H. grisea* cellobiohydrolase. Introducing an amino acid substitution at one or more of these positions is expected to result in a protein with improved properties. For example, in some embodiments, an amino acid substitution at one or more of these positions in *H. grisea* is selected from the amino acid substitution set for C1 variant 15 (S30P; T58I; S79P; P82M; Q117N; G155P; S177Q; S212P; K294P; E343P; P381G; and A417P), resulting in one or more amino acid substitutions in H. grisea selected from S31P; T59I; T80P; P83M; Q118N; G156P; S178Q; G213P; K295P; E344P; P382G; and A418P.

TABLE 2

Amino acid substitutions in C1 CBH1a variant 15 and equivalent substitutions in *H. grisea* cellobiohydrolase

| C1 CBH1a | H. grisea CBH |
|---|---|
| S30 | S31 |
| T58 | T59 |
| S79 | T80 |
| P82 | K83 |
| Q117 | Q118 |
| G155 | G156 |
| S177 | P178 |
| S212 | G213 |
| K294 | K295 |
| E343 | E344 |
| P381 | P382 |
| A417 | A418 |

In some embodiments, the present invention relates to a method of making CBH1a variants having improved thermostability and/or improved thermoactivity. In some embodiments, the method comprises:
(a) identifying a sequence that comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:2;
(b) aligning the identified sequence with the sequence of SEQ ID NO:2; and
(c) substituting one or more amino acid residues from the identified sequence, wherein the substitutions are made at one or more positions selected from Y2, K4, T22, T24, S30, T32, G39, S48, I49, T58, A64, N66, E69, S79, P82, I90, T98, T102, G116, Q117, Y118, I122, T126, G155, S177, S192, A205, N209, S212, N218, T221, A240, A241, A242, T264, Y265, T267, I273, Q286, K294, E343, P381, V394, S401, T402, W403, I405, A417, A432, G448, S452, S475, S483, T486, G490, A492, G502, Q508, P512, and L526.

In some embodiments, step (c) of the method comprises making one or more amino acid substitutions selected from Y2H, K4Q, T22H, T24F/I/K/L/N/R/V, S30P, T32M, G39R, S48W, I49V, T58I/V, A64S/T, N66C/P, E69C/D/N/T, S79P, P82K/M, I90L/V, T98L, T102H, G116T, Q117N, Y118G/H, I122V, T126V, G155P, S177P, S192A, A205C/G, N209G, S212P, N218H, T221H/Q/W, A240S, A241T, A242V, T264L, Y265W, T267K, I273P, Q286M, K294P, E343P, P381G, V394A/D/G/L/Q/S, S401D, T402G, W403F/Y, I405V, A417P, A432F, G448D, S452E, S475G, S483D/K/L, T486I/V/Y, G490F/M, A492V, G502R, Q508H/S, P512G, and L526A.

In some embodiments, the method further comprises determining whether the one or more amino acid substitutions increase the thermostability and/or thermoactivity of the cellobiohydrolase variant in comparison to secreted wild-type C1 CBH1a (SEQ ID NO:2).

Q117 Motif

As described herein, an amino acid substitution at position 117, wherein the position is numbered with reference to a wild-type C1 CBH1a pre-protein (e.g., SEQ ID NO:4), to a residue other than glutamine has been shown to be beneficial for improved thermostability in CBH1a variants. Additionally, as described below in Example 6, an amino acid substitution at the position corresponding to Q117 in SEQ ID NO:4 results in a significant increase in specific activity of the cellobiohydrolase protein. Q117 is conserved in a large number of cellobiohydrolases and it is expected that an amino acid substitution at this residue will result in increased specific activity in a broad category of cellobiohydrolases.

Thus, in one aspect, the present invention provides a method of increasing the thermostability and/or specific activity of a cellobiohydrolase of a fungal strain having sequence similarity to SEQ ID NO:2 (e.g., a cellobiohydrolase listed in Table 1), or a variant thereof, by introducing an amino acid other than glutamine at position 117, wherein the position is numbered with reference to a wild-type C1 CBH1a pre-protein (e.g., SEQ ID NO:4). In some embodiments, the amino acid other than glutamine is asparagine.

In a related aspect, the present invention provides a method for increasing the thermostability and/or specific activity of a parent cellobiohydrolase protein by (i) identifying a parent cellobiohydrolase protein comprising glutamine at a position corresponding to position 117 of a wild-type C1 CBH1a pre-protein (e.g., SEQ ID NO:4), and (ii) mutating the parent cellobiohydrolase protein so that the residue at the position corresponding to Q117 of the wild-type C1 CBH1a pre-protein (e.g., SEQ ID NO:4) is a residue other than glutamine, wherein the thermostability and/or cellobiohydrolase specific activity of the resulting mutated protein is increased relative to the parent cellobiohydrolase protein. In some embodiments, the residue other than glutamine is asparagine.

As used herein, a "parent cellobiohydrolase protein" refers to any type 1 cellobiohydrolase protein, and includes both naturally occurring cellobiohydrolases and recombinant cellobiohydrolases comprising one or more substitutions or deletions (e.g., one or more substitutions or deletions as described herein). Proteins can be identified as a type 1 cellobiohydrolase based on structure (e.g., primary structure) as well as by functional assays. In some embodiments, the parent cellobiohydrolase protein comprises at least 50% (or at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%) sequence identity to SEQ ID NO:2 and comprises a glutamine at a position corresponding to residue 117 of a wild-type C1 CBH1a pre-protein (e.g., SEQ ID NO:4). The position corresponding to residue 117 of SEQ ID NO:4 can be identified by alignment, as described herein, and/or by the presence of a glutamine-containing motif referred to as a "Q117 motif."

In some embodiments, the parent cellobiohydrolase protein comprises a Q117 motif selected from:

(a)
(SEQ ID NO: 15)
T-X1-Q-X2-N;

(b)
(SEQ ID NO: 16)
T-X3-Q-X2-N;

(c)
(SEQ ID NO: 17)
F-V-T-X3-Q-X2-N-[I/V]-G-S-R;

(d)
(SEQ ID NO: 18)
F-[V/I]-T-[K/N/Q/E/S/T]-[G/S/H]-Q-[Y/O]-[Q/S/G]-[T/K]-N-[I/V]G;

-continued (e)

(SEQ ID NO: 19)

[K/N/Q/T]-F-[I/V]-T-[K/N/Q/E/S/T]-[G/S/H]-Q-[Y/0]-[Q/S/G]-[T/K]-N-[I/V]-G-S-R;

and (f)

(SEQ ID NO: 20)

L-X4-L-[K/N/Q/T]-F-[I/V]-T-[K/N/Q/E/S/T]-[G/S/H]-Q-[Y/0]-[Q/S/G]-[T/K]-N-[I/V]-G-S-R;

wherein "Q" is glutamine at a position corresponding to residue 117 of a wild-type C1 CBH1a pre-protein (e.g., SEQ ID NO:4), "[Y/0]" means the residue is tyrosine or is absent, X1=0-2 independently selected amino acid residues, X2=2-3 independently selected amino acid residues, X3=2 residues, and X4=any residue, preferably N/S/R/K/T.

In some embodiments, the parent cellobiohydrolase protein comprises at least 50% (or at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%) sequence identity to SEQ ID NO:2, has a glutamine at a position corresponding to residue 117 of SEQ ID NO:4, and comprises a motif selected from:

(g) Q-X-S/T, wherein X denotes any amino acid except proline;

(h) Q-Y-S/T; and (i) Q-Y-T.

Substitution of asparagine for glutamine in motifs (g)-(i) introduces a consensus N-linked glycosylation site. The position corresponding to residue 117 of SEQ ID NO:4 can be identified by alignment, as described herein.

In some embodiments, the parental cellobiohydrolase protein has the sequence of a naturally occurring fungal protein. In some embodiments, the naturally occurring protein is from a *Thielavia; Humicola; Chaetomium; Neurospora; Chaetomidium; Botryosphaeria; Trichophaea; Aspergillus; Schizophyllum; Sporotrichium; Corynascus; Myceliophthora; Acremonium; Sordaria; Thermoascus*; or *Agaricus* species. In some embodiments the parental cellobiohydrolase protein is a recombinant protein. For example, cellobiohydrolase variant modified to provide desirable characteristics can be further modified to increase specific activity.

Having identified a target cellobiohydrolase, routine methods (including but not limited to methods described herein) can be used to introduce substitutions and express, and optionally purify, the mutated protein.

In some embodiments, the residue which is substituted for glutamine is asparagine. In some embodiments, the residue which is substituted for glutamine is not serine. In some embodiments, the residue which is substituted for glutamine is not proline. In some embodiments, the residue which is substituted for glutamine is not alanine. In some embodiments, the residue which is substituted for glutamine is not glutamine. In some embodiments, the residue which is substituted for glutamine is not aspartic acid. In some embodiments, the residue which is substituted for glutamine is not leucine. In some embodiments, the residue which is substituted for glutamine is not lysine.

Also provided are recombinant variant cellobiohydrolase proteins produced according to the methods above and cells expressing such proteins. In some embodiments the parent cellobiohydrolase protein is derived from a cell-type different from the cell expressing the variant cellobiohydrolase. Also provided are compositions containing recombinant, isolated, purified or partially purified cellobiohydrolases produced according to the methods above in combination with one or more other cellulases (including cellulases from another fungal species, or variants thereof).

In some embodiments, the variant has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a wild-type C1 CBH1a pre-protein (e.g., SEQ ID NO:4). In some embodiments, the variant comprises at least one motif selected from motifs a-f, above, and contains asparagine at the position corresponding to position 117 of SEQ ID NO:4.

V. Generation of Cellobiohydrolase Variants

A cellobiohydrolase variant polypeptide of the invention can be subject to further modification to generate new polypeptides that retain the specific substitutions that characterize the variant and which may have desirable properties. For example, a polynucleotide encoding a cellobiohydrolase with an improved property can be subjected to additional rounds of mutagenesis treatments to generate polypeptides with further improvements in the desired enzyme or enzyme properties.

Given the wild-type C1 CBH1a sequence or the sequence of a wild-type fungal homolog of C1 CBH1a, cellobiohydrolase variants can be generated according to the methods described herein and can be screened for the presence of improved properties, such as increased thermostability or increased thermoactivity. Libraries of cellobiohydrolase variant polypeptides and/or polynucleotides encoding the variants may be generated from a parental sequence (e.g., wild-type C1 CBH1a, or a wild-type cellobiohydrolase from another fungal strain such as a cellobiohydrolase of Table 1, or one of the cellobiohydrolase variants exemplified herein), and screened using a high throughput screen to determine improved properties such as increased activity or stability at desired conditions, as described herein. Mutagenesis and directed evolution methods are well known in the art and can be readily applied to polynucleotides encoding cellobiohydrolase variants exemplified herein to generate variant libraries that can be expressed, screened, and assayed using the methods described herein. See, e.g., Ling, et al., 1999, "Approaches to DNA mutagenesis: an overview," *Anal. Biochem.,* 254(2):157-78; Dale, et al., 1996, "Oligonucleotide-directed random mutagenesis using the phosphorothioate method," *Methods Mol. Biol.,* 57:369-74; Smith, 1985, "In vitro mutagenesis," *Ann. Rev. Genet.,* 19:423-462; Botstein, et al., 1985, "Strategies and applications of in vitro mutagenesis," *Science,* 229:1193-1201; Carter, 1986, "Site-directed mutagenesis," *Biochem. J.,* 237:1-7; Kramer, et al., 1984, "Point Mismatch Repair," Cell, 38:879-887; Wells, et al., 1985, "Cassette mutagenesis: an efficient method for generation of multiple mutations at defined sites," *Gene,* 34:315-323; Minshull, et al., 1999, "Protein evolution by molecular breeding," *Current Opinion in Chemical Biology,* 3:284-290; Christians, et al., 1999, "Directed evolution of thymidine kinase for AZT phosphorylation using DNA family shuffling," *Nature Biotechnology,* 17:259-264; Crameri, et al., 1998, "DNA shuffling of a family of genes from diverse species accelerates directed evolution," *Nature,* 391:288-291; Crameri, et al., 1997, "Molecular evolution of an arsenate detoxification pathway by DNA shuffling," *Nature Biotechnology,* 15:436-438; Zhang, et al., 1997 "Directed evolution of an effective fucosidase from a galactosidase by DNA shuffling and screening," *Proceedings of the National Academy of Sciences, U.S.A.,* 94:45-4-4509; Crameri, et al., 1996, "Improved green fluorescent protein by molecular evolution using DNA shuffling," *Nature Biotechnology,* 14:315-319; Stemmer, 1994, "Rapid evolution of a protein in vitro by DNA shuffling," *Nature,* 370:389-391; Stemmer, 1994, "DNA shuffling by random fragmentation and reassembly: In vitro recombination for molecular evolution," *Proceedings of the National Academy of Sciences, U.S.A.,* 91:10747-10751; WO 95/22625; WO 97/0078; WO 97/35966; WO 98/27230; WO 00/42651; and WO 01/75767, all of which are incorporated herein by reference.

Cellobiohydrolase variants having the amino acid substitutions described herein can also be synthetically generated. Chemically synthesized polypeptides may be generated using the well-known techniques of solid phase, liquid phase, or peptide condensation techniques, and can include any combination of amino acids as desired to produce the variants described herein. Synthetic amino acids can be obtained from Sigma, Cambridge Research Biochemical, or any other chemical company familiar to those skilled in the art.

In generating variants that comprise substitutions, insertions or deletions at positions in addition to those described supra, the ordinarily skilled practitioner will be aware that certain regions of the cellobiohydrolase protein are less tolerant than others to substitutions (especially non-conservative substitutions). Thus, in some embodiments, variant cellobiohydrolase polypeptides retain conserved residues and functional domains from the parent.

VI. Cellobiohydrolase Thermoactivity and Thermostability

Cellobiohydrolase activity and thermostability can be determined by methods described in the Examples section (e.g., Examples 3, 4, and 7), and/or using any other methods known in the art. Cellobiohydrolase activity may be determined, for example, using an assay that measures the conversion of crystalline cellulose to glucose, or using a 4-methylumbelliferyl β-D-lactopyranoside (MUL) assay.

For example, cellobiohydrolase activity can be determined using a cellulose assay, in which the ability of the cellobiohydrolase variants to hydrolyze a cellulose substrate to cellobiose, e.g., crystalline cellulose, phosphoric acid-swollen cellulose (PASC), or pretreated feedstock under specific temperature and/or pH conditions is measured, then a β-glucosidase is added to convert the cellobiose to glucose. In one exemplary assay, biotransformation reactions are performed by mixing 60 μl clear supernatant with 40 μl of a slurry of crystalline cellulose in 340 mM sodium acetate buffer pH 4.2-5.0 (final concentration: 200 g/L crystalline cellulose; a glass bead/well). Additionally, 50 μl of beta-glucosidase supernatant is added to the reaction mixture for the conversion of cellobiose to glucose. Biotransformation is performed at pH 4-5, 65-70° C. for an appropriate amount of time. Conversion of crystalline cellulose to fermentable sugar oligomers (e.g., glucose) can be determined by art-known means, including but not limited to coupled enzymatic assay and colorimetric assay. For example, glucose concentrations can be determined using a coupled enzymatic assay based on glucose oxidase and horseradish peroxidase (e.g., GOPOD assay) as exemplified in Trinder, P. (1969) *Ann. Clin. Biochem.* 6:24-27, which is incorporated herein by reference in its entirety. GOPOD assay kits are known in the art and are readily commercially available, e.g., from Megazyme (Wicklow, Ireland). Methods for performing GOPOD assays are known in the art; see, e.g., McCleary et al., *J. AOAC Int.* 85(5):1103-11 (2002), the contents of which are incorporated by reference herein. For the GOPOD assay, fermentable sugar oligomer (e.g., glucose) production is measured by mixing 10 μl of the above reaction with 190 μl of GOPOD assay mix. The reactions are allowed to shake for 30 min at room temperature. Absorbance of the solution is measured at 510 nm to determine the amount of glucose produced in the original biotransformation reaction. The amount of glucose produced is measured at 510 nm to calculate cellobiohydrolase activity. Additional methods of cellobiose quantification include chromatographic methods, for example by HPLC as exemplified in the incorporated materials of U.S. Pat. Nos. 6,090, 595 and 7,419,809.

Cellobiohydrolase thermostability can be determined, for example, by exposing the cellobiohydrolase variants and the reference (e.g., wild-type) cellobiohydrolase to stress conditions of elevated temperature, optionally under low pH for a desired period of time and then determining residual cellobiohydrolase activity using an assay that measures the conversion of cellulose to glucose. In an exemplary assay, thermostability is screened using a cellulose-based High Throughput Assay. In deep, 96-well microtiter plates 75 μL of media supernatant containing cellobiohydrolase variant is added to 75 g/L crystalline cellulose in 250 mM sodium acetate buffer pH 4.5 containing β-glucosidase. After sealing with aluminum/polypropylene laminate heat seal tape (Velocity 11 (Menlo Park, Calif.), Cat# 06643-001)), the reactions are incubated at 50° C. for 24 hr while shaking at 950 rpm. Conversion of crystalline cellulose to fermentable sugar is measured by any art-known means, for example using any of the assays as described above, such as coupled enzymatic assay based on glucose oxidase and horseradish peroxidase or GOPOD assay. For example, from each of these reactions, 5 μl is transferred to 195 μl of GOPOD assay mix. The reactions are allowed to shake for 30 min at room temperature. Absorbance of the solution is measured at 510 nm to determine the amount of glucose produced in the original biotransformation reaction. The amount of glucose produced is measured at 510 nm to calculate cellobiohydrolase activity.

Some cellobiohydrolase variants of the present invention will have improved thermoactivity or thermostability as compared to a reference sequence. In some embodiments, a cellobiohydrolase variant has improved thermostability or improved thermoactivity at a pH range of 3.0 to 7.5, at a pH range of 3.5 to 6.5, at a pH range of 3.5 to 6.0, at a pH range of 3.5 to 5.5, at a pH range of 3.5 to 5.0, or at a pH range of 4.0 to 5.0. In some embodiments, a cellobiohydrolase variant has improved thermostability or improved thermoactivity at a temperature of about 55° C. to 80° C., at a temperature of about 60° C. to 80° C., at a temperature of about 65° C. to 80° C., or at a temperature of about 65 to 75° C. In some embodiments, a cellobiohydrolase will have improved thermostability or improved thermoactivity at a pH of 3.5 to 5.0 and a temperature of 65-80° C.

In some embodiments, the cellobiohydrolase variants of the invention exhibit cellobiohydrolase activity that is at least about 1.0 fold or greater than the cellobiohydrolase activity of a control cellobiohydrolase (e.g., the secreted wild-type CBH1a of SEQ ID NO:2) when tested under the same conditions. In some embodiments, the thermostability of the cellobiohydrolase variants at pH 4.4 and 66° C. is at least about 1.0 fold or greater than the thermostability of a control cellobiohydrolase (e.g., the secreted wild-type CBH1a of SEQ ID NO:2) under the same conditions.

VII. Fusion Peptides and Additional Sequence Elements

In some embodiments, a cellobiohydrolase variant of the present invention further comprises additional sequences which do not alter the encoded activity of the cellobiohydrolase. For example, the cellobiohydrolase may be linked to an epitope tag or to another sequence useful in purification.

The present invention also provides cellobiohydrolase variant fusion polypeptides, wherein the fusion polypeptide comprises an amino acid sequence encoding a cellobiohydrolase variant polypeptide of the present invention or fragment thereof, linked either directly or indirectly through the N- or C-terminus of the cellobiohydrolase variant polypeptide to an amino acid sequence encoding at least a second (additional) polypeptide. The cellobiohydrolase variant fusion polypeptide may further include amino acid sequence encoding a third, fourth, fifth, or additional polypeptides. Typically, each additional polypeptide has a biological activity, or alternatively, is a portion of a polypeptide that has a biological activity, where the portion has the effect of improving expression and/or secretion and/or purification and/or detection of the fusion polypeptide from the desired expression host. These sequences may be fused, either directly or indirectly, to the N- or C-terminus of the cellobiohydrolase variant polypeptide or fragment thereof, or alternatively, to the N- or C-terminus of the additional polypeptides having biological activity.

In some embodiments, the additional polypeptide(s) encode an enzyme or active fragment thereof, and/or a polypeptide that improves expression and/or secretion of the fusion polypeptide from the desired expression host cell. For example, the additional polypeptide may encode a cellulase (for example, a cellobiohydrolase having a different amino acid sequence from the cellobiohydrolase variant polypeptide in the fusion polypeptide, or a polypeptide exhibiting endoglucanase activity or β-glucosidase activity) and/or a polypeptide that improves expression and secretion from the desired host cell, such as, for example, a polypeptide that is normally expressed and secreted from the desired expression host, such as a secreted polypeptide normally expressed from filamentous fungi. These include glucoamylase, α-amylase and aspartyl proteases from *Aspergillus niger, Aspergillus niger* var. *awamori*, and *Aspergillus oryzae*, cellobiohydrolase I, cellobiohydrolase II, endoglucanase I and endoglucase III from *Trichoderma* and glucoamylase from *Neurospora* and *Humicola* species. See WO 98/31821, which is incorporated herein by reference.

The polypeptide components of the fusion polypeptide may be linked to each other indirectly via a linker. Linkers suitable for use in the practice of the present invention are described in WO 2007/075899, which is incorporated herein by reference. Exemplary linkers include peptide linkers of from 1 to about 40 amino acid residues in length, including those from about 1 to about 20 amino acid residues in length, and those from about 1 to about 10 amino acid residues in length. In some embodiments, the linkers may be made up of a single amino acid residue, such as, for example, a Gly, Ser, Ala, or Thr residue or combinations thereof, particularly Gly and Ser. Linkers employed in the practice of the present invention may be cleavable. Suitable cleavable linkers may contain a cleavage site, such as a protease recognition site. Exemplary protease recognition sites are well known in the art and include, for example, Lys-Arg (the KEX2 protease recognition site, which can be cleaved by a native *Aspergillus* KEX2-like protease), Lys and Arg (the trypsin protease recognition sites). See, for example, WO 2007/075899, which is incorporated herein by reference.

Signal Peptides

In some embodiments, the cellobiohydrolase variant polypeptides of the present invention are secreted from the host cell in which they are expressed (e.g., a yeast or fungal cell) and are expressed as a pre-protein including a signal peptide, i.e., an amino acid sequence linked to the amino terminus of a polypeptide and which directs the encoded polypeptide into the cell secretory pathway. In one embodiment, the signal peptide is an endogenous C1 cellobiohydrolase signal peptide, e.g., the signal peptide of the CBH1a of SEQ ID NO:4 having the sequence MYAKFATLAALVAGAAA (SEQ ID NO:3). In other embodiments, signal peptides from other C1 secreted proteins are used.

Still other signal peptides may be used, depending on the host cell and other factors. Effective signal peptide coding regions for filamentous fungal host cells include, but are not limited to, the signal peptide coding regions obtained from *Aspergillus oryzae* TAKA amylase, *Aspergillus niger* neutral amylase, *Aspergillus niger* glucoamylase, *Rhizomucor miehei* asparatic proteinase, *Humicola insolens* cellulase, *Humicola lanuginosa* lipase, and *T. reesei* cellobiohydrolase II (TrCBH2).

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* β-lactamase, *Bacillus stearothermophilus* neutral proteases (nprT, nprS, nprM), and *Bacillus subtilis* prsA. Further signal peptides are described by Simonen and Palva, 1993, *Microbiol Rev* 57: 109-137 (incorporated herein by reference).

Useful signal peptides for yeast host cells also include those from the genes for *Saccharomyces cerevisiae* alpha-factor, *Saccharomyces cerevisiae* SUC2 invertase (see Taussig and Carlson, 1983, *Nucleic Acids Res* 11:1943-54; SwissProt Accession No. P00724), and others. See, e.g., Romanos et al., 1992, *Yeast* 8:423-488. Variants of these signal peptides and other signal peptides are suitable.

Cellulose Binding Domains

Cellobiohydrolases and other cellulases generally have a multidomain structure comprising a catalytic domain (CD) and a cellulose binding domain (CBD) joined by a linker peptide. For example, the CBH1a of SEQ ID NO:2 comprises a CBD at amino acids 474-509 and a CD at amino acids 1-437. In some embodiments, a cellobiohydrolase variant of the present invention lacks a CBD. For example, in some embodiments the CBD of the cellobiohydrolase is cleaved from the catalytic domain following secretion of the enzyme. Alternatively, engineered cellobiohydrolases lacking a CBD may be used.

CBDs may be homologous or heterologous to the catalytic domain. A homologous CBD is associated in the wild-type cellobiohydrolase with the parental catalytic domain. For example, the C1 CBH1a CBD is homologous to the C1 CBH1a catalytic domain. In some embodiments, a cellobiohydrolase variant of the present invention has multiple CBDs. The multiple CBDs can be in tandem or in different regions of the polypeptide.

VIII. Polynucleotides and Expression Systems Encoding Cellobiohydrolase Type 1 Variants In another aspect, the present invention provides polynucleotides encoding the variant cellobiohydrolase polypeptides as described herein. The polynucleotide may be operably linked to one or more heterologous regulatory or control sequences that control gene expression to create a recombinant polynucleotide capable of expressing the polypeptide. Expression constructs containing a heterologous polynucleotide encoding the engineered cellobiohydrolase can be introduced into appropriate host cells to express the cellobiohydrolase.

In some embodiments, the cellobiohydrolase variant is generated from a wild-type cellobiohydrolase cDNA sequence (e.g., a wild-type C1 CBH1a cDNA sequence (SEQ ID NO:1), or a cDNA sequence encoding a wild-type protein of Table 1) or the portion thereof comprising the open reading frame, with changes made as required at the codons corresponding to substitutions (residues mutated relative to the wild-type sequence as described herein, for example at any of Tables 2-7). In addition, one or more "silent" nucleotide changes can be incorporated. These changes may affect cellobiohydrolase activity in a variety of ways. For example, without intending to be bound by a particular mechanism, silent mutations may increase the stability of mRNAs encoding the variant protein.

In other embodiments, non-naturally occurring sequences are preferred. Those having ordinary skill in the art will understand that due to the degeneracy of the genetic code, a multitude of nucleotide sequences encoding cellobiohydrolase polypeptides of the present invention exist. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence. The invention contemplates and provides each and every possible variation of nucleic acid sequence encoding a polypeptide of the invention that could be made by selecting combinations based on possible codon choices.

A DNA sequence may also be designed for high codon usage bias codons (codons that are used at higher frequency in the protein coding regions than other codons that code for the same amino acid). The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. A codon whose frequency increases with the level of gene expression is typically an optimal codon for expression. In particular, a DNA sequence can be optimized for expression in a particular host organism. References providing preference information for a wide range of organisms are readily available See e.g., Henaut and Danchin in "*Escherichia coli* and *Salmonella*," Neidhardt, et al. Eds., ASM Pres, Washington D.C. (1996), pp. 2047-2066, which is incorporated herein by reference.

A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; Codon W, John Peden, University of Nottingham; McInerney, J. O, 1998, *Bioinformatics* 14:372-73; Stenico et al., 1994, *Nucleic Acids Res.* 222437-46; Wright, F., 1990, *Gene* 87:23-29; Wada et al., 1992, *Nucleic Acids Res.* 20:2111-2118; Nakamura et al., 2000, *Nucl. Acids Res.* 28:292; Henaut and Danchin, "*Escherichia coli* and *Salmonella*," 1996, Neidhardt, et al. Eds., ASM Press, Washington D.C., p. 2047-2066, all of which are incorporated herein be reference). The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTs), or predicted coding regions of genomic sequences (see for example, Mount, D., *Bioinformatics: Sequence and Genome Analysis*, Chapter 8, Cold Spring Harbor Laboratory Press, Cold Spring Harbor, N.Y., 2001; Uberbacher, E. C., 1996, *Methods Enzymol.* 266: 259-281; Tiwari et al., 1997, *Comput. Appl. Biosci.* 13:263-270, all of which are incorporated herein by reference).

Polynucleotides encoding cellobiohydrolases can be prepared using methods that are well known in the art. Typically, oligonucleotides of up to about 40 bases are individually synthesized, then joined (e.g., by enzymatic or chemical ligation methods, or polymerase-mediated methods) to form essentially any desired continuous sequence. For example, polynucleotides of the present invention can be prepared by chemical synthesis using, for example, the classical phosphoramidite method described by Beaucage, et al., 1981, *Tetrahedron Letters,* 22:1859-69, or the method described by Matthes, et al., 1984, *EMBO J.* 3:801-05, both of which are incorporated herein by reference. These methods are typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company (Midland, Tex.), The Great American Gene Company (Ramona, Calif.), ExpressGen Inc. (Chicago, Ill.), Operon Technologies Inc. (Alameda, Calif.), and many others.

Polynucleotides may also be synthesized by well-known techniques as described in the technical literature. See, e.g., Carruthers, et al., 1982, *Cold Spring Harbor Symp. Quant. Biol.,* 47:411-18 and Adams et al., 1983, *J. Am. Chem. Soc.* 105:661, both of which are incorporated herein by reference. Double stranded DNA fragments may then be obtained either by synthesizing the complementary strand and annealing the strands together under appropriate conditions, or by adding the complementary strand using DNA polymerase with an appropriate primer sequence.

General texts that describe molecular biological techniques which are useful herein, including the use of vectors, promoters, protocols sufficient to direct persons of skill through in vitro amplification methods, including the polymerase chain reaction (PCR) and the ligase chain reaction (LCR), and many other relevant methods, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2009) ("Ausubel"), all of which are incorporated herein by reference. Reference is made to Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research*

(1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomeli et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564, all of which are incorporated herein by reference. Methods for cloning in vitro amplified nucleic acids are described in Wallace et al., U.S. Pat. No. 5,426,039, which is incorporated herein by reference.

Vectors

The present invention makes use of recombinant constructs comprising a sequence encoding a cellobiohydrolase as described above. In a particular aspect the present invention provides an expression vector comprising a cellobiohydrolase polynucleotide operably linked to a heterologous promoter. Expression vectors of the present invention may be used to transform an appropriate host cell to permit the host to express the cellobiohydrolase protein. Methods for recombinant expression of proteins in fungi and other organisms are well known in the art, and a number expression vectors are available or can be constructed using routine methods. See, e.g., Tkacz and Lange, 2004, Advances in fungal biotechnology for industry, agriculture, and medicine, Kluwer academic/Plenum Publishers. New York; Zhu et al., 2009, Construction of two Gateway vectors for gene expression in fungi *Plasmid* 6:128-33; Kavanagh, K. 2005, Fungi: biology and applications Wiley, all of which are incorporated herein by reference.

Nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted. Polynucleotides of the present invention can be incorporated into any one of a variety of expression vectors suitable for expressing a polypeptide. Suitable vectors include chromosomal, non-chromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces genetic material into a cell, and, if replication is desired, which is replicable and viable in the relevant host can be used.

In some embodiments, the construct further comprises regulatory sequences, including, for example, a promoter, operably linked to the protein encoding sequence. Large numbers of suitable vectors and promoters are known to those of skill in the art.

Promoters

In order to obtain high levels of expression in a particular host it is often useful to express the cellobiohydrolase variant of the present invention under the control of a heterologous promoter. A promoter sequence may be operably linked to the 5' region of the cellobiohydrolase coding sequence using routine methods.

Examples of useful promoters for expression of cellobiohydrolases include promoters from fungi. In some embodiments, a promoter sequence that drives expression of a gene other than a cellobiohydrolase gene in a fungal strain may be used. As a non-limiting example, a fungal promoter from a gene encoding an endoglucanase may be used. In some embodiments, a promoter sequence that drives the expression of a cellobiohydrolase gene in a fungal strain other than the fungal strain from which the cellobiohydrolase variant was derived may be used. As a non-limiting example, if the cellobiohydrolase variant is derived from C1, a promoter from a *T. reesei* cellobiohydrolase gene may be used or a promoter as described in WO2010107303, such as but not limited to the sequences identified as SEQ ID NO:25, SEQ ID NO:26, SEQ ID NO:27, SEQ ID NO:28, or SEQ ID NO:29 in WO2010107303.

Examples of other suitable promoters useful for directing the transcription of the nucleotide constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787, which is incorporated herein by reference), as well as the NA2-tpi promoter (a hybrid of the promoters from the genes for *Aspergillus niger* neutral alpha-amylase and *Aspergillus oryzae* triose phosphate isomerase), promoters such as cbh1, cbh2, egl1, egl2, pepA, hfb1, hfb2, xyn1, amy, and glaA (Nunberg et al., 1984, *Mol. Cell Biol.*, 4:2306-2315, Boel et al., 1984, *EMBO J.* 3:1581-85 and EPA 137280, all of which are incorporated herein by reference), and mutant, truncated, and hybrid promoters thereof. In a yeast host, useful promoters can be from the genes for *Saccharomyces cerevisiae* enolase (eno-1), *Saccharomyces cerevisiae* galactokinase (gall), *Saccharomyces cerevisiae* alcohol dehydrogenase/glyceraldehyde-3-phosphate dehydrogenase (ADH2/GAP), and *S. cerevisiae* 3-phosphoglycerate kinase. Other useful promoters for yeast host cells are described by Romanos et al., 1992, *Yeast* 8:423-488, incorporated herein by reference. Promoters associated with chitinase production in fungi may be used. See, e.g., Blaiseau and Lafay, 1992, *Gene* 120243-248 (filamentous fungus *Aphanocladium album*); Limon et al., 1995, *Curr. Genet*, 28:478-83 (*Trichoderma harzianum*), both of which are incorporated herein by reference.

Promoters known to control expression of genes in prokaryotic or eukaryotic cells or their viruses and which can be used in some embodiments of the invention include SV40 promoter, *E. coli* lac or trp promoter, phage lambda $P_L$ promoter, tac promoter, T7 promoter, and the like. In bacterial host cells, suitable promoters include the promoters obtained from the *E. coli* lac operon, *Streptomyces coelicolor* agarase gene (dagA), *Bacillus subtilis* levansucranse gene (sacB), *Bacillus licheniformis* α-amylase gene (amyl), *Bacillus stearothermophilus* maltogenic amylase gene (amyM), *Bacillus amyloliquefaciens* α-amylase gene (amyQ), *Bacillus subtilis* xylA and xylB genes and prokaryotic β-lactamase gene.

Any other promoter sequence that drives expression in a suitable host cell may be used. Suitable promoter sequences can be identified using well known methods. In one approach, a putative promoter sequence is linked 5' to a sequence encoding a reporter protein, the construct is transfected into the host cell (e.g., C1) and the level of expression of the reporter is measured. Expression of the reporter can be determined by measuring, for example, mRNA levels of the reporter sequence, an enzymatic activity of the reporter protein, or the amount of reporter protein produced. For example, promoter activity may be determined by using the green fluorescent protein as coding sequence (Henriksen et al, 1999, *Microbiology* 145:729-34, incorporated herein by reference) or a lacZ reporter gene (Punt et al, 1997, *Gene*, 197:189-93, incorporated herein by reference). Functional promoters may be derived from naturally occurring promoter sequences by directed evolution methods. See, e.g. Wright et al., 2005, *Human Gene Therapy,* 16:881-892, incorporated herein by reference.

Other Expression Elements

Cloned cellobiohydrolases may also have a suitable transcription terminator sequence, a sequence recognized by a host cell to terminate transcription. The terminator sequence is operably linked to the 3' terminus of the nucleic acid sequence encoding the polypeptide. Any terminator that is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary transcription terminators are described in U.S. Pat. No. 7,399,627, incorporated herein by reference.

Exemplary terminators for yeast host cells can be obtained from the genes for *Saccharomyces cerevisiae* enolase, *Saccharomyces cerevisiae* cytochrome C (CYCI), and *Saccharomyces cerevisiae* glyceraldehyde-3-phosphate dehydrogenase. Other useful terminators for yeast host cells are described by Romanos et al., 1992, *Yeast* 8:423-88.

A suitable leader sequence may be part of a cloned cellobiohydrolase sequence, which is a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

Sequences may also contain a polyadenylation sequence, which is a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, *Mol Cell Bio* 15:5983-5990 (1995).

The expression vector of the present invention optionally contains one or more selectable markers, which permit easy selection of transformed cells. A selectable marker is a gene, the product of which provides for biocide or viral resistance, resistance to heavy metals, prototrophy to auxotrophs, and the like. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*. Suitable markers for yeast host cells are ADE2, HIS3, LEU2, LYS2, MET3, TRP1, and URA3.

IX. Host Cells Comprising Cellobiohydrolase Type 1 Variants

A vector comprising a sequence encoding a cellobiohydrolase is transformed into a host cell in order to allow propagation of the vector and expression of the cellobiohydrolase. In some embodiments, the cellobiohydrolase is post-translationally modified to remove the signal peptide and in some cases may be cleaved after secretion.

The transformed or transfected host cell described above is cultured in a suitable nutrient medium under conditions permitting the expression of the cellobiohydrolase. The medium used to culture the cells may be any conventional medium suitable for growing the host cells, such as minimal or complex media containing appropriate supplements. Cells are optionally grown in HTP media. Suitable media are available from commercial suppliers or may be prepared according to published recipes (e.g. in catalogues of the American Type Culture Collection).

Expression Hosts

In some embodiments, the host cell is a eukaryotic cell. Suitable eukaryotic host cells include, but are not limited to, fungal cells, algal cells, insect cells, and plant cells. Suitable fungal host cells include, but are not limited to, Ascomycota, Basidiomycota, Deuteromycota, Zygomycota, Fungi imperfecti. Particularly preferred fungal host cells are yeast cells and filamentous fungal cells. The filamentous fungal host cells of the present invention include all filamentous forms of the subdivision Eumycotina and Oomycota. (Hawksworth et al., In Ainsworth and Bisby's Dictionary of The Fungi, $8^{th}$ edition, 1995, CAB International, University Press, Cambridge, UK). Filamentous fungi are characterized by a vegetative mycelium with a cell wall composed of chitin, cellulose and other complex polysaccharides. The filamentous fungal host cells of the present invention are morphologically distinct from yeast.

In the present invention a filamentous fungal host cell may be a cell of a species of, but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, or teleomorphs, or anamorphs, and synonyms, basionyms, or taxonomic equivalents thereof.

In some embodiments of the invention, the filamentous fungal host cell is of the *Trichoderma* species, e.g., *T. longibrachiatum, T. viride* (e.g., ATCC 32098 and 32086), *Hypocrea jecorina* or *T. reesei* (NRRL 15709, ATTC 13631, 56764, 56765, 56466, 56767 and RL-P37 and derivatives thereof; see Sheir-Neiss et al., Appl. Microbiol. Biotechnology, 20 (1984) pp 46-53), *T. koningii*, and *T. harzianum*. In addition, the term "*Trichoderma*" refers to any fungal strain that was previously classified as *Trichoderma* or currently classified as *Trichoderma*. In some embodiments of the invention, the filamentous fungal host cell is of the *Aspergillus* species, e.g., *A. awamori, A. funigatus, A. japonicus, A. nidulans, A. niger, A. aculeatus, A. foetidus, A. oryzae, A.*

*sojae*, and *A. kawachi*. (Reference is made to Kelly and Hynes (1985) *EMBO J.* 4,475479; NRRL 3112, ATCC 11490, 22342, 44733, and 14331; Yelton M., et al., (1984) *Proc. Natl. Acad. Sci. USA,* 81, 1470-1474; Tilburn et al., (1982) *Gene* 26, 205-221; and Johnston, I. L. et al. (1985) *EMBO J.* 4, 1307-1311). In some embodiments of the invention, the filamentous fungal host cell is of the *Chrysosporium* species, e.g., *C. lucknowense, C. keratinophilum, C. tropicum, C. merdarium, C. inops, C. pannicola*, and *C. zonatum*. In some embodiments of the invention, the filamentous fungal host cell is of the *Myceliophthora* species, e.g., *M. thermophilia*. In some embodiments of the invention, the filamentous fungal host cell is of the *Fusarium* species, e.g., *F. bactridioides, F. cerealis, F. crookwellense, F. culmorum, F. graminearum, F. graminum. F. oxysporum, F. roseum*, and *F. venenatum*. In some embodiments of the invention, the filamentous fungal host cell is of the *Neurospora* species, e.g., *N. crassa*. Reference is made to Case, M. E. et al., (1979) *Proc. Natl. Acad. Sci*. USA, 76, 5259-5263; U.S. Pat. No. 4,486,553; and Kinsey, J. A. and J. A. Rambosek (1984) *Molecular and Cellular Biology* 4, 117-122. In some embodiments of the invention, the filamentous fungal host cell is of the *Humicola* species, e.g., *H. insolens, H. grisea*, and *H. lanuginosa*. In some embodiments of the invention, the filamentous fungal host cell is of the *Mucor* species, e.g., *M. miehei* and *M. circinelloides*. In some embodiments of the invention, the filamentous fungal host cell is of the *Rhizopus* species, e.g., *R. oryzae* and *R. niveus*. In some embodiments of the invention, the filamentous fungal host cell is of the *Penicillum* species, e.g., *P. purpurogenum, P. chrysogenum*, and *P. verruculosum*. In some embodiments of the invention, the filamentous fungal host cell is of the *Thielavia* species, e.g., *T. terrestris* and *T. heterothallica*. In some embodiments of the invention, the filamentous fungal host cell is of the *Tolypocladium* species, e.g., *T. inflatum* and *T. geodes*. In some embodiments of the invention, the filamentous fungal host cell is of the *Trametes* species, e.g., *T. villosa* and *T. versicolor*. In some embodiments of the invention, the filamentous fungal host cell is of the *Sporotrichium* species In some embodiments of the invention, the filamentous fungal host cell is of the *Corynascus* species.

In the present invention a yeast host cell may be a cell of a species of, but not limited to *Candida, Hansenula, Saccharomyces, Schizosaccharomyces, Pichia, Kluyveromyces*, and *Yarrowia*. In some embodiments of the invention, the yeast cell is *Hansenula polymorpha, Saccharomyces cerevisiae, Saccaromyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, and *Yarrowia lipolytica.*

In some embodiments of the invention, the host cell is an algal cell such as *Chlamydomonas* (e.g., *C. Reinhardtii*) and *Phormidium* (P. sp. ATCC29409).

In other embodiments, the host cell is a prokaryotic cell. Suitable prokaryotic cells include gram positive, gram negative and gram-variable bacterial cells. For example and not for limitation, the host cell may be a species of *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia* and *Zymomonas*. In some embodiments, the host cell is a species of, *Agrobacterium, Acinetobacter, Azobacter, Bacillus, Bifidobacterium, Buchnera, Geobacillus, Campylobacter, Clostridium, Corynebacterium, Escherichia, Enterococcus, Erwinia, Flavobacterium, Lactobacillus, Lactococcus, Pantoea, Pseudomonas, Staphylococcus, Salmonella, Streptococcus, Streptomyces*, and *Zymomonas.*

In yet other embodiments, the bacterial host strain is non-pathogenic to humans. In some embodiments the bacterial host strain is an industrial strain. Numerous bacterial industrial strains are known and suitable in the present invention.

In some embodiments of the invention, the bacterial host cell is of the *Agrobacterium* species, e.g., *A. radiobacter, A. rhizogenes*, and *A. rubi*. In some embodiments of the invention the bacterial host cell is of the *Arthrobacter* species, e.g., *A. aurescens, A. citreus, A. globformis, A. hydrocarboglutamicus, A. mysorens, A. nicotianae, A. paraffineus, A. protophonniae, A. roseoparqffinus, A. sulfureus*, and *A. ureafaciens*. In some embodiments of the invention the bacterial host cell is of the *Bacillus* species, e.g., *B. thuringensis, B. anthracis, B. megaterium, B. subtilis, B. lentus, B. circulans, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell will be an industrial *Bacillus* strain including but not limited to *B. subtilis, B. pumilus, B. licheniformis, B. megaterium, B. clausii, B. stearothermophilus* and *B. amyloliquefaciens*. Some preferred embodiments of a *Bacillus* host cell include *B. subtilis, B. licheniformis, B. megaterium, B. stearothermophilus* and *B. amyloliquefaciens*. In some embodiments the bacterial host cell is of the *Clostridium* species, e.g., *C. acetobutylicum, C. tetani* E88, *C. lituseburense, C. saccharobutylicum, C. perfringens*, and *C. beijerinckii*. In some embodiments the bacterial host cell is of the *Corynebacterium* species e.g., *C. glutamicum* and *C. acetoacidophilum*. In some embodiments the bacterial host cell is of the *Escherichia* species, e.g., *E. coli*. In some embodiments the bacterial host cell is of the *Erwinia* species, e.g., *E. uredovora, E. carotovora, E. ananas, E. herbicola, E. punctata*, and *E. terreus*. In some embodiments the bacterial host cell is of the *Pantoea* species, e.g., *P. citrea*, and *P. agglomerans*. In some embodiments the bacterial host cell is of the *Pseudomonas* species, e.g., *P. putida, P. aeruginosa, P. mevalonii*, and P. sp. D-01 10. In some embodiments the bacterial host cell is of the *Streptococcus* species, e.g., *S. equisimiles, S. pyogenes*, and *S. uberis*. In some embodiments the bacterial host cell is of the *Streptomyces* species, e.g., *S. ambofaciens, S. achromogenes, S. avermitilis, S. coelicolor, S. aureofaciens, S. aureus, S. fungicidicus, S. griseus*, and *S. lividans*. In some embodiments the bacterial host cell is of the *Zymomonas* species, e.g., *Z. mobilis*, and *Z. lipolytica.*

Strains which may be used in the practice of the invention including both prokaryotic and eukaryotic strains, are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Host cells may be genetically modified to have characteristics that improve protein secretion, protein stability or other properties desirable for expression and/or secretion of a protein. For example, knockout of Alp1 function results in a cell that is protease deficient. Knockout of pyr5 function results in a cell with a pyrimidine deficient phenotype. In particular embodiments host cells are modified to delete endogenous cellulase protein-encoding sequences or otherwise eliminate expression of one or more endogenous cellulases. In one embodiment expression of one or more endogenous cellulases is inhibited to increase production of cellulases of interest. Genetic modification can be achieved by genetic engineering techniques or using classical microbiological techniques, such as chemical or UV mutagenesis and subsequent selection. A combination of recombinant modification and classical selection techniques may be used to produce the organism of interest. Using recombinant technology, nucleic acid molecules can be introduced, deleted, inhibited or modified, in a manner that results in increased yields of cellobiohydrolase within the organism or in the culture. For example, knockout of Alp1 function results in a cell that is protease deficient. Knockout of pyr5 function results in a cell with a pyrimidine deficient phenotype. In one genetic engineering approach, homologous recombination can be used to induce targeted gene modifications by specifically targeting a gene in vivo to suppress expression of the encoded protein. In an alternative approach, siRNA, antisense, or ribozyme technology can be used to inhibit gene expression.

In some embodiments, the host cell for expression is a fungal cell (e.g., *Myceliophthora thermophila*) genetically modified to reduce the amount of endogenous cellobiose dehydrogenase (EC 1.1.3.4) and/or other enzyme (e.g., protease) activity that is secreted by the cell. A variety of methods are known in the art for reducing expression of protein in a cell, including deletion of all or part of the gene encoding the protein and site-specific mutagenesis to disrupt expression or activity of the gene product. See, e.g., Chaveroche et al., 2000, *Nucleic Acids Research*, 28:22 e97; Cho et al., 2006, *MPMI* 19: 1, pp. 7-15; Maruyama and Kitamoto, 2008, *Biotechnol Lett* 30:1811-1817; Takahashi et al., 2004, *Mol Gen Genomics* 272: 344-352; and You et al., 2009, *Arch Micriobiol* 191:615-622, the contents of each of which is incorporated by reference herein in its entirety. Random mutagenesis, followed by screening for desired mutations, can also be used. See e.g., Combier et al., 2003, *FEMS Microbiol Lett* 220: 141-8 and Firon et al., 2003, *Eukaryot Cell* 2:247-55, incorporated by reference herein in its entirety.

Exemplary *Myceliophthora thermophila* cellobiose dehydrogenases are CDH1 (SEQ ID NO:24), encoded by the nucleotide sequence SEQ ID NO:23, and CDH2 (SEQ ID NO:26) encoded by the nucleotide sequence SEQ ID NO:25. The genomic sequence for the Cdh1 encoding CDH1 has accession number AF074951.1. In one approach, gene disruption is achieved using genomic flanking markers (see, e.g., Rothstein, 1983, *Methods in Enzymology* 101:202-11).

Site-directed mutagenesis may be used to target a particular domain, in some cases, to reduce enzymatic activity (e.g., glucose-methanol-choline oxido-reductase N and C domains of a cellobiose dehydrogenase or heme binding domain of a cellobiose dehydrogenase; see, e.g., Rotsaert et al., 2001, *Arch. Biochem. Biophys.* 390:206-14, which is incorporated by reference herein in its entirety).

In some embodiments, the cell is modified to reduce production of endogenous cellobiose dehydrogenases. In some embodiments, the cell is modified to reduce production of either CDH1 or CDH2. In some embodiments, the host cell has less than 75%, sometimes less than 50%, sometimes less than 30%, sometimes less than 25%, sometimes less than 20%, sometimes less than 15%, sometimes less than 10%, sometimes less than 5%, and sometimes less than 1% of the CDH1 and/or CDH2 activity of the corresponding cell in which the gene is not disrupted.

Transformation and Cell Culture

Introduction of a vector or DNA construct into a host cell can be effected by calcium phosphate transfection, DEAE-Dextran mediated transfection, PEG-mediated transformation, electroporation, or other common techniques (See Davis et al., 1986, *Basic Methods in Molecular Biology*, which is incorporated herein by reference).

The engineered host cells can be cultured in conventional nutrient media modified as appropriate for activating promoters, selecting transformants, or amplifying the cellobiohydrolase polynucleotide. Culture conditions, such as temperature, pH and the like, are those previously used with the host cell selected for expression, and will be apparent to those skilled in the art. As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques*, fourth edition W.H. Freeman and Company; and Ricciardelli, et al., (1989) *In Vitro Cell Dev. Biol.* 25:1016-1024, all of which are incorporated herein by reference. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York); Jones, ed. (1984) *Plant Gene Transfer and Expression Protocols*, Humana Press, Totowa, N.J. and *Plant Molecular Biology* (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture Catalogue* and supplement (1997) also from Sigma-Aldrich, Inc (St Louis, Mo.) ("Sigma-PCCS"), all of which are incorporated herein by reference.

In some embodiments, cells expressing the cellobiohydrolase polypeptides of the invention are grown under batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

Cell-free transcription/translation systems can also be employed to produce cellobiohydrolase polypeptides using the polynucleotides of the present invention. Several such systems are commercially available. A general guide to in vitro transcription and translation protocols is found in Tymms (1995) *In vitro Transcription and Translation Protocols: Methods in Molecular Biology*, Volume 37, Garland Publishing, NY, which is incorporated herein by reference.

X. Production and Recovery of Cellobiohydrolase Type 1 Variants

In another aspect, the present invention is directed to a method of making a polypeptide having cellobiohydrolase activity. In some embodiments, the method comprises: providing a host cell transformed with any one of the described cellobiohydrolase polynucleotides of the present invention; culturing the transformed host cell in a culture medium under conditions in which the host cell expresses the encoded cellobiohydrolase polypeptide; and optionally recovering or isolating the expressed cellobiohydrolase polypeptide, or recovering or isolating the culture medium containing the expressed cellobiohydrolase polypeptide. The method further provides optionally lysing the transformed host cells after expressing the encoded cellobiohydrolase polypeptide and optionally recovering or isolating the expressed cellobiohydrolase polypeptide from the cell lysate. The present invention further provides a method of making an cellobiohydrolase polypeptide, said method comprising cultivating a host cell transformed with a cellobiohydrolase polypeptide under conditions suitable for the production of the cellobiohydrolase polypeptide and recovering the cellobiohydrolase polypeptide.

Typically, recovery or isolation of the cellobiohydrolase polypeptide is from the host cell culture medium, the host cell or both, using protein recovery techniques that are well known in the art, including those described herein. Cells are typically harvested by centrifugation, disrupted by physical or chemical means, and the resulting crude extract may be retained for further purification. Microbial cells employed in expression of proteins can be disrupted by any convenient method, including freeze-thaw cycling, sonication, mechanical disruption, or use of cell lysing agents, or other methods, which are well known to those skilled in the art.

The resulting polypeptide may be recovered/isolated and optionally purified by any of a number of methods known in the art. For example, the polypeptide may be isolated from the nutrient medium by conventional procedures including, but not limited to, centrifugation, filtration, extraction, spray-drying, evaporation, chromatography (e.g., ion exchange, affinity, hydrophobic interaction, chromatofocusing, and size exclusion), or precipitation. Protein refolding steps can be used, as desired, in completing the configuration of the mature protein. Finally, high performance liquid chromatography (HPLC) can be employed in the final purification steps. Purification of BGL1 is described in Parry et al., 2001, *Biochem. J.* 353:117, and Hong et al., 2007, *Appl. Microbiol. Biotechnol.* 73:1331, both incorporated herein by reference. In addition to the references noted supra, a variety of purification methods are well known in the art, including, for example, those set forth in Sandana (1997) *Bioseparation of Proteins*, Academic Press, Inc.; Bollag et al. (1996) *Protein Methods*, 2$^{nd}$ Edition, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice 3$^{rd}$ Edition*, Springer Verlag, NY; Janson and Ryden (1998) *Protein Purification: Principles, High Resolution Methods and Applications, Second Edition*, Wiley-VCH, NY; and Walker (1998) *Protein Protocols on CD-ROM*, Humana Press, NJ, all of which are incorporated herein by reference.

Immunological methods may be used to purify cellobiohydrolase polypeptides. In one approach, antibody raised against the cellobiohydrolase polypeptides (e.g., against a polypeptide comprising SEQ ID NO:1 or an immunogenic fragment thereof) using conventional methods is immobilized on beads, mixed with cell culture media under conditions in which the cellobiohydrolase is bound, and precipitated. In a related approach immunochromatography is used.

As noted, in some embodiments the cellobiohydrolase is expressed as a fusion protein including a non-enzyme portion. In some embodiments the cellobiohydrolase sequence is fused to a purification facilitating domain. As used herein, the term "purification facilitating domain" refers to a domain that mediates purification of the polypeptide to which it is fused. Suitable purification domains include metal chelating peptides, histidine-tryptophan modules that allow purification on immobilized metals, a sequence which binds glutathione (e.g., GST), a hemagglutinin (HA) tag (corresponding to an epitope derived from the influenza hemagglutinin protein; Wilson et al., 1984, *Cell* 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the CBH1a polypeptide is useful to facilitate purification. One expression vector contemplated for use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography, as described in Porath et al., 1992, *Protein Expression and Purification* 3:263-281) while the enterokinase cleavage site provides a means for separating the CBH1a polypeptide from the fusion protein. pGEX vectors (Promega; Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

XI. Methods of Using Cellobiohydrolase Type 1 Variants and Cells Expressing Cellobiohydrolase Type 1 Variants The cellobiohydrolase variants as described herein have multiple industrial applications, including but are not limited to, sugar production (e.g. glucose syrups), biofuels production, textile treatment, pulp or paper treatment, and applications in detergents or animal feed. A host cell containing a cellobiohydrolase variant of the present invention may be used without recovery and purification of the recombinant cellobiohydrolase, e.g., for use in a large scale biofermentor. Alternatively, the recombinant cellobiohydrolase variant may be expressed and purified from the host cell. The cellobiohydrolase variants of the present invention may also be used according to the methods of Section III ("Improved Saccharification Process") of WO 2010/120557, the contents of which are incorporated by reference herein.

The variant cellobiohydrolases that have been described herein are particularly useful for breaking down cellulose to smaller oligosaccharides, disaccharides and monosaccharides. In some embodiments, the variant cellobiohydrolases are useful in saccharification methods. In some embodiments, the variant cellobiohydrolases may be used in combination with other cellulase enzymes including, for example, conventional enzymatic saccharification methods, to produce fermentable sugars.

Therefore, in one aspect the present invention provides a method of producing an end-product from a cellulosic substrate, the method comprising contacting the cellulosic substrate with a cellobiohydrolase variant as described herein (and optionally other cellulases) under conditions in which fermentable sugars are produced, and contacting fermentable sugars with a microorganism in a fermentation to produce the end-product. In some embodiments, the method further comprises pretreating the cellulosic substrate to increase its susceptibility to hydrolysis prior to contacting the cellulosic substrate with the cellobiohydrolase variant (and optionally other cellulases).

In some embodiments, enzyme compositions comprising the cellobiohydrolase variants of the present invention may be reacted with a biomass substrate in the range of about 25° C. to 100° C., about 30° C. to 90° C., about 30° C. to 80° C., and about 30° C. to 70° C. Also the biomass may be reacted with the cellobiohydrolase enzyme compositions at about 25° C., at about 30° C., at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C. and at about 100° C. Generally the pH range will be from about pH 3.0 to 8.5, pH 3.5 to 8.5, pH 4.0 to 7.5, pH 4.0 to 7.0 and pH 4.0 to 6.5. The incubation time may vary for example from 1.0 to 240 hours, from 5.0 to 180 hrs and from 10.0 to 150 hrs. For example, the incubation time will be at least 1 hr, at least 5 hrs, at least 10 hrs, at least 15 hrs, at least 25 hrs, at least 50 hr, at least 100 hrs, at least 180 and the like. Incubation of the cellulase under these conditions and subsequent contact with the substrate may result in the release of substantial amounts of fermentable sugars from the substrate (e.g., glucose when the cellulase is combined with β-glucosidase). For example at least 20%, at least 30%, at least 40%, at least 50%, at least 60%, at least 70%, at least 80%, at least 90% or more fermentable sugar may be available as compared to the release of sugar by a wild-type polypeptide.

In some embodiments, an end-product of a fermentation is any product produced by a process including a fermentation step using a fermenting organism. Examples of end-products of a fermentation include, but are not limited to, alcohols (e.g., fuel alcohols such as ethanol and butanol), organic acids (e.g., citric acid, acetic acid, lactic acid, gluconic acid, and succinic acid), glycerol, ketones, diols, amino acids (e.g., glutamic acid), antibiotics (e.g., penicillin and tetracycline), vitamins (e.g., beta-carotine and B12), hormones, and fuel molecules other than alcohols (e.g., hydrocarbons).

In some embodiments, the fermentable sugars produced by the methods of the present invention may be used to produce an alcohol (such as, for example, ethanol, butanol, and the like). The variant cellobiohydrolases of the present invention may be utilized in any method used to generate alcohols or other biofuels from cellulose, and are not limited necessarily to those described herein. Two methods commonly employed are the separate saccharification and fermentation (SHF) method (see, Wilke et al., Biotechnol. Bioengin. 6:155-75 (1976)) or the simultaneous saccharification and fermentation (SSF) method disclosed for example in U.S. Pat. Nos. 3,990,944 and 3,990,945.

The SHF method of saccharification comprises the steps of contacting a cellulase with a cellulose containing substrate to enzymatically break down cellulose into fermentable sugars (e.g., monosaccharides such as glucose), contacting the fermentable sugars with an alcohol-producing microorganism to produce alcohol (e.g., ethanol or butanol) and recovering the alcohol. In some embodiments, the method of consolidated bioprocessing (CBP) can be used, where the cellulase production from the host is simultaneous with saccharification and fermentation either from one host or from a mixed cultivation.

In addition to SHF methods, a SSF method may be used. In some cases, SSF methods result in a higher efficiency of alcohol production than is afforded by the SHF method (Drissen et al., Biocatalysis and Biotransformation 27:27-35 (2009). One disadvantage of SSF over SHF is that higher temperatures are required for SSF than for SHF. In one embodiment, the present invention claims cellobiohydrolase polypeptides that have higher thermostability than a wild-type cellobiohydrolase and one practicing the present invention could expect an increase in ethanol production if using the cellulases described here in combination with SSF.

For cellulosic substances to be used effectively as substrates for the saccharification reaction in the presence of a cellulase of the present invention, it is desirable to pretreat the substrate. Means of pretreating a cellulosic substrate are known in the art, including but not limited to chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms), and the present invention is not limited by such methods.

Any alcohol producing microorganism such as those known in the art, e.g., *Saccharomyces cerevisiae*, can be employed with the present invention for the fermentation of fermentable sugars to alcohols and other end-products.

The fermentable sugars produced from the use of one or more cellobiohydrolase variants encompassed by the invention may be used to produce other end-products besides alcohols, such as but not limited to other biofuels compounds, acetone, an amino acid (e.g., glycine, lysine, and the like), organic acids (e.g., lactic acids and the like), glycerol, ascorbic acid, a diol (e.g., 1,3-propanediol, butanediol, and the like), vitamins, hormones, antibiotics, other chemicals, and animal feeds.

The cellobiohydrolase variants as described herein are further useful in the pulp and paper industry. In the pulp and paper industry, neutral cellulases can be used, for example, in deinking of different recycled papers and paperboards having neutral or alkaline pH, in improving the fiber quality, or increasing the drainage in paper manufacture. Other examples include, for example, the removal of printing paste thickener and excess dye after textile printing.

Enzyme Mixtures

In another aspect, the invention provides an enzyme mixture that comprises a cellobiohydrolase variant polypeptide as described herein. In some embodiments, the enzymes of the enzyme mixture may be secreted from a host cell and in other embodiments, the enzymes of the enzyme mixture may not be secreted. The enzyme mixture may be cell-free, or in alternative embodiments, may not be separated from host cells that secrete an enzyme mixture component. A cell-free enzyme mixture typically comprises enzymes that have been separated from any cells. Cell-free enzyme mixtures can be prepared by any of a variety of methodologies that are known in the art, such as filtration or centrifugation methodologies. In certain embodiments, the enzyme mixture can be, for example, partially cell-free, substantially cell-free, or entirely cell-free. In some embodiments, one or more enzymes of the enzyme mixture are not secreted by the host cell. The cells may be lysed to release the enzyme(s). Enzymes may be recovered from the cell lysate or the cell lysate may be combined, with partial purification or without further purification, with the substrate.

The cellobiohydrolase variant and any additional enzymes present in an enzyme mixture may be secreted from a single genetically modified host cell or by different microbes in combined or separate fermentations. Similarly, the cellobiohydrolase variant and any additional enzymes present in the enzyme mixture may be expressed individually or in subgroups from different strains of different organisms and the enzymes combined in vitro to make the enzyme mixture. It is also contemplated that the cellobiohydrolase variant and any additional enzymes in the enzyme mixture may be expressed individually or in sub-groups from different strains of a single organism, and the enzymes combined to make the enzyme mixture. In some embodiments, all of the enzymes are expressed from a single host organism, such as a genetically modified fungal cell.

In some embodiments, the enzyme mixture comprises other types of cellulases, selected from but not limited to cellobiohydrolase, endoglucanase, β-glucosidase, and glycoside hydrolase 61 protein (GH61) cellulases. These enzymes may be wild-type or recombinant enzymes. In some embodiments, the cellobiohydrolase is a type 2 cellobiohydrolase, e.g., a *T. reesei* cellobiohydrolase II. In some embodiments, the endoglucanase comprises a catalytic domain derived from the catalytic domain of a *Streptomyces avermitilis* endoglucanase. See US 2010/0267089, incorporated herein by reference. In some embodiments, the at least one cellulase is derived from *Acidothermus cellulolyticus, Thermobifida fusca, Humicola grisea, Myceliophthora thermophilia, Chaetomium thermophilum, Acremonium* sp., *Thielavia* sp, *Trichoderma reesei, Aspergillus* sp., or a *Chrysosporium* sp. Cellulase enzymes of the cellulase mixture work together resulting in decrystallization and hydrolysis of the cellulose from a biomass substrate to yield fermentable sugars, such as but not limited to glucose (See Brigham et al., 1995, in Handbook on Bioethanol (C. Wyman ed.) pp 119-141, Taylor and Francis, Washington D.C., which is incorporated herein by reference).

Cellulase mixtures for efficient enzymatic hydrolysis of cellulose are known (see, e.g., Viikari et al., 2007, "Thermostable enzymes in lignocellulose hydrolysis" *Adv Biochem Eng Biotechnol* 108:121-45, and US Pat. publications US 2009/0061484; US 2008/0057541; and US 2009/0209009 to Iogen Energy Corp.), each of which is incorporated herein by reference for all purposes. In some embodiments, mixtures of purified naturally occurring or recombinant enzymes are combined with cellulosic feedstock or a product of cellulose hydrolysis. Alternatively or in addition, one or more cell populations, each producing one or more naturally occurring or recombinant cellulases, may be combined with cellulosic feedstock or a product of cellulose hydrolysis.

In some embodiments, the enzyme mixture comprises an isolated CBH1a variant as described herein and at least one or more of an isolated cellobiohydrolase type 2 such as a CBH2b, an isolated endoglucanase (EG) such as a type 2 endoglucanase (EG2), an isolated β-glucosidase (Bgl), and an isolated glycoside hydrolase 61 protein (GH61). In some embodiments, at least 20%, at least 25%, at least 30%, at least 35%, at least 40%, at least 45%, or at least 50% of the enzyme mixture is a CBH1a variant. In some embodiments, the enzyme mixture further comprises a cellobiohydrolase type 2 (e.g., CBH2b), and the CBH1a variant and the CBH2b together comprise at least 25%, at least 30%, at least 35%, at least 40%, at least 45%, at least 50%, at least 55%, at least 60%, at least 65%, at least 70%, at least 75%, or at least 80% of the enzyme mixture. In some embodiments, the enzyme mixture further comprises a β-glucosidase (Bgl), and the CBH1a variant, the CBH2b, and the Bgl together comprise at least 30%, at least 35%, at least 40%, at least 45%, at least 50%, at least 55%, at least 60%, at least 65%, at least 70%, at least 75%, at least 80%, or at least 85% of the enzyme mixture. In some embodiments, the enzyme mixture further comprises an endoglucanase (EG), and the CBH1a variant, the CBH2b, the Bgl, and the EG together comprise at least 35%, at least 40%, at least 45%, at least 50%, at least 55%, at least 60%, at least 65%, at least 70%, at least 75%, at least 80%, at least 85%, or at least 90% of the enzyme mixture. In some embodiments, the enzyme mixture comprises a CBH1a variant as described herein, a cellobiohydrolase type 2b (CBH2b), a β-glucosidase (Bgl), an endoglucanase (EG), and a glycoside hydrolase 61 protein (GH61). In some embodiments, the enzyme mixture composition comprises isolated cellulases in the following proportions by weight (wherein the total weight of the cellulases is 100%): about 20%-10% of EG, about 20%-10% of Bgl, about 20%-25% of CBH2b, about 10%-30% of GH61, and about 30%-25% of a CBH1a variant of the present invention. In some embodiments, the enzyme mixture composition comprises isolated cellulases in the following proportions by weight: about 20%-10% of EG, about 25%-15% of Bgl, about 25%-30% of CBH2b, about 10%-15% of GH61, and about 20%-30% of a CBH1a variant of the present invention. In some embodiments, the enzyme mixture composition comprises isolated cellulases in the following proportions by weight: about 10%-15% of EG, about 20%-25% of Bgl, 25%-35% of CBH2b, about 15%-5% of Gh61, and about 30%-20% of a CBH1a variant of the present invention. In some embodiments, the enzyme mixture composition comprises isolated cellulases in the following proportions by weight: about 15%-5% of EG, about 15%-10% of Bgl, 40%-10% of CBH2b, about 25%-5% of GH61, and about 45%-30% of a CBH1a variant of the present invention. In some embodiments, the enzyme mixture composition comprises isolated cellulases in the following proportions by weight: about 10% of EG, about 15% of Bgl, about 10% of a CBH2b, about 25% of GH61, and about 40% of a CBH1a variant of the present invention. In some embodiments, the enzyme mixture composition comprises isolated cellulases in the following proportions by weight: about 0% of EG, about 15%-10% of Bgl, 30%-40% of a CBH2b, about 15%-10% of GH61, and about 30%-40% of a CBH1a variant of the present invention. In some embodiments, the enzyme component comprises more than 1 CBH1a variant (e.g., 2, 3 or 4 different CBH1a variants as disclosed herein). In some embodiments, an enzyme mixture composition of the invention can also contain one or more additional proteins such as those listed below. In some embodiments, an enzyme mixture composition of the invention can also contain one or more additional enzymes other than the EG, Bgl, CBH2b, GH61, and/or CBH1a variant recited herein, such as the enzymes listed below. In some embodiments, an enzyme mixture composition of the invention can also contain one or more additional cellulases other than the EG, Bgl, CBH2b, GH61, and/or CBH1a variant recited herein.

A cellobiohydrolase variant polypeptide of the invention may also be present in mixtures with non-cellulase enzymes that degrade cellulose, hemicellulose, pectin, and/or lignocellulose.

A "hemicellulase" as used herein, refers to a polypeptide that can catalyze hydrolysis of hemicellulose into small polysaccharides such as oligosaccharides, or monomeric saccharides. Hemicellullases include xylan, glucuonoxylan, arabinoxylan, glucomannan and xyloglucan. Hemicellulases include, for example, the following: endoxylanases, β-xylosidases, α-L-arabinofuranosidases, α-D-glucuronidases, feruloyl esterases, coumarolyl esterases, α-galactosidases, β-galactosidases, β-mannanases, and β-mannosidases. An enzyme mixture may therefore comprise a cellobiohydrolase variant of the invention and one or more hemicellulases.

An endoxylanase (EC 3.2.1.8) catalyzes the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyse 1,4 xylosidic linkages in glucuronoarabinoxylans.

A β-xylosidase (EC 3.2.1.37) catalyzes the hydrolysis of 1,4-β-D-xylans, to remove successive D-xylose residues from the non-reducing termini. This enzyme may also be referred to as xylan 1,4-β-xylosidase, 1,4-β-D-xylan xylohydrolase, exo-1,4-β-xylosidase, or xylobiase.

An α-L-arabinofuranosidase (EC 3.2.1.55) catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase.

An alpha-glucuronidase (EC 3.2.1.139) catalyzes the hydrolysis of an alpha-D-glucuronoside to D-glucuronate and an alcohol.

An acetylxylanesterase (EC 3.1.1.72) catalyzes the hydrolysis of acetyl groups from polymeric xylan, acetylated xylose, acetylated glucose, alpha-napthyl acetate, and p-nitrophenyl acetate.

A feruloyl esterase (EC 3.1.1.73) has 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II.

A coumaroyl esterase (EC 3.1.1.73) catalyzes a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. The enzyme also falls within EC 3.1.1.73 so may also be referred to as a feruloyl esterase.

An α-galactosidase (EC 3.2.1.22) catalyzes the hydrolysis of terminal, non-reducing α-D-galactose residues in α-D-galactosides, including galactose oligosaccharides, galactomannans, galactans and arabinogalactans. This enzyme may also be referred to as melibiase.

A β-galactosidase (EC 3.2.1.23) catalyzes the hydrolysis of terminal non-reducing β-D-galactose residues in β-D-galactosides. Such a polypeptide may also be capable of hydrolyzing α-L-arabinosides. This enzyme may also be referred to as exo-(1->4)-β-D-galactanase or lactase.

A 6-mannanase (EC 3.2.1.78) catalyzes the random hydrolysis of 1,4-β-D-mannosidic linkages in mannans, galactomannans and glucomannans. This enzyme may also be referred to as mannan endo-1,4-β-mannosidase or endo-1,4-mannanase.

A β-mannosidase (EC 3.2.1.25) catalyzes the hydrolysis of terminal, non-reducing β-D-mannose residues in β-D-mannosides. This enzyme may also be referred to as mannanase or mannase.

A glucoamylase (EC 3.2.1.3) is an enzyme which catalyzes the release of D-glucose from non-reducing ends of oligo- and poly-saccharide molecules. Glucoamylase is also generally considered a type of amylase known as amylo-glucosidase.

An amylase (EC 3.2.1.1) is a starch cleaving enzyme that degrades starch and related compounds by hydrolyzing the α-1,4 and/or α-1,6 glucosidic linkages in an endo- or an exo-acting fashion. Amylases include α-amylases (EC 3.2.1.1); β-amylases (3.2.1.2), amylo-amylases (EC 3.2.1.3), α-glucosidases (EC 3.2.1.20), pullulanases (EC 3.2.1.41), and isoamylases (EC 3.2.1.68). In some embodiments, the amylase is an α-amylase.

One or more enzymes that degrade pectin may also be included in an enzyme mixture that comprises a cellobiohydrolase variant of the invention. A pectinase catalyzes the hydrolysis of pectin into smaller units such as oligosaccharide or monomeric saccharides. An enzyme mixture may comprise any pectinase, for example an endo-polygalacturonase, a pectin methyl esterase, an endo-galactanase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase or a xylogalacturonase.

An endo-polygalacturonase (EC 3.2.1.15) catalyzes the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

A pectin methyl esterase (EC 3.1.1.11) catalyzes the reaction: pectin+n $H_2O$=n methanol+pectate. The enzyme may also been known as pectinesterase, pectin demethoxylase, pectin methoxylase, pectin methylesterase, pectase, pectinoesterase or pectin pectylhydrolase.

A endo-galactanase (EC 3.2.1.89) catalyzes the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

A pectin acetyl esterase catalyzes the deacetylation of the acetyl groups at the hydroxyl groups of GalUA residues of pectin.

An endo-pectin lyase (EC 4.2.2.10) catalyzes the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

A pectate lyase (EC 4.2.2.2) catalyzes the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

An alpha rhamnosidase (EC 3.2.1.40) catalyzes the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

An exo-galacturonase (EC 3.2.1.82) hydrolyzes pectic acid from the non-reducing end, releasing digalacturonate. The enzyme may also be known as exo-poly-α-galacturonosidase, exopolygalacturonosidase or exopolygalacturanosidase.

An exo-galacturonase (EC 3.2.1.67) catalyzes a reaction of the following type: (1,4-α-D-galacturonide)n+H2O=(1,4-α-D-galacturonide)n-i+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

An exopolygalacturonate lyase (EC 4.2.2.9) catalyzes eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

A rhamnogalacturonan hydrolyzes the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

A rhamnogalacturonan lyase cleaves α-L-Rhap-(1→4)-α-D-GalpA linkages in an endo-fashion in rhamnogalacturonan by beta-elimination.

A rhamnogalacturonan acetyl esterase catalyzes the deacetylation of the backbone of alternating rhamnose and galacturonic acid residues in rhamnogalacturonan.

A rhamnogalacturonan galacturonohydrolase hydrolyzes galacturonic acid from the non-reducing end of strictly alternating rhamnogalacturonan structures in an exo-fashion. This enzyme may also be known as xylogalacturonan hydrolase.

An endo-arabinanase (EC 3.2.1.99) catalyzes endohydrolysis of 1,5-α-arabinofuranosidic linkages in 1,5-arabinans. The enzyme may also be know as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

One or more enzymes that participate in lignin degradation may also be included in an enzyme mixture that comprises a cellobiohydrolase variant of the invention. Enzymatic lignin depolymerization can be accomplished by lignin peroxidases, manganese peroxidases, laccases and cellobiose dehydrogenases (CDH), often working in synergy. These extracellular enzymes are often referred to as lignin-modifying enzymes or LMEs. Three of these enzymes comprise two glycosylated heme-containing peroxidases: lignin peroxidase (LIP); Mn-dependent peroxidase (MNP); and, a copper-containing phenoloxidase laccase (LCC).

Laccase: Laccases are copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

Mn-dependent peroxidase: The enzymatic activity of Mn-dependent peroxidase (MnP) in is dependent on Mn2+. Without being bound by theory, it has been suggested that the main role of this enzyme is to oxidize Mn2+ to Mn3+ (Glenn et al. (1986) Arch. Biochem. Biophys. 251:688-696). Subsequently, phenolic substrates are oxidized by the Mn3+ generated.

Lignin peroxidase: Lignin peroxidase is an extracellular heme that catalyses the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being bound by a theory, has been proposed to function as a physiological redox mediator in the LiP-catalysed oxidation of lignin in vivo (Harvey, et al. (1986) FEBS Lett. 195, 242-246).

An enzymatic mixture comprising a cellobiohydrolase variant of the invention may further comprise at least one of the following: a protease or a lipase that participates in cellulose degradation.

"Protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

An enzyme mixture that comprises a cellobiohydrolase variant of the invention may also comprise at least one expansin or expansin-like protein, such as a swollenin (see Salheimo et al., *Eur. J. Biohem.* 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

An enzyme mixture that comprises a cellobiohydrolase variant of the invention may also comprise at least one of the following: a polypeptide product of a cellulose integrating protein, scaffoldin or a scaffoldin-like protein, for example CipA or CipC from *Clostridium thermocellum* or *Clostridium cellulolyticum* respectively. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module that mediates attachment of the cellulosome to its substrate. A scaffoldin or cellulose integrating protein for the purposes of this invention may comprise one or both of such domains.

An enzyme mixture that comprises a cellobiohydrolase variant of the invention may also comprise at least one cellulose induced protein or modulating protein, for example as encoded by cip1 or cip2 gene or similar genes from *Trichoderma reesei* (see Foreman et al., *J. Biol. Chem.* 278(34), 31988-31997, 2003).

An enzyme mixture that comprises a cellobiohydrolase variant of the invention may comprise a member of each of the classes of the polypeptides described above, several members of one polypeptide class, or any combination of these polypeptide classes.

Cellobiohydrolase Compositions

The cellobiohydrolase variants of the present invention may be used in combination with other optional ingredients such as a buffer, a surfactant, and/or a scouring agent. A buffer may be used with a cellobiohydrolase of the present invention (optionally combined with other cellulases, including another cellobiohydrolase) to maintain a desired pH within the solution in which the cellobiohydrolase is employed. The exact concentration of buffer employed will depend on several factors which the skilled artisan can determine. Suitable buffers are well known in the art. A surfactant may further be used in combination with the cellobiohydrolases of the present invention. Suitable surfactants include any surfactant compatible with the cellobiohydrolase and, optionally, with any other cellulases being used. Exemplary surfactants include an anionic, a non-ionic, and ampholytic surfactants. Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, etc. Suitable counter ions for anionic surfactants include, but are not limited to, alkali metal ions such as sodium and potassium; alkaline earth metal ions such as calcium and magnesium; ammonium ion; and alkanolamines having 1 to 3 alkanol groups of carbon number 2 or 3. Ampholytic surfactants include, e.g., quaternary ammonium salt sulfonates, and betaine-type ampholytic surfactants. Nonionic surfactants generally comprise polyoxyalkylene ethers, as well as higher fatty acid alkanolamides or alkylene oxide adduct thereof, and fatty acid glycerine monoesters. Mixtures of surfactants can also be employed as is known in the art.

The present invention may be practiced at effective amounts, concentrations, and lengths of time. An effective amount of cellobiohydrolase is a concentration of cellobiohydrolase sufficient for its intended purpose. For example, an effective amount of cellobiohydrolase within a solution may vary depending on whether the intended purpose is to use the enzyme composition comprising the cellobiohydrolase in a saccharification process, or for example a textile application such as stone-washing denim jeans. The amount of cellobiohydrolase employed is further dependent on the equipment employed, the process parameters employed, and the cellulase activity, e.g., a particular solution will require a lower concentration of cellobiohydrolase where a more active cellulase composition is used as compared to a less active cellulase composition. A concentration of cellobiohydrolase and length of time that an cellobiohydrolase will be in contact with the desired target further depends on the particular use employed by one of skill in the art, as is described herein.

One skilled in the art may practice the present invention using cellobiohydrolases in either aqueous solutions, or a solid cellobiohydrolase concentrate. When aqueous solutions are employed, the cellobiohydrolase solution can easily be diluted to allow accurate concentrations. A concentrate can be in any form recognized in the art including, but not limited to, liquids, emulsions, gel, pastes, granules, powders, an agglomerate, or a solid disk. Other materials can also be used with or placed in the cellulase composition of the present invention as desired, including stones, pumice, fillers, solvents, enzyme activators, and anti-redeposition agents depending on the intended use of the composition.

XII. EXAMPLES

The following examples are offered to illustrate, but not to limit, the claimed invention.

Example 1

Wild-Type C1 Cbh1a Gene Acquisition and Construction of Expression Vector cDNA coding the secreted wild-type C1 CBH1a protein (SEQ ID NO:2) was amplified from a cDNA library prepared by Symbio, Inc. (Menlo Park, Calif.). Expression constructs were prepared in which the Cbh1a WT sequence was linked to a native signal peptide for secretion in *S. cerevisiae*. The signal peptide sequence was PCR amplified with cDNA from the cDNA library. C1 Cbh1a cDNA construct was cloned into a pYTDX20 shuttle vector (i.e., pBS24Ub modified so that transcription is under the control of a C1 chitinase (chi) promoter).

*S. cerevisiae* cells were transformed with the expression vector. Clones with correct Cbh1a sequences were identified and activity was confirmed using a MUL assay (4-methylumbelliferyl β-D-lactopyranoside; see Example 3, infra).

Example 2

Production of C1 CBH1a—Shake Flask Procedure

A single colony of *S. cerevisiae* containing a plasmid with the C1 Cbh1a gene was inoculated into 3 ml of synthetic media containing 60 g/L glucose, 6.7 g/L yeast nitrogen base, 5 g/L ammonium sulfate, and 2 g/L amino acid drop-out mix minus uracil (D9535, United States Biological, Swampscott, Mass.). Cells were grown overnight (at least 16 hours) in an incubator at 30° C. with shaking at 250 rpm. 0.7 ml of this culture was diluted into 50 ml of synthetic defined expression medium containing 20 g/L glucose, 6.7 g/L yeast nitrogen base without amino acids (Y0626, Sigma, St. Louis, Mo.), 5 g/L ammonium sulfate, 10 g/L potassium phosphate (monobasic), 10 g/L galactose, 24 g/L amino acid drop-out mix minus uracil (D9535, United States Biological), 3.6 ml TIPC solution (0.05 g/L thiamine, 0.1 g/L myo-inositol, 0.05 g/L calcium pantotenate and 1 g/L choline chloride) and 0.2 ml vitamin solution (1.5 g/L pyridoxine, 1 g/L P-amino butyric acid, 0.1 g/L biotin, 1 g/L riboflavin, 0.1 g/L folic acid and 1.5 g/L niacin). The pH of the medium was adjusted to pH 6 using hydrochoric acid. This culture was incubated for 72 hours and allowed to grow at 30° C. while shaking at 250 rpm. Cells were harvested by centrifugation (4000 rpm, 4° C., 15 minutes). The supernatant was decanted into a new tube and the activity of the secreted wild-type C1 CBH1a was confirmed using MUL assay (4-methylumbelliferyl β-D-lactopyranoside; see Example 3, infra).

Example 3

Assays to Determine Cellobiohydrolase Thermoactivity and Thermostability

Cellobiohydrolase thermoactivity may be determined using a 4-methylumbelliferyl β-D-lactopyranoside (MUL) assay or by measuring cellobiohydrolase activity on biomass substrate. Cellobiohydrolase thermostability may be determined by exposing the cellobiohydrolase to stress conditions of elevated temperature and/or low pH for an appropriate period of time and then determining residual cellobiohydrolase activity by a MUL assay or a cellulose assay.

4-Methylumbelliferyl β-D-lactopyranoside (MUL) Assay

In a total volume of 75 μl, 50 μl of 0.6 mM 4-methylumbelliferyl β-D-lactopyranoside (MUL) in 250 mM sodium acetate, pH 4.4 was added to 25 μl of *S. cerevisiae* supernatant containing secreted C1 CBH1a protein. The reaction was incubated for 60 minutes at 63° C., then centrifuged briefly and 50 μl was transferred to 150 μl of 1 M $Na_2CO_3$ pH 10.5 in a flat-bottom black plate to terminate the reaction. The amount of deprotonated 4-methylumbelliferyl was measured using fluorescence method with $\lambda_{ex}$=365 nm, $\lambda_{em}$=445 nm with a fluorimeter Spectramax M2 (Molecular Devices, Sunnyvale, Calif.). Fluorescence was calculated by fitting the data to the calibration curve equation y=28515x+6712.9. Multiplying the resulting value by a dilution factor gives the value in mM of 4-methylumbelliferyl formed by the enzyme. When a wild-type C1 CBH1a produced as described in Example 2 was reacted with MUL, the resulting mixture produced fluorescence of 6000 relative fluorescence units (RFU), while the negative control consisting of supernatant of *S. cerevisiae* containing empty vector produced fluorescence of 200-300 under the same reaction conditions.

Biomass Assay

Activity on biomass substrate (wheat straw pretreated under acidic conditions) was measured using a reaction mixture of 400 μl volume containing 15 mg of biomass, 300 μl of supernatant produced as described in Examples 1 and 2 and 100 μl of 250 mM sodium acetate pH 5. The reactions were incubated at 55° C. for 24 hours while shaking at 950 rpm. The reactions were centrifuged and 50 μl of the reaction was added to 25 μl of a 25 g/l solution of *A. niger* β-glucosidase in 250 mM sodium acetate pH 5. This reaction was incubated for 1.5 hours at 50° C. while shaking at 950 rpm to hydrolyze cellobiose to glucose.

Glucose was measured using a GOPOD-format assay (MEGAZYME, Ireland). From the cellobiose hydrolysis reaction, 30 μl was transferred to 170 μl of the GOPOD mixture (containing glucose oxidase, peroxidase and 4-aminoantipyrine) and incubated at room temperature for 20 minutes. The amount of glucose was measured spectrophotometrically at 510 nm with a Spectramax M2 (Molecular Devices, Sunnyvale, Calif.). The amount of glucose can be calculated based on the measured absorbance at 510 nm and using the standard curve when the standards are measured on the same plate. When wild-type C1 CBH1a produced as described in Examples 1 and 2 is used in the described reaction, approximately 0.03 g/l of glucose is produced. The range of operable pH for *S. cerevisiae*-produced C1 CBH1a was found to be between 4 and 6 with the range of operable temperature between 50-60° C., with optimal conditions at pH 5 and 50° C.

Thermostability Assay

The cellobiohydrolase was challenged by incubating under conditions of pH 4.4 and 63° C. or 66° C. for 2 hours, or pH 4 and 68° C. for 2 hours, or pH 4.5 and 70° C. for 24 hours. Following the challenge incubation, residual activity of the cellobiohydrolase was measured using a MUL assay as described above.

Residual cellobiohydrolase activity was also determined using a cellulose assay, using microcrystalline cellulose (Avicel, from Sigma) as a substrate. In a total volume of 400 μL, 75 μL buffered supernatant containing cellobiohydrolase enzyme before and after thermal challenge was added to 75 g/L Avicel in 250 mM sodium acetate buffer (pH 4.5) containing beta-glucosidase, which converts cellobiose to glucose. The reaction was incubated at 50° C., pH 5 for 24 hours while shaking at 950 rpm. Conversion of Avicel to glucose was measured using a GOPOD Assay. Glucose production was measured by mixing 5 μl of the above reaction with 195 μl of the GOPOD assay mix. Absorbance of the solution was measured at 510 nm to determine the amount of glucose produced in the original Avicel biotransformation reaction.

Example 4

High Throughput Assays to Identify CBH1a Variants with Improved Thermostability and pH Tolerance Round 1 Screen Variants obtained from mutagenized libraries of C1 CBH1a were cloned and grown on agar plates containing 30 g/L glucose, 6.7 g/L yeast nitrogen base, 5 g/L ammonium sulfate, and 2 g/L amino acid drop-out mix minus uracil (D9535, United States Biological). Single colonies were picked and cultured as described in Example 2. Initial growth was done in 200 μl cultures and expression was done in 400 μl cultures. The supernatants were screened and evaluated for improvement in thermostability over the wild-type C1 CBH1a (SEQ ID NO:2) using the MUL assay of Example 3 at 63° C. To evaluate improvement, 25 μl of the same supernatant was added to 25 μl of 250 mM sodium acetate pH 4.4 in a 96-well plate and incubated at 63° C. for 2 hours. The reactions were cooled and tested for activity using the MUL assay of Example 3 with the following exceptions: 25 μl of 1.2 mM MUL was added to 50 μl of the supernatant-buffer mixture and the reactions were then incubated at 62° C. for 1 hour. Improved variants were retested in triplicates. Duplicate plates were created to calculate residual activity after the 2 hour thermal challenge where one copy of the plate was kept at 4° C. while the other copy was incubated at 63° C. or 66° C. Both copies were then assayed using the MUL assay as described in this Example. The residual cellobiohydrolase activity was calculated using the formula: % residual activity=100×(fluorescence of challenged samples/fluorescence of unchallenged samples).

Table 3 summarizes the results of the Round 1 screen. Thermostability is presented as fold increase over secreted wild-type C1 CBH1a protein (SEQ ID NO:2). Amino acid substitutions (e.g., "T126V") are relative to the wild-type C1 Cbh1a pre-protein (i.e., having signal peptide) sequence of SEQ ID NO:4.

TABLE 3

Improved C1 CBH1a variants

| Variant # | Amino acid changes over wild-type C1 CBH1a pre-protein (SEQ ID NO: 4) | Thermostability: Fold Improvement over wild-type C1 CBH1a (SEQ ID NO: 2) |
|---|---|---|
| | Wild-Type (SEQ ID NO: 2) | n/a |
| 1 | T126V | + |
| 2 | Q286M | + |
| 3 | G155P; S212P | + |
| 4 | I49V; E69T; S212P; K294P | + |
| 5 | S79P; G155P; S177P; S212P; K294P; E343P | + |

+ indicates a fold improvement of 6- to 8-fold over wild-type C1 CBH1a

Round 2 Screen

Libraries were designed to combine beneficial mutations using Variant 5 as a parent (S79P; G155P; S177P; S212P; K294P; E343P). The resulting CBH1a polypeptides were expressed in yeast and tested for thermostability and pH tolerance. The supernatants were screened and evaluated for improvement in thermostability over Variant 5 using the MUL assay of Example 3 at 66° C. To evaluate improvement, 25 μl of the same supernatant was added to 25 μl of 250 mM sodium acetate, pH 4.4 in a 96-well plate and incubated at 66° C. for 2 hours. The reactions were cooled and tested for activity using MUL assay described above for Round 1.

Table 4 summarizes the results of the Round 2 screen. Thermostability is presented as fold increase over Variant 5. Amino acid substitutions (e.g., "S79P") are relative to the wild-type C1 CBH1a pre-protein (i.e., having signal peptide) sequence of SEQ ID NO:4.

TABLE 4

Improved C1 CBH1a variants

| Variant # | Amino acid changes over wild-type C1 CBH1a pre-protein (SEQ ID NO: 4) | Thermostability: Fold Improvement over Variant 5 (SEQ ID NO: 28) |
|---|---|---|
| 5 | S79P; G155P; S177P; S212P; K294P; E343P | n/a |
| 6 | T24V; T32M; T126V; G155P; S177P; N209G; S212P; K294P; E343P; I405V | ++ |
| 7 | Y2H; T24I; S48W; G155P; S177P; S212P; K294P; E343P | ++ |
| 8 | S79P; Q117N; G155P; S177P; S212P; K294P; E343P; P381G; A417P | +++ |
| 9 | T58I; S79P; P82K; G155P; S177P; S212P; T221H; A241T; K294P; E343P; A417P; S452E | ++ |
| 10 | G39R; S79P; Q117N; G155P; S177Q; S192A; S212P; A241T; K294P; E343P; P381G; A417P | ++ |
| 11 | G39R; S79P; P82K; Q117N; G155P; S177P; S192A; S212P; K294P; E343P; A417P | ++ |
| 12 | S79P; G155P; S177P; S212P; T221H; A241T; K294P; E343P; P381G; A417P | ++ |
| 13 | S30P; T58V; S79P; Q117N; G155P; S177P; S212P; A241T; K294P; E343P; A417P | +++ |
| 14 | S30P; G39R; S79P; Q117N; G155P; S177P; S212P; K294P; E343P; P381G; A417P; S452E | +++ |
| 15 | S30P; T58I; S79P; P82M; Q117N; G155P; S177Q; S212P; K294P; E343P; P381G; A417P | +++ |

TABLE 4-continued

++ indicates a fold improvement of 3- to 4-fold over Variant 5
+++ indicates a fold improvement of greater than 4-fold over Variant 5

Round 3 Screen

Libraries were designed to either combine beneficial mutations or generate new diversity by standard mutagenesis methods using Variant 15 as a parent (S30P; T58I; S79P; P82M; Q117N; G155P; S177Q; S212P; K294P; E343P; P381G; A417P). The resulting CBH1a polypeptides were expressed in yeast and tested for thermostability and pH tolerance. The supernatants were screened and evaluated for improvement in thermostability over Variant 15 using the MUL assay of Example 3 at 68° C. To evaluate improvement, 25 μl of the same supernatant was added to 25 μl of 250 mM sodium acetate, pH 4 in a 96-well plate and incubated at 68° C. for 2 hours. The reactions were cooled and tested for activity using MUL assay described above for Round 1.

Table 5 summarizes the results of the Round 3 screen. Thermostability is presented as fold increase over Variant 15. Amino acid substitutions (e.g., "S30P") are relative to the wild-type C1 CBH1a pre-protein (i.e., having signal peptide) sequence of SEQ ID NO:4.

TABLE 5

Improved C1 CBH1a variants

| Variant # | Amino acid changes over wild-type C1 CBH1a pre-protein (SEQ ID NO: 4) | Thermostability: Fold Improvement over Variant 15 (SEQ ID NO: 32) |
|---|---|---|
| 15 | S30P; T58I; S79P; P82M; Q117N; G155P; S177Q; S212P; K294P; E343P; P381G; A417P | n/a |
| 16 | T24I; S30P; T58I; S79P; P82M; G116T; Q117N; G155P; S177P; S212P; K294P; E343P; P381G; A417P | ++++ |
| 17 | S30P; T58I; S79P; P82M; I90V; Q117N; G155P; S177P; N209G; S212P; T221W; Q286M; K294P; E343P; P381G; A417P | ++++ |
| 18 | T24K; S30P; T58I; S79P; P82M; Q117N; G155P; S177P; S212P; Q286M; K294P; E343P; P381G; A417P | ++++ |
| 19 | S30P; T58I; S79P; P82M; G116T; Q117N; G155P; S177P; S212P; T221W; Q286M; K294P; E343P; P381G; A417P | ++++ |

++++ indicates a fold improvement of greater than 2-fold over Variant 15

Round 4 Screen

Libraries were designed to either combine beneficial mutations or generate new diversity by standard mutagenesis methods using Variant 17 as a parent (S30P; T58I; S79P; P82M; I90V; Q117N; G155P; S177P; N209G; S212P; T221W; Q286M; K294P; E343P; P381G; A417P). The resulting CBH1a polypeptides were expressed in yeast and tested for thermostability and pH tolerance. The supernatants were screened and evaluated for improvement in thermostability over Variant 17 using the MUL assay of Example 3 at 70° C. To evaluate improvement, 25 μl of the same supernatant was added to 25 μl of 250 mM sodium acetate, pH 4.5 in a 96-well plate and incubated at 70° C. for 24 hours. The reactions were cooled and tested for activity using MUL assay described above for Round 1.

Table 6 summarizes the results of the Round 4 screen. Thermostability is presented as fold increase over Variant 17. Amino acid substitutions (e.g., "S30P") are relative to the wild-type C1 CBH1a pre-protein (i.e., having signal peptide) sequence of SEQ ID NO:4.

TABLE 6

Improved C1 CBH1a variants

| Variant # | Amino acid changes over wild-type C1 CBH1a pre-protein (SEQ ID NO: 4) | Thermostability: Fold Improvement over Variant 17 (SEQ ID NO: 34) |
|---|---|---|
| 17 | S30P; T58I; S79P; P82M; I90V; Q117N; G155P; S177P; N209G; S212P; T221W; Q286M; K294P; E343P; P381G; A417P | n/a |
| 20 | S30P; T58I; S79P; P82M; I90V; Q117N; G155P; S177P; N209G; S212P; T221W; Q286M; K294P; E343P; P381G; S401D; A417P | +++++ |
| 21 | T22H; T24I; S30P; T58I; P82M; I90V; Q117N; Y118G; G155P; S177P; N209G; S212P; T221W; T264L; Q286M; K294P; E343P; P381G; V394L; A417P | +++++ |
| 22 | T24I; S30P; T58I; S79P; P82M; I90V; Q117N; G155P; S177P; A205C; N209G; S212P; T221W; Q286M; K294P; E343P; P381G; V394L; A417P | +++++ |
| 23 | T24I; S30P; T58I; E69C; S79P; P82M; I90V; Q117N; G155P; S177P; N209G; S212P; T221W; T264L; Q286M; K294P; E343P; P381G; A417P; G502R; L526A | +++++ |
| 24 | T24I; S30P; T58I; E69C; P82M; I90V; T98L; G155P; S177P; N209G; S212P; T221W; Q286M; K294P; E343P; P381G; A417P; A492V | +++++ |
| 25 | T24I; S30P; T58I; E69C; P82M; I90V; T102H; Q117N; G155P; S177P; N209G; S212P; T221W; Q286M; K294P; E343P; P381G; A417P; A492V; Q508S; P512G | +++++ |

+++++ indicates a fold improvement of greater than 1.5-fold over Variant 17

Example 5

High Throughput Assays to Identify CBH1a Variants with Improved Thermostability and Thermoactivity—Round 5 Screen Variants obtained from mutagenized libraries of C1 CBH1a were cloned and grown on agar plates containing 30 g/L glucose, 6.7 g/L yeast nitrogen base, 5 g/L ammonium sulfate, and 2 g/L amino acid drop-out mix minus uracil (D9535, United States Biological). Single colonies were picked and cultured as described in Example 2. Initial growth was done in 200 μl cultures and expression was done in 400 μl cultures. The supernatants were screened and evaluated for improvement in thermoactivity and thermostability over Variant 20. To evaluate improvement in thermostability, the MUL assay of Example 3 was performed at 70° C. 25 μl of the supernatant was added to 25 μl of 250 mM sodium acetate, pH 4.5 in a 96-well plate and incubated at 70° C. for 24 hours. The reactions were cooled and tested for activity using MUL assay described above for Round 1.

Table 7 summarizes the results of the Round 5 screen. Thermostability is presented as fold increase over Variant 20. Amino acid substitutions (e.g., "S30P") are relative to the wild-type C1 CBH1a pre-protein (i.e., having signal peptide) sequence of SEQ ID NO:4.

TABLE 7

Improved C1 CBH1a variants

| Variant # | Amino acid changes over wild-type C1 CBH1a pre-protein (SEQ ID NO: 4) | Thermostability: Fold Improvement over Variant 20 (SEQ ID NO: 36) |
|---|---|---|
| 20 | S30P; T58I; S79P; P82M; I90V; Q117N; G155P; S177P; N209G; S212P; T221W; Q286M; K294P; E343P; P381G; S401D; A417P | n/a |
| 26 | S30P; T58I; E69N; S79P; P82M; I90V; Q117N; G155P; S177P; N209G; S212P; T221W; Q286M; K294P; E343P; P381G; V394A; S401D; A417P | +++++++ |
| 27 | S30P; T58I; A64T; E69D; S79P; P82M; I90V; Q117N; G155P; S177P; N209G; S212P; T221W; Q286M; K294P; E343P; P381G; V394A; S401D; W403F; A417P | ++++++ |
| 28 | S30P; T58I; A64S; E69D; S79P; P82M; I90V; Q117N; G155P; S177P; N209G; S212P; T221W; Q286M; K294P; E343P; P381G; V394A; S401D; A417P | +++++++ |

TABLE 7-continued

| Improved C1 CBH1a variants | | |
|---|---|---|
| Variant # | Amino acid changes over wild-type C1 CBH1a pre-protein (SEQ ID NO: 4) | Thermostability: Fold Improvement over Variant 20 (SEQ ID NO: 36) |
| 29 | S30P; T58I; S79P; P82M; I90V; Q117N; G155P; S177P; N209G; S212P; T221W; Q286M; K294P; E343P; P381G; V394A; S401D; W403Y; A417P | ++++++ |
| 30 | S30P; T58I; A64T; E69N; S79P; P82M; I90V; Q117N; G155P; S177P; N209G; S212P; T221W; Q286M; K294P; E343P; P381G; V394A; S401D; W403F; A417P | ++++++ |
| 31 | S30P; T58I; S79P; P82M; I90V; Q117N; G155P; S177P; N209G; S212P; T221W; Q286M; K294P; E343P; P381G; V394A; S401D; A417P | ++++++ |
| 32 | S30P; T58I; S79P; I90L; Q117N; G155P; S177P; N209G; S212P; T221W; Q286M; K294P; E343P; P381G; V394A; S401D; A417P | +++++++ |
| 33 | S30P; T58I; E69N; S79P; P82M; I90V; Q117N; G155P; S177P; N209G; S212P; T221W; Q286M; K294P; E343P; P381G; V394A; S401D; W403Y; A417P | +++++++ |
| 34 | S30P; T58I; S79P; P82M; I90V; Q117N; G155P; S177P; N209G; S212P; T221Q; Q286M; K294P; E343P; P381G; S401D; A417P | +++++ |
| 35 | S30P; T58I; S79P; P82M; I90V; Q117N; G155P; S177P; N209G; S212P; T221W; Q286M; K294P; E343P; P381G; V394G; S401D; A417P | +++++ |
| 36 | S30P; T58I; S79P; P82M; I90V; Q117N; G155P; S177P; N209G; S212P; T221W; Q286M; K294P; E343P; P381G; V394S; S401D; A417P | ++++++ |
| 37 | S30P; T58I; S79P; P82M; I90V; Q117N; G155P; S177P; N209G; S212P; T221W; Q286M; K294P; E343P; P381G; V394Q; S401D; A417P | +++++++ |
| 38 | S30P; T58I; S79P; P82M; I90V; Q117N; G155P; S177P; N209G; S212P; T221W; Q286M; K294P; E343P; P381G; V394D; S401D; A417P | ++++++ |

+++++ indicates a fold improvement of 1-1.2-fold in thermostability over Variant 20
++++++ indicates a fold improvement of 1.2-1.3-fold in thermostability over Variant 20
+++++++ indicates a fold improvement of greater than 1.3-fold in thermostability over Variant 20

Example 6

Cellobiohydrolase Variants Showing Increased Specific Activity

As described in Example 3, Variants 5, 8, 10, 11, 13, 14, and 15 were expressed in yeast and tested in a thermoactivity assay. When protein concentration was normalized based on a MUL activity assay, it was apparent that each of Variants 8, 10, 11, 13, 14, and 15 had increased specific activity as compared to Variant 5, as shown in Table 8. As Variant 5 had previously been determined to have comparable activity to wild-type CBH1a (data not shown), these results also suggest that Variants 8, 10, 11, 13, 14, and 15 have increased specific activity over wild-type CBH1a.

Table 8 shows the results of a biomass assay comparing Variants 5, 8, 10, 11, 13, 14, and 15. The proteins were expressed in yeast shake flasks and protein concentration was quantified by measuring activity on MUL. For the biomass assay, the amount of each supernatant containing secreted protein that was added to the reaction was adjusted based on the MUL-quantified protein concentration in order to have equal amounts of protein in each reaction. CBH1a activity was assayed under the following conditions: Substrate=32.5 g/L pretreated wheat straw; pH 5, 50° C., 17 hr. A GOPOD-format assay was used to assess cellobiose production.

TABLE 8

| Biomass assay comparing selected CBH1a variants (using equal protein concentrations) | | | |
|---|---|---|---|
| | Glucose measured (g/L) | Std. Dev. | Fold Improvement |
| Variant 5 | 0.43 | 0.01 | — |
| Variant 8 | 0.62 | 0.02 | 1.44 |
| Variant 10 | 0.47 | 0.01 | 1.09 |
| Variant 11 | 0.53 | 0.01 | 1.23 |
| Variant 13 | 0.70 | 0.02 | 1.63 |
| Variant 14 | 0.52 | 0.01 | 1.21 |
| Variant 15 | 0.71 | 0.02 | 1.65 |

Table 9 shows the results of a microcrystalline cellulose (Avicel, Sigma) assay comparing Variant 8 and wild-type C1 CBH1a expressed in C1 fermentation. Wild-type CBH1a or Variant 8 was purified from the fermentation broth and protein was quantified in g/L using a HPLC method of protein quantification and a bicinchoninic acid (BCA) protein assay. Each protein was then diluted to the same concentration and equal amounts of protein (at a final concentration of 0.25%) were used in each reaction. CBH1a activity was assayed under the following conditions: 0.25% CBH1a, 166 g/L Avicel, pH 5, 50° C. or 65° C., 24 hr. A GOPOD-format assay was used to assess cellobiose production. As shown in Table 9, CBH1a variant 8 expressed in C1 exhibits increased specific activity as compared to wild-type CBH1a.

TABLE 9

| Avicel assay comparing CBH1a variant to wild-type CBH1a (using equal protein concentrations) | | | | | | |
|---|---|---|---|---|---|---|
| | 50° C. | | | 65° C. | | |
| | Glucose measured (g/L) | Std. Dev. | Fold Improvement | Glucose measured (g/L) | Std. Dev. | Fold Improvement |
| Wild-type | 18.93 | 0.14 | — | 9.96 | 0.20 | — |
| Variant 8 | 20.70 | 0.37 | 1.09 | 18.80 | 0.18 | 1.89 |

Example 7

Cellobiohydrolase Variants Showing Increased Thermoactivity

The thermoactivity of selected CBH1a improved variants grown in yeast or in the C1 strain ΔBgl1 was compared to the thermoactivity of wild-type CBH1a at different temperatures. Thermoactivity was tested by a microcrystalline cellulose (Avicel, Sigma) assay. For testing thermoactivity on Avicel, supernatant produced as described in Examples 1 and 2 was diluted ~3× to a concentration which gives signal area of 40 on a HPLC chromatogram when 10 μl of sample is injected for analysis. Activity on Avicel substrate was measured using a reaction mixture of 400 μl volume containing 30 mg of Avicel, 75 μl of normalized supernatant described above, and 325 μl of 250 mM sodium acetate pH 5 containing C1 β-glucosidase. The reactions were incubated at 55° C. and 65° C. for 24 or 72 hours while shaking at 950 rpm. From these reactions, 5 μl was transferred to 195 μl of the GOPOD mixture (Megazyme, Wicklow, Ireland; containing glucose oxidase, peroxidase and 4-aminoantipyrine) and incubated at room temperature for 30 minutes. The amount of glucose was measured spectrophotometrically at 510 nm with a Spectramax M2 (Molecular Devices, Sunnyvale, Calif.). The amount of glucose can be calculated based on the measured absorbance at 510 nm and using the standard curve when the standards are measured on the same plate.

Figure 5:
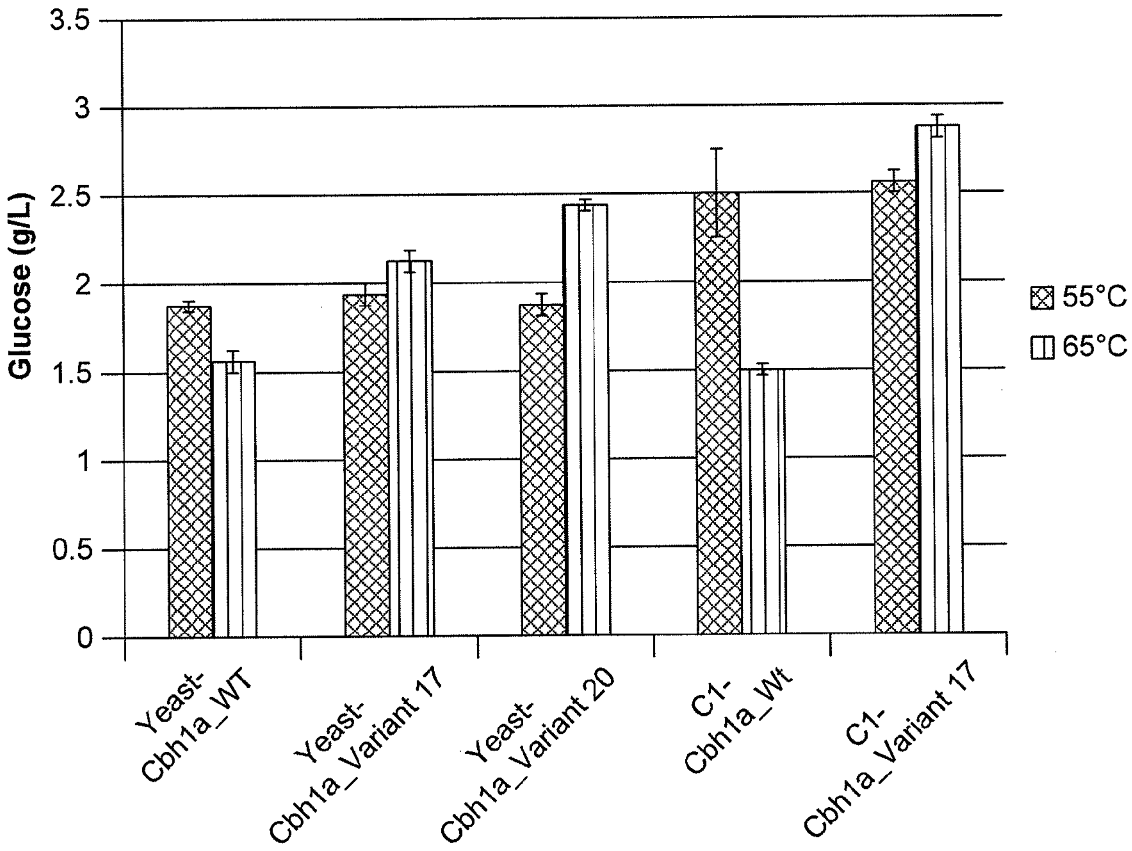
FIG. 5 shows the activity of wild-type C1 CBH1a and C1 CBH1a variants 17 and 20 produced in yeast shake flask and wild-type C1 CBH1a and C1 CBH1a variant 17 produced in C1 shake flask, as determined by cellulose assay at pH 5, 55° C. or 65° C. in a 24 hour reaction, as described in Example 3. n=3, error bars represent ±1SD.

Table 10 and FIG. 5 show the results of the Avicel assay comparing the thermoactivity at 55° C. and 65° C. of wild-type C1 CBH1a grown in yeast, Variant 17 grown in yeast, Variant 20 grown in yeast, wild-type C1 CBH1a grown in C1, and Variant 17 grown in C1.

TABLE 10

| Avicel assay comparing wild-type CBH1a and selected improved CBH1a variants | | | | |
|---|---|---|---|---|
| | Glucose (g/L), Avicel assay at 55° C., pH 5 | Std. Dev. | Glucose (g/L), Avicel assay at 65° C., pH 5 | Std. Dev. |
| WT CBH1a - yeast | 1.861 | 0.019 | 1.581 | 0.040 |
| Variant 17 - yeast | 1.965 | 0.038 | 2.149 | 0.042 |
| Variant 20 - yeast | 1.878 | 0.033 | 2.416 | 0.025 |

TABLE 10-continued

| Avicel assay comparing wild-type CBH1a and selected improved CBH1a variants | | | | |
|---|---|---|---|---|
| | Glucose (g/L), Avicel assay at 55° C., pH 5 | Std. Dev. | Glucose (g/L), Avicel assay at 65° C., pH 5 | Std. Dev. |
| WT CBH1a - C1 | 2.512 | 0.192 | 1.494 | 0.030 |
| Variant 17 - C1 | 2.569 | 0.051 | 2.901 | 0.050 |

Example 8

Truncated Variants with High Thermostability

A "wobble library" was designed and generated to increase expression and secretion of C1 CBH1a in yeast. In this library the third base of each codon is varied across the entire sequence, except at positions that encode methionine and tryptophan, to introduce silent changes. However, due to PCR errors a low level of insertions and deletions can be expected, resulting mostly in inactive variants.

The variant from the wobble library with the highest thermostability of those tested was truncated as a result of a frameshift mutation. Sequence analysis of the wobble variant showed a deletion of 9 amino acids from the C-terminus of the C1 CBH1a protein in the CBM region (the deleted residues are indicated below in bold font). An additional 7 amino acids changed identity due to the same causative frameshift (indicated by underlining).

```
CBH1a...SSGSSGPTGGTGVAKHYEQCGGIGFTGPTQCESPYTCTKLNDWYSQCL  (SEQ ID NO: 42)
                           .          :     .         :
Hit  ...SSGSSGPTGGTGVAKHYEQCGGIGFTGPTQCEARTLAPS           (SEQ ID NO: 43)
```

The effect of these changes on the function of the CBM would be expected to be substantial. Notably, disulfide bonds are formed by each of two pairs of cysteines at the CBH1a C-terminus (members of each pair are denoted above by "." and ":". In the truncated variant, one partner in each of the pairs is absent, likely resulting in improper folding. Additionally, two aromatic residues on the putative binding face have been removed (W521 and Y522). These changes are believed to result in a non-functional CBM.

The thermostabilities of the truncated variant (SEQ ID NO:21) and wild-type CBH1a (SEQ ID NO:2) were retested by expressing the proteins using the yeast shake flask process and carrying out MUL and biomass assays. In both assay formats, the truncated variant was found to have superior thermostability.

In the MUL assay, the wild-type CBH1a and the truncated variant were maintained for 2 hours at pH 4.4, 63° C., followed by addition of MUL and 1-hour reaction at pH 4.4, 62° C. to measure cellobiohydrolase activity. See Table 11.

TABLE 11

| Thermostability of truncated variant | |
|---|---|
| | Residual activity (% ± Std dev) |
| Wild-type CBH1a (SEQ ID NO: 2) | 15.8 ± 3.0 |
| Truncated variant (SEQ ID NO: 21) | 24.6 ± 4.0 |

In the biomass assays, the wild-type CBH1a and the truncated variant were maintained at pH 5, 50° C. for 17 hours in the presence of one of three substrates. The substrates were 37.5 g/L microcrystalline cellulose (Avicel), 5 g/L phosphoric acid-swollen cellulose (PASC), and 32.5 g/L pretreated wheat straw. Cellobiose production was measured by converting cellobiose to glucose using a β-glucosidase, and measuring glucose using a GOPOD-format assay. See Table 12.

TABLE 12

Cellobiose production of truncated variant

| | Glucose measured (g/L) | | |
|---|---|---|---|
| | Avicel | PASC | Wheat straw |
| Wild-type CBH1a (SEQ ID NO: 2) | 0.22 | 0.40 | 0.17 |
| Truncated variant (SEQ ID NO: 21) | 0.41 | 0.61 | 0.38 |

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

What is claimed is:

1. An isolated cellobiohydrolase type 1a (CBH1a) variant comprising an amino acid sequence at least 90% identical to SEQ ID NO:2 and comprising mutations at one or more of positions 58, 126, 286, and 294, wherein the positions are numbered with reference to SEQ ID NO:4.

2. The CBH1a variant of claim 1, wherein the mutation at position 58 is a substitution for threonine, the mutation at position 126 is a substitution for threonine, the mutation at position 286 is a substitution for glutamine, and/or the mutation at position 294 is a substitution for lysine.

3. The CBH1 a variant of claim 2, wherein the threonine at position 58 is replaced with isoleucine or valine (T581/V), the threonine at position 126 is replaced with valine (T126V), the glutamine at position 286 is replaced with methionine (Q286M), and/or the lysine at position 294 is replaced with proline (K294P).

4. The CBH1a variant of claim 1, comprising mutations at each of positions 24, 58, and 394, wherein the positions are numbered with reference to SEQ ID NO:4.

5. The CBH1 a variant of claim 4, wherein a threonine residue at position 24 is replaced with phenylalanine, isoleucine, lysine, leucine, asparagine, arginine, or valine (T24F/I/K/L/N/R/V);

a threonine residue at position 58 is replaced with isoleucine or valine (T581/V); and a valine residue at position 394 is replaced with alanine, aspartic acid, glycine, leucine, glutamine, or serine (V394A/D/G/L/Q/S).

6. The CBH1a variant of claim 1, comprising mutations at each of positions 58, 82, 177, and 417, wherein the positions are numbered with reference to SEQ ID NO:4.

7. The CBH1a variant of claim 6, wherein a threonine residue at position 58 is replaced with isoleucine or valine (T581/V);

a proline residue at position 82 is replaced with lysine or methionine (P82K/M);

a serine residue at position 177 is replaced with proline or glutamine (S177P/Q); and an alanine residue at position 417 is replaced with proline (A417P).

8. The CBH1a variant of claim 1, further comprising a mutation at position 381, wherein the position is numbered with reference to SEQ ID NO:4.

9. The CBH1a variant of claim 8, wherein the amino acid residue at position 381 is proline and is replaced with glycine (P381G).

10. The CBH1a variant of claim 1 comprising at least 95% sequence identity to SEQ ID NO:2.

11. The CBH1a variant of claim 1 that has increased thermostability after incubation at pH 4.4 and 66° C. for 2 hours in comparison to secreted wild-type CBH1a (SEQ ID NO:2).

12. An isolated recombinant cellobiohydrolase type 1a (CBH1a) variant comprising an amino acid sequence at least 80% identical to SEQ ID NO:2 and comprising one or more amino acid substitutions selected from X22H, X24F/I/K/L/N/R/V, X58I/V, X82K/M,X177P, X286M, X294P, X381 G, X394A/D/G/L/Q/S, and X417P, wherein the position is numbered with reference to SEQ ID NO:4, and wherein the cellobiohydrolase variant has increased thermostability in comparison to secreted wild-type CBH1a (SEQ ID NO:2).

13. An isolated enzyme composition comprising the CBH1a variant of claim 1.

14. The enzyme composition of claim 13, wherein the enzyme composition further comprises one or more of an endoglucanase (EG) polypeptide, a β-glucosidase (Bgl) polypeptide, a cellobiohydrolase type 2 (CBH2) polypeptide, and a glycoside hydrolase 61 (GH61) polypeptide.

15. A method of producing a fermentable sugar from a cellulosic substrate, comprising contacting the cellulosic substrate with the composition of claim 14 under conditions in which the fermentable sugar is produced.

16. The method of claim 15, further comprising contacting the fermentable sugar with a microorganism in a fermentation to produce an end-product.

* * * * *

UNITED STATES PATENT AND TRADEMARK OFFICE

CERTIFICATE OF CORRECTION

PATENT NO. : 8,759,064 B2
APPLICATION NO. : 13/107849
DATED : June 24, 2014
INVENTOR(S) : Mitchell et al.

It is certified that error appears in the above-identified patent and that said Letters Patent is hereby corrected as shown below:

In the Claims

Claim 12, column 168, line 39, delete "X22H"

Claim 12, column 168, line 40, between X82K/M and X177P insert -- X126V --

Signed and Sealed this
Ninth Day of September, 2014

Michelle K. Lee
*Deputy Director of the United States Patent and Trademark Office*

SEQUENCE LISTING

<160> NUMBER OF SEQ ID NOS: 43

<210> SEQ ID NO 1
<211> LENGTH: 1578
<212> TYPE: DNA
<213> ORGANISM: Myceliophthora thermophilia

<400> SEQUENCE: 1
atgtacgcca agttcgcgac cctcgccgcc cttgtggctg gcgccgctgc tcagaacgcc 60
tgcactctga ccgctgagaa ccacccctcg ctgacgtggt ccaagtgcac gtctggcggc 120
agctgcacca gcgtccaggg ttccatcacc atcgacgcca actggcggtg gactcaccgg 180
accgatagcg ccaccaactg ctacgagggc aacaagtggg atacttcgta ctgcagcgat 240
ggtccttctt gcgcctccaa gtgctgcatc gacggcgctg actactcgag cacctatggc 300
atcaccacga gcggtaactc cctgaacctc aagttcgtca ccaagggcca gtactcgacc 360
aacatcggct cgcgtaccta cctgatggag agcgacacca agtaccagat gttccagctc 420
ctcggcaacg agttcacctt cgatgtcgac gtctccaacc tcggctgcgg cctcaatggc 480
gccctctact tcgtgtccat ggatgccgat ggtggcatgt ccaagtactc gggcaacaag 540
gcaggtgcca agtacggtac cggctactgt gattctcagt gcccccgcga cctcaagttc 600
atcaacggcg aggccaacgt agagaactgg cagagctcga ccaacgatgc caacgccggc 660
acgggcaagt acggcagctg ctgctccgag atggacgtct gggaggccaa caacatggcc 720
gccgccttca ctccccaccc ttgcaccgtg atcggccagt cgcgctgcga gggcgactcg 780
tgcggcggta cctacagcac cgaccgctat gccggcatct gcgaccccga cggatgcgac 840
ttcaactcgt accgccaggg caacaagacc ttctacggca agggcatgac ggtcgacacg 900
accaagaaga tcacggtcgt cacccagttc ctcaagaact cggccggcga gctctccgag 960
atcaagcggt tctacgtcca gaacggcaag gtcatcccca actccgagtc caccatcccg 1020
ggcgtcgagg gcaactccat cacccaggac tggtgcgacc gccagaaggc cgccttcggc 1080
gacgtgaccg acttccagga caagggcggc atggtccaga tgggcaaggc cctcgcgggg 1140
cccatggtcc tcgtcatgtc catctgggac gaccacgccg tcaacatgct ctggctcgac 1200
tccacctggc ccatcgacgg cgccggcaag ccgggcgccg agcgcggtgc ctgccccacc 1260
acctcgggcg tccccgctga ggtcgaggcc gaggccccca actccaacgt catcttctcc 1320
aacatccgct tcggccccat cggctccacc gtctccggcc tgcccgacgg cggcagcggc 1380

-continued aaccccaacc cgcccgtcag ctcgtccacc ccggtcccct cctcgtccac cacatcctcc 1440
ggttcctccg gcccgactgg cggcacgggt gtcgctaagc actatgagca atgcggagga 1500
atcgggttca ctggccctac ccagtgcgag agcccctaca cttgcaccaa gctgaatgac 1560
tggtactcgc agtgcctg 1578

<210> SEQ ID NO 2
<211> LENGTH: 509
<212> TYPE: PRT
<213> ORGANISM: Myceliophthora thermophila

<400> SEQUENCE: 2

Gln Asn Ala Cys Thr Leu Thr Ala Glu Asn His Pro Ser Leu Thr Trp
1 5 10 15

Ser Lys Cys Thr Ser Gly Gly Ser Cys Thr Ser Val Gln Gly Ser Ile
20 25 30

Thr Ile Asp Ala Asn Trp Arg Trp Thr His Arg Thr Asp Ser Ala Thr
35 40 45

Asn Cys Tyr Glu Gly Asn Lys Trp Asp Thr Ser Tyr Cys Ser Asp Gly
50 55 60

Pro Ser Cys Ala Ser Lys Cys Cys Ile Asp Gly Ala Asp Tyr Ser Ser
65 70 75 80

Thr Tyr Gly Ile Thr Thr Ser Gly Asn Ser Leu Asn Leu Lys Phe Val
85 90 95

Thr Lys Gly Gln Tyr Ser Thr Asn Ile Gly Ser Arg Thr Tyr Leu Met
100 105 110

Glu Ser Asp Thr Lys Tyr Gln Met Phe Gln Leu Leu Gly Asn Glu Phe
115 120 125

Thr Phe Asp Val Asp Val Ser Asn Leu Gly Cys Gly Leu Asn Gly Ala
130 135 140

Leu Tyr Phe Val Ser Met Asp Ala Asp Gly Gly Met Ser Lys Tyr Ser
145 150 155 160

Gly Asn Lys Ala Gly Ala Lys Tyr Gly Thr Gly Tyr Cys Asp Ser Gln
165 170 175

Cys Pro Arg Asp Leu Lys Phe Ile Asn Gly Glu Ala Asn Val Glu Asn
180 185 190

Trp Gln Ser Ser Thr Asn Asp Ala Asn Ala Gly Thr Gly Lys Tyr Gly
195 200 205

Ser Cys Cys Ser Glu Met Asp Val Trp Glu Ala Asn Asn Met Ala Ala
210 215 220

Ala Phe Thr Pro His Pro Cys Thr Val Ile Gly Gln Ser Arg Cys Glu
225 230 235 240

Gly Asp Ser Cys Gly Gly Thr Tyr Ser Thr Asp Arg Tyr Ala Gly Ile
245 250 255

Cys Asp Pro Asp Gly Cys Asp Phe Asn Ser Tyr Arg Gln Gly Asn Lys
260 265 270

Thr Phe Tyr Gly Lys Gly Met Thr Val Asp Thr Thr Lys Lys Ile Thr
275 280 285

Val Val Thr Gln Phe Leu Lys Asn Ser Ala Gly Glu Leu Ser Glu Ile
290 295 300

Lys Arg Phe Tyr Val Gln Asn Gly Lys Val Ile Pro Asn Ser Glu Ser
305 310 315 320

Thr Ile Pro Gly Val Glu Gly Asn Ser Ile Thr Gln Asp Trp Cys Asp
325 330 335

Arg Gln Lys Ala Ala Phe Gly Asp Val Thr Asp Phe Gln Asp Lys Gly
340 345 350

Gly Met Val Gln Met Gly Lys Ala Leu Ala Gly Pro Met Val Leu Val
355 360 365

Met Ser Ile Trp Asp Asp His Ala Val Asn Met Leu Trp Leu Asp Ser
370 375 380

Thr Trp Pro Ile Asp Gly Ala Gly Lys Pro Gly Ala Glu Arg Gly Ala
385 390 395 400

Cys Pro Thr Thr Ser Gly Val Pro Ala Glu Val Glu Ala Glu Ala Pro
405 410 415

Asn Ser Asn Val Ile Phe Ser Asn Ile Arg Phe Gly Pro Ile Gly Ser
420 425 430

Thr Val Ser Gly Leu Pro Asp Gly Gly Ser Gly Asn Pro Asn Pro Pro
435 440 445

Val Ser Ser Ser Thr Pro Val Pro Ser Ser Ser Thr Thr Ser Ser Gly
450 455 460

Ser Ser Gly Pro Thr Gly Gly Thr Gly Val Ala Lys His Tyr Glu Gln
465 470 475 480

Cys Gly Gly Ile Gly Phe Thr Gly Pro Thr Gln Cys Glu Ser Pro Tyr
485 490 495

Thr Cys Thr Lys Leu Asn Asp Trp Tyr Ser Gln Cys Leu
500 505

<210> SEQ ID NO 3
<211> LENGTH: 17
<212> TYPE: PRT
<213> ORGANISM: Myceliophthora thermophila

<400> SEQUENCE: 3

Met Tyr Ala Lys Phe Ala Thr Leu Ala Ala Leu Val Ala Gly Ala Ala
1 5 10 15

Ala

<210> SEQ ID NO 4
<211> LENGTH: 526
<212> TYPE: PRT
<213> ORGANISM: Myceliophthora thermophila

<400> SEQUENCE: 4

Met Tyr Ala Lys Phe Ala Thr Leu Ala Ala Leu Val Ala Gly Ala Ala
1 5 10 15

Ala Gln Asn Ala Cys Thr Leu Thr Ala Glu Asn His Pro Ser Leu Thr
20 25 30

Trp Ser Lys Cys Thr Ser Gly Gly Ser Cys Thr Ser Val Gln Gly Ser
35 40 45

Ile Thr Ile Asp Ala Asn Trp Arg Trp Thr His Arg Thr Asp Ser Ala
50 55 60

Thr Asn Cys Tyr Glu Gly Asn Lys Trp Asp Thr Ser Tyr Cys Ser Asp
65 70 75 80

Gly Pro Ser Cys Ala Ser Lys Cys Cys Ile Asp Gly Ala Asp Tyr Ser
85 90 95

Ser Thr Tyr Gly Ile Thr Thr Ser Gly Asn Ser Leu Asn Leu Lys Phe
100 105 110

Val Thr Lys Gly Gln Tyr Ser Thr Asn Ile Gly Ser Arg Thr Tyr Leu
115 120 125

```
Met Glu Ser Asp Thr Lys Tyr Gln Met Phe Gln Leu Leu Gly Asn Glu
    130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Asn Trp Gln Ser Ser Thr Asn Asp Ala Asn Ala Gly Thr Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
        275                 280                 285

Lys Thr Phe Tyr Gly Lys Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
            340                 345                 350

Asp Arg Gln Lys Ala Ala Phe Gly Asp Val Thr Asp Phe Gln Asp Lys
        355                 360                 365

Gly Gly Met Val Gln Met Gly Lys Ala Leu Ala Gly Pro Met Val Leu
    370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
    450                 455                 460

Pro Val Ser Ser Ser Thr Pro Val Pro Ser Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525
```

<210> SEQ ID NO 5
<211> LENGTH: 538
<212> TYPE: PRT

-continued

<213> ORGANISM: Thielavia australiensis

<400> SEQUENCE: 5

```
Met Tyr Ala Lys Phe Ala Thr Leu Ala Ala Leu Val Ala Gly Ala Ser
1               5                   10                  15

Ala Gln Ala Val Cys Ser Leu Thr Ala Glu Thr His Pro Ser Leu Thr
            20                  25                  30

Trp Gln Lys Cys Thr Ala Pro Gly Ser Cys Thr Asn Val Ala Gly Ser
        35                  40                  45

Ile Thr Ile Asp Ala Asn Trp Arg Trp Thr His Gln Thr Ser Ser Ala
    50                  55                  60

Thr Asn Cys Tyr Ser Gly Ser Lys Trp Asp Ser Ser Ile Cys Thr Thr
65                  70                  75                  80

Gly Thr Asp Cys Ala Ser Lys Cys Cys Ile Asp Gly Ala Glu Tyr Ser
                85                  90                  95

Ser Thr Tyr Gly Ile Thr Thr Ser Gly Asn Ala Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Met Phe Lys Leu Leu Gly Asn Glu
    130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ala
            180                 185                 190

Gln Cys Pro Arg Asp Leu Lys Phe Ile Asn Gly Glu Ala Asn Val Glu
        195                 200                 205

Gly Trp Glu Ser Ser Thr Asn Asp Ala Asn Ala Gly Ser Gly Lys Tyr
    210                 215                 220

Gly Ser Cys Cys Thr Glu Met Asp Val Trp Glu Ala Asn Asn Met Ala
225                 230                 235                 240

Thr Ala Phe Thr Pro His Pro Cys Thr Thr Ile Gly Gln Thr Arg Cys
                245                 250                 255

Glu Gly Asp Thr Cys Gly Gly Thr Tyr Ser Ser Asp Arg Tyr Ala Gly
            260                 265                 270

Val Cys Asp Pro Asp Gly Cys Asp Phe Asn Ser Tyr Arg Gln Gly Asn
        275                 280                 285

Lys Thr Phe Tyr Gly Lys Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Ala Gln Asp Gly Lys Val Ile Pro Asn Ser Glu
                325                 330                 335

Ser Thr Ile Ala Gly Ile Pro Gly Asn Ser Ile Thr Lys Ala Tyr Cys
            340                 345                 350

Asp Ala Gln Lys Thr Val Phe Gln Asn Thr Asp Asp Phe Thr Ala Lys
        355                 360                 365

Gly Gly Leu Val Gln Met Gly Lys Ala Leu Ala Gly Asp Met Val Leu
    370                 375                 380

Val Met Ser Val Trp Asp Asp His Ala Val Asn Met Leu Trp Leu Asp
385                 390                 395                 400
```

```
Ser Thr Tyr Pro Thr Asp Gln Val Gly Val Ala Gly Ala Glu Arg Gly
                405                 410                 415

Ala Cys Pro Thr Thr Ser Gly Val Pro Ser Asp Val Glu Ala Asn Ala
            420                 425                 430

Pro Asn Ser Asn Val Ile Phe Ser Asn Ile Arg Phe Gly Pro Ile Gly
        435                 440                 445

Ser Thr Val Gln Gly Leu Pro Ser Ser Gly Gly Thr Ser Ser Ser Ser
    450                 455                 460

Ser Ala Ala Pro Gln Ser Thr Ser Thr Lys Ala Ser Thr Thr Thr Ser
465                 470                 475                 480

Ala Val Arg Thr Thr Ser Thr Ala Thr Thr Lys Thr Thr Ser Ser Ala
                485                 490                 495

Pro Ala Gln Gly Thr Asn Thr Ala Lys His Trp Gln Gln Cys Gly Gly
            500                 505                 510

Asn Gly Trp Thr Gly Pro Thr Val Cys Glu Ser Pro Tyr Lys Cys Thr
        515                 520                 525

Lys Gln Asn Asp Trp Tyr Ser Gln Cys Leu
    530                 535


<210> SEQ ID NO 6
<211> LENGTH: 525
<212> TYPE: PRT
<213> ORGANISM: Humicola grisea

<400> SEQUENCE: 6

Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
            20                  25                  30

Ser Trp Lys Lys Cys Thr Ala Gly Gly Gln Cys Gln Thr Val Gln Ala
        35                  40                  45

Ser Ile Thr Leu Asp Ser Asn Trp Arg Trp Thr His Gln Val Ser Gly
    50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

Phe Val Thr Lys Gly Gln Tyr Ser Thr Asn Val Gly Ser Arg Thr Tyr
        115                 120                 125

Leu Met Asp Gly Glu Asp Lys Tyr Gln Thr Phe Glu Leu Leu Gly Asn
    130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
            180                 185                 190

Ala Gln Cys Pro Arg Asp Ile Lys Phe Ile Asn Gly Glu Ala Asn Ile
        195                 200                 205

Glu Gly Trp Thr Gly Ser Thr Asn Asp Pro Asn Ala Gly Ala Gly Arg
    210                 215                 220

Tyr Gly Thr Cys Cys Ser Glu Met Asp Ile Trp Glu Ala Asn Asn Met
225                 230                 235                 240
```

-continued

Ala Thr Ala Phe Thr Pro His Pro Cys Thr Ile Ile Gly Gln Ser Arg
245 250 255

Cys Glu Gly Asp Ser Cys Gly Gly Thr Tyr Ser Asn Glu Arg Tyr Ala
260 265 270

Gly Val Cys Asp Pro Asp Gly Cys Asp Phe Asn Ser Tyr Arg Gln Gly
275 280 285

Asn Lys Thr Phe Tyr Gly Lys Gly Met Thr Val Asp Thr Thr Lys Lys
290 295 300

Ile Thr Val Val Thr Gln Phe Leu Lys Asp Ala Asn Gly Asp Leu Gly
305 310 315 320

Glu Ile Lys Arg Phe Tyr Val Gln Asp Gly Lys Ile Ile Pro Asn Ser
325 330 335

Glu Ser Thr Ile Pro Gly Val Glu Gly Asn Ser Ile Thr Gln Asp Trp
340 345 350

Cys Asp Arg Gln Lys Val Ala Phe Gly Asp Ile Asp Asp Phe Asn Arg
355 360 365

Lys Gly Gly Met Lys Gln Met Gly Lys Ala Leu Ala Gly Pro Met Val
370 375 380

Leu Val Met Ser Ile Trp Asp Asp His Ala Ser Asn Met Leu Trp Leu
385 390 395 400

Asp Ser Thr Phe Pro Val Asp Ala Ala Gly Lys Pro Gly Ala Glu Arg
405 410 415

Gly Ala Cys Pro Thr Thr Ser Gly Val Pro Ala Glu Val Glu Ala Glu
420 425 430

Ala Pro Asn Ser Asn Val Val Phe Ser Asn Ile Arg Phe Gly Pro Ile
435 440 445

Gly Ser Thr Val Ala Gly Leu Pro Gly Ala Gly Asn Gly Gly Asn Asn
450 455 460

Gly Gly Asn Pro Pro Pro Pro Thr Thr Thr Thr Ser Ser Ala Pro Ala
465 470 475 480

Thr Thr Thr Thr Ala Ser Ala Gly Pro Lys Ala Gly Arg Trp Gln Gln
485 490 495

Cys Gly Gly Ile Gly Phe Thr Gly Pro Thr Gln Cys Glu Glu Pro Tyr
500 505 510

Thr Cys Thr Lys Leu Asn Asp Trp Tyr Ser Gln Cys Leu
515 520 525

<210> SEQ ID NO 7
<211> LENGTH: 532
<212> TYPE: PRT
<213> ORGANISM: Chaetomium thermophilum

<400> SEQUENCE: 7

Met Met Tyr Lys Lys Phe Ala Ala Leu Ala Ala Leu Val Ala Gly Ala
1 5 10 15

Ser Ala Gln Gln Ala Cys Ser Leu Thr Ala Glu Asn His Pro Ser Leu
20 25 30

Thr Trp Lys Arg Cys Thr Ser Gly Gly Ser Cys Ser Thr Val Asn Gly
35 40 45

Ala Val Thr Ile Asp Ala Asn Trp Arg Trp Thr His Thr Val Ser Gly
50 55 60

Ser Thr Asn Cys Tyr Thr Gly Asn Gln Trp Asp Thr Ser Leu Cys Thr
65 70 75 80

Asp Gly Lys Ser Cys Ala Gln Thr Cys Cys Val Asp Gly Ala Asp Tyr

-continued

```
            85                  90                  95

Ser Ser Thr Tyr Gly Ile Thr Thr Ser Gly Asp Ser Leu Asn Leu Lys
            100                 105                 110

Phe Val Thr Lys His Gln Tyr Gly Thr Asn Val Gly Ser Arg Val Tyr
        115                 120                 125

Leu Met Glu Asn Asp Thr Lys Tyr Gln Met Phe Glu Leu Leu Gly Asn
    130                 135                 140

Glu Phe Thr Phe Asp Val Asp Val Ser Asn Leu Gly Cys Gly Leu Asn
145                 150                 155                 160

Gly Ala Leu Tyr Phe Val Ser Met Asp Ala Asp Gly Gly Met Ser Lys
                165                 170                 175

Tyr Ser Gly Asn Lys Ala Gly Ala Lys Tyr Gly Thr Gly Tyr Cys Asp
            180                 185                 190

Ala Gln Cys Pro Arg Asp Leu Lys Phe Ile Asn Gly Glu Ala Asn Val
        195                 200                 205

Gly Asn Trp Thr Pro Ser Thr Asn Asp Ala Asn Ala Gly Phe Gly Arg
    210                 215                 220

Tyr Gly Ser Cys Cys Ser Glu Met Asp Val Trp Glu Ala Asn Asn Met
225                 230                 235                 240

Ala Thr Ala Phe Thr Pro His Pro Cys Thr Thr Val Gly Gln Ser Arg
                245                 250                 255

Cys Glu Ala Asp Thr Cys Gly Gly Thr Tyr Ser Ser Asp Arg Tyr Ala
            260                 265                 270

Gly Val Cys Asp Pro Asp Gly Cys Asp Phe Asn Ala Tyr Arg Gln Gly
        275                 280                 285

Asp Lys Thr Phe Tyr Gly Lys Gly Met Thr Val Asp Thr Asn Lys Lys
    290                 295                 300

Met Thr Val Val Thr Gln Phe His Lys Asn Ser Ala Gly Val Leu Ser
305                 310                 315                 320

Glu Ile Lys Arg Phe Tyr Val Gln Asp Gly Lys Ile Ile Ala Asn Ala
                325                 330                 335

Glu Ser Lys Ile Pro Gly Asn Pro Gly Asn Ser Ile Thr Gln Glu Tyr
            340                 345                 350

Cys Asp Ala Gln Lys Val Ala Phe Ser Asn Thr Asp Asp Phe Asn Arg
        355                 360                 365

Lys Gly Gly Met Ala Gln Met Ser Lys Ala Leu Ala Gly Pro Met Val
    370                 375                 380

Leu Val Met Ser Val Trp Asp Asp His Tyr Ala Asn Met Leu Trp Leu
385                 390                 395                 400

Asp Ser Thr Tyr Pro Ile Asp Gln Ala Gly Ala Pro Gly Ala Glu Arg
                405                 410                 415

Gly Ala Cys Pro Thr Thr Ser Gly Val Pro Ala Glu Ile Glu Ala Gln
            420                 425                 430

Val Pro Asn Ser Asn Val Ile Phe Ser Asn Ile Arg Phe Gly Pro Ile
        435                 440                 445

Gly Ser Thr Val Pro Gly Leu Asp Gly Ser Asn Pro Gly Asn Pro Thr
    450                 455                 460

Thr Thr Val Val Pro Pro Ala Ser Thr Ser Thr Ser Arg Pro Thr Ser
465                 470                 475                 480

Ser Thr Ser Ser Pro Val Ser Thr Pro Thr Gly Gln Pro Gly Gly Cys
                485                 490                 495

Thr Thr Gln Lys Trp Gly Gln Cys Gly Gly Ile Gly Tyr Thr Gly Cys
            500                 505                 510
```

```
Thr Asn Cys Val Ala Gly Thr Thr Cys Thr Gln Leu Asn Pro Trp Tyr
        515                 520                 525

Ser Gln Cys Leu
    530


<210> SEQ ID NO 8
<211> LENGTH: 522
<212> TYPE: PRT
<213> ORGANISM: Sordaria macrospora

<400> SEQUENCE: 8

Met Leu Ala Lys Phe Ala Ala Leu Ala Ala Leu Val Ala Ser Ala Asn
1               5                   10                  15

Ala Gln Ala Val Cys Ser Leu Thr Ala Glu Thr His Pro Ser Leu Asn
            20                  25                  30

Trp Ser Lys Cys Thr Ser Ser Gly Cys Thr Asn Val Ala Gly Ser Val
        35                  40                  45

Thr Ile Asp Ala Asn Trp Arg Trp Thr His Thr Leu Ser Gly Ser Thr
    50                  55                  60

Asn Cys Tyr Asn Gly Asn Lys Trp Asp Thr Thr Ile Cys Ser Thr Asn
65                  70                  75                  80

Thr Asp Cys Ala Thr Lys Cys Cys Val Asp Gly Ala Glu Tyr Ser Ser
                85                  90                  95

Thr Tyr Gly Ile Gln Thr Ser Gly Asn Ser Leu Ser Leu Gln Phe Val
            100                 105                 110

Thr Lys Gly Gln Tyr Ser Thr Asn Ile Gly Ser Arg Thr Tyr Leu Met
        115                 120                 125

Asn Gly Asn Asp Ala Tyr Gln Gly Phe Glu Leu Leu Gly Asn Glu Phe
    130                 135                 140

Thr Phe Asp Val Asp Val Ser Gly Thr Gly Cys Gly Leu Asn Gly Ala
145                 150                 155                 160

Leu Tyr Phe Val Ser Met Asp Leu Asp Gly Gly Lys Ser Lys Tyr Ser
                165                 170                 175

Thr Asn Lys Ala Gly Ala Lys Tyr Gly Thr Gly Tyr Cys Asp Ala Gln
            180                 185                 190

Cys Pro Arg Asp Leu Lys Tyr Ile Asn Gly Val Gly Asn Val Glu Gly
        195                 200                 205

Trp Ser Ser Ser Thr Asn Asp Pro Asn Ala Gly Ile Gly Asn His Gly
    210                 215                 220

Thr Cys Cys Ser Glu Met Asp Ile Trp Glu Ala Asn Lys Val Ser Thr
225                 230                 235                 240

Ala Phe Thr Pro His Pro Cys Thr Thr Ile Asp Gln His Met Cys Glu
                245                 250                 255

Gly Asn Ser Cys Gly Gly Thr Tyr Ser Thr Asp Arg Tyr Gly Gly Thr
            260                 265                 270

Cys Asp Ala Asp Gly Cys Asp Phe Asn Ser Tyr Arg Met Gly Asn Thr
        275                 280                 285

Thr Phe Tyr Gly Glu Gly Lys Thr Val Asp Thr Arg Ser Lys Phe Thr
    290                 295                 300

Val Val Thr Gln Phe Ile Lys Asn Ser Ala Gly Asp Leu Gly Glu Ile
305                 310                 315                 320

Lys Arg Phe Tyr Val Gln Asn Gly Lys Val Ile Glu Asn Ser Gln Ser
                325                 330                 335

Asn Ile Ala Gly Val Ser Gly Asn Ser Ile Thr Gln Ser Phe Cys Asp
```

340 345 350

Ala Gln Lys Thr Ala Phe Gly Asp Val Gly Asp Phe Asn Val Lys Gly
355 360 365

Gly Leu Lys Gln Met Gly Lys Ala Leu Ala Lys Pro Met Val Leu Val
370 375 380

Met Ser Ile Trp Asp Asp His Ala Ala Asn Met Leu Trp Leu Asp Ser
385 390 395 400

Thr Tyr Pro Val Glu Gly Gly Ser Pro Gly Ala Tyr Arg Gly Glu Cys
405 410 415

Pro Thr Thr Ser Gly Val Pro Ala Glu Val Glu Ala Asn Ala Pro Asn
420 425 430

Ser Lys Val Ile Phe Ser Asn Ile Lys Phe Gly Pro Ile Gly Ser Thr
435 440 445

Phe Ser Gly Gly Ser Ser Gly Gly Thr Pro Ser Asn Pro Ser Ser Ser
450 455 460

Val Lys Pro Val Thr Ser Thr Ala Lys Pro Thr Thr Thr Ser Thr Ala
465 470 475 480

Ser Asn Pro Ser Gly Thr Gly Ala Ala His Trp Ala Gln Cys Gly Gly
485 490 495

Ile Gly Phe Asn Gly Pro Thr Thr Cys Gln Ser Pro Tyr Thr Cys Gln
500 505 510

Lys Ile Asn Asp Tyr Tyr Ser Gln Cys Leu
515 520

<210> SEQ ID NO 9
<211> LENGTH: 532
<212> TYPE: PRT
<213> ORGANISM: Chaetomidium pingtungium

<400> SEQUENCE: 9

Met Leu Ala Ser Thr Phe Ser Tyr Arg Met Tyr Lys Thr Ala Leu Ile
1 5 10 15

Leu Ala Ala Leu Leu Gly Ser Gly Gln Ala Gln Gln Val Gly Thr Ser
20 25 30

Gln Ala Glu Val His Pro Ser Met Thr Trp Gln Ser Cys Thr Ala Gly
35 40 45

Gly Ser Cys Thr Thr Asn Asn Gly Lys Val Val Ile Asp Ala Asn Trp
50 55 60

Arg Trp Val His Lys Val Gly Asp Tyr Thr Asn Cys Tyr Thr Gly Asn
65 70 75 80

Thr Trp Asp Thr Thr Ile Cys Pro Asp Asp Ala Thr Cys Ala Ser Asn
85 90 95

Cys Ala Leu Glu Gly Ala Asn Tyr Glu Ser Thr Tyr Gly Val Thr Ala
100 105 110

Ser Gly Asn Ser Leu Arg Leu Asn Phe Val Thr Thr Ser Gln Gln Lys
115 120 125

Asn Ile Gly Ser Arg Leu Tyr Met Met Lys Asp Asp Ser Thr Tyr Glu
130 135 140

Met Phe Lys Leu Leu Asn Gln Glu Phe Thr Phe Asp Val Asp Val Ser
145 150 155 160

Asn Leu Pro Cys Gly Leu Asn Gly Ala Leu Tyr Phe Val Ala Met Asp
165 170 175

Ala Gly Gly Gly Met Ser Lys Tyr Pro Thr Asn Lys Ala Gly Ala Lys
180 185 190

```
Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
        515                 520                 525

Ser Gln Cys Leu
    530


<210> SEQ ID NO 10
<211> LENGTH: 454
<212> TYPE: PRT
<213> ORGANISM: Botryosphaeria rhodina

<400> SEQUENCE: 10

Met Leu Thr Gln Ala Val Leu Ala Thr Leu Ala Thr Leu Ala Ala Ser
1               5                   10                  15

Gln Gln Val Gly Thr Gln Lys Glu Glu Val His Pro Ser Met Thr Trp
            20                  25                  30
```

-continued

```
Gln Thr Cys Thr Ser Ser Gly Cys Thr Thr Asn Gln Gly Ser Ile Val
        35                  40                  45

Val Asp Ala Asn Trp Arg Trp Val His Asn Thr Glu Gly Tyr Thr Asn
    50                  55                  60

Cys Tyr Thr Gly Asn Thr Trp Asn Ala Asp Tyr Cys Thr Asp Asn Thr
65                  70                  75                  80

Glu Cys Ala Ser Asn Cys Ala Leu Asp Gly Ala Asp Tyr Ser Gly Thr
                85                  90                  95

Tyr Gly Ala Thr Thr Ser Gly Asp Ser Leu Arg Leu Asn Phe Ile Thr
            100                 105                 110

Asn Gly Gln Gln Lys Asn Ile Gly Ser Arg Met Tyr Leu Met Gln Asp
        115                 120                 125

Asp Glu Thr Tyr Ala Val His Lys Leu Leu Asn Lys Glu Phe Thr Phe
    130                 135                 140

Asp Val Asp Thr Ser Lys Leu Pro Cys Gly Leu Asn Gly Ala Val Tyr
145                 150                 155                 160

Phe Val Ser Met Asp Ala Asp Gly Gly Met Ala Lys Phe Pro Asp Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Lys Ala Asn Val Glu Gly Trp Val
        195                 200                 205

Pro Ser Glu Asn Asp Ser Asn Ala Gly Val Gly Asn Leu Gly Ser Cys
    210                 215                 220

Cys Ala Glu Met Asp Ile Trp Glu Ala Asn Ser Ile Ser Thr Ala Tyr
225                 230                 235                 240

Thr Pro His Ser Cys Lys Thr Val Ala Gln His Ser Cys Thr Gly Asp
                245                 250                 255

Asp Cys Gly Gly Thr Tyr Ser Ala Thr Arg Tyr Ala Gly Asp Cys Asp
            260                 265                 270

Pro Asp Gly Cys Asp Phe Asn Ser Tyr Arg Gln Gly Val Lys Asp Phe
        275                 280                 285

Tyr Gly Pro Gly Met Thr Val Asp Ser Asn Ser Val Val Thr Val Val
    290                 295                 300

Thr Gln Phe Ile Thr Asn Asp Gly Thr Ala Ser Gly Thr Leu Ser Glu
305                 310                 315                 320

Ile Lys Arg Phe Tyr Val Gln Asn Gly Lys Val Ile Pro Asn Ser Glu
                325                 330                 335

Ser Thr Ile Ala Gly Val Ser Gly Asn Ser Ile Thr Ser Ala Tyr Cys
            340                 345                 350

Asp Ala Gln Lys Glu Val Phe Gly Asp Asn Thr Ser Phe Gln Asp Gln
        355                 360                 365

Gly Gly Leu Ala Ser Met Ser Gln Ala Leu Asn Ala Gly Met Val Leu
    370                 375                 380

Val Met Ser Ile Trp Asp Asp His His Ser Asn Met Leu Trp Leu Asp
385                 390                 395                 400

Ser Asp Tyr Pro Val Asp Ala Asp Pro Ser Gln Pro Gly Ile Ser Arg
                405                 410                 415

Gly Thr Cys Pro Thr Thr Ser Gly Val Pro Ser Glu Val Glu Glu Ser
            420                 425                 430

Ala Ala Ser Ala Tyr Val Val Tyr Ser Asn Ile Lys Val Gly Asp Leu
        435                 440                 445
```

```
Asn Ser Thr Phe Ser Ala
    450


<210> SEQ ID NO 11
<211> LENGTH: 458
<212> TYPE: PRT
<213> ORGANISM: Trichophaea saccata

<400> SEQUENCE: 11

Met Gln Arg Leu Leu Val Leu Leu Thr Ser Leu Leu Ala Phe Thr Tyr
1               5                   10                  15

Gly Gln Gln Val Gly Thr Gln Gln Ala Glu Val His Pro Ser Met Thr
            20                  25                  30

Trp Gln Gln Cys Thr Lys Ser Gly Gly Cys Thr Thr Lys Asn Gly Lys
        35                  40                  45

Val Val Ile Asp Ala Asn Trp Arg Trp Val His Asn Val Gly Gly Tyr
    50                  55                  60

Thr Asn Cys Tyr Thr Gly Asn Thr Trp Asp Ser Ser Leu Cys Pro Asp
65                  70                  75                  80

Asp Val Thr Cys Ala Lys Asn Cys Ala Leu Asp Gly Ala Asp Tyr Ser
                85                  90                  95

Gly Thr Tyr Gly Val Thr Ala Gly Gly Asn Ser Leu Lys Leu Thr Phe
            100                 105                 110

Val Thr Lys Gly Gln Tyr Ser Thr Asn Val Gly Ser Arg Leu Tyr Met
        115                 120                 125

Leu Ala Asp Asp Ser Thr Tyr Gln Met Tyr Asn Leu Leu Asn Gln Glu
    130                 135                 140

Phe Thr Phe Asp Val Asp Val Ser Asn Leu Pro Cys Gly Leu Asn Gly
145                 150                 155                 160

Ala Leu Tyr Phe Val Ser Met Asp Lys Asp Gly Gly Met Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Gln Gly Asn Val Glu
        195                 200                 205

Gly Trp Lys Pro Ser Ser Asn Asp Ala Asn Ala Gly Val Gly Gly His
    210                 215                 220

Gly Ser Cys Cys Ala Glu Met Asp Val Trp Glu Ala Asn Ser Ile Ser
225                 230                 235                 240

Ala Ala Val Thr Pro His Ser Cys Ser Thr Thr Ser Gln Thr Met Cys
                245                 250                 255

Asn Gly Asp Ser Cys Gly Gly Thr Tyr Ser Ala Thr Arg Tyr Ala Gly
            260                 265                 270

Val Cys Asp Pro Asp Gly Cys Asp Phe Asn Ser Tyr Arg Met Gly Asp
        275                 280                 285

Thr Thr Phe Tyr Gly Lys Gly Lys Thr Val Asp Thr Ser Ser Lys Phe
    290                 295                 300

Thr Val Val Thr Gln Phe Ile Thr Asp Thr Gly Thr Ala Ser Gly Ser
305                 310                 315                 320

Leu Thr Glu Ile Arg Arg Phe Tyr Val Gln Asn Gly Lys Leu Ile Pro
                325                 330                 335

Asn Ser Gln Ser Lys Ile Ser Gly Val Thr Gly Asn Ser Ile Thr Ser
            340                 345                 350

Ala Phe Cys Asp Ala Gln Lys Ala Ala Phe Gly Asp Asn Tyr Thr Phe
        355                 360                 365
```

```
Lys Asp Lys Gly Gly Phe Ala Ser Met Thr Thr Ala Met Lys Asn Gly
    370                 375                 380

Met Val Leu Val Met Ser Leu Trp Asp Asp His Tyr Ala Asn Met Leu
385                 390                 395                 400

Trp Leu Asp Ser Asp Tyr Pro Thr Asn Ala Asp Ser Ser Lys Pro Gly
                405                 410                 415

Val Ala Arg Gly Thr Cys Pro Thr Ser Ser Gly Val Pro Ser Asp Val
            420                 425                 430

Glu Thr Asn Asn Ala Ser Ala Ser Val Thr Tyr Ser Asn Ile Arg Phe
        435                 440                 445

Gly Asp Leu Asn Ser Thr Tyr Thr Ala Gln
    450                 455


<210> SEQ ID NO 12
<211> LENGTH: 526
<212> TYPE: PRT
<213> ORGANISM: Aspergillus nidulans

<400> SEQUENCE: 12

Met Ala Ser Ser Phe Gln Leu Tyr Lys Ala Leu Leu Phe Phe Ser Ser
1               5                   10                  15

Leu Leu Ser Ala Val Gln Ala Gln Lys Val Gly Thr Gln Gln Ala Glu
            20                  25                  30

Val His Pro Gly Leu Thr Trp Gln Thr Cys Thr Ser Ser Gly Ser Cys
        35                  40                  45

Thr Thr Val Asn Gly Glu Val Thr Ile Asp Ala Asn Trp Arg Trp Leu
    50                  55                  60

His Thr Val Asn Gly Tyr Thr Asn Cys Tyr Thr Gly Asn Glu Trp Asp
65                  70                  75                  80

Thr Ser Ile Cys Thr Ser Asn Glu Val Cys Ala Glu Gln Cys Ala Val
                85                  90                  95

Asp Gly Ala Asn Tyr Ala Ser Thr Tyr Gly Ile Thr Thr Ser Gly Ser
            100                 105                 110

Ser Leu Arg Leu Asn Phe Val Thr Gln Ser Gln Gln Lys Asn Ile Gly
        115                 120                 125

Ser Arg Val Tyr Leu Met Asp Asp Glu Asp Thr Tyr Thr Met Phe Tyr
    130                 135                 140

Leu Leu Asn Lys Glu Phe Thr Phe Asp Val Asp Val Ser Glu Leu Pro
145                 150                 155                 160

Cys Gly Leu Asn Gly Ala Val Tyr Phe Val Ser Met Asp Ala Asp Gly
                165                 170                 175

Gly Lys Ser Arg Tyr Ala Thr Asn Glu Ala Gly Ala Lys Tyr Gly Thr
            180                 185                 190

Gly Tyr Cys Asp Ser Gln Cys Pro Arg Asp Leu Lys Phe Ile Asn Gly
        195                 200                 205

Val Ala Asn Val Glu Gly Trp Glu Ser Ser Asp Thr Asn Pro Asn Gly
    210                 215                 220

Gly Val Gly Asn His Gly Ser Cys Cys Ala Glu Met Asp Ile Trp Glu
225                 230                 235                 240

Ala Asn Ser Ile Ser Thr Ala Phe Thr Pro His Pro Cys Asp Thr Pro
                245                 250                 255

Gly Gln Thr Leu Cys Thr Gly Asp Ser Cys Gly Gly Thr Tyr Ser Asn
            260                 265                 270

Asp Arg Tyr Gly Gly Thr Cys Asp Pro Asp Gly Cys Asp Phe Asn Ser
```

```
        275                 280                 285

Tyr Arg Gln Gly Asn Lys Thr Phe Tyr Gly Pro Gly Leu Thr Val Asp
    290                 295                 300

Thr Asn Ser Pro Val Thr Val Val Thr Gln Phe Leu Thr Asp Asp Asn
305                 310                 315                 320

Thr Asp Thr Gly Thr Leu Ser Glu Ile Lys Arg Phe Tyr Val Gln Asn
                325                 330                 335

Gly Val Val Ile Pro Asn Ser Glu Ser Thr Tyr Pro Ala Asn Pro Gly
            340                 345                 350

Asn Ser Ile Thr Thr Glu Phe Cys Glu Ser Gln Lys Glu Leu Phe Gly
        355                 360                 365

Asp Val Asp Val Phe Ser Ala His Gly Gly Met Ala Gly Met Gly Ala
    370                 375                 380

Ala Leu Glu Gln Gly Met Val Leu Val Leu Ser Leu Trp Asp Asp Asn
385                 390                 395                 400

Tyr Ser Asn Met Leu Trp Leu Asp Ser Asn Tyr Pro Thr Asp Ala Asp
                405                 410                 415

Pro Thr Gln Pro Gly Ile Ala Arg Gly Thr Cys Pro Thr Asp Ser Gly
            420                 425                 430

Val Pro Ser Glu Val Glu Ala Gln Tyr Pro Asn Ala Tyr Val Val Tyr
        435                 440                 445

Ser Asn Ile Lys Phe Gly Pro Ile Gly Ser Thr Phe Gly Asn Gly Gly
    450                 455                 460

Gly Ser Gly Pro Thr Thr Thr Val Thr Thr Ser Thr Ala Thr Ser Thr
465                 470                 475                 480

Thr Ser Ser Ala Thr Ser Thr Ala Thr Gly Gln Ala Gln His Trp Glu
                485                 490                 495

Gln Cys Gly Gly Asn Gly Trp Thr Gly Pro Thr Val Cys Ala Ser Pro
            500                 505                 510

Trp Ala Cys Thr Val Val Asn Ser Trp Tyr Ser Gln Cys Leu
        515                 520                 525


<210> SEQ ID NO 13
<211> LENGTH: 455
<212> TYPE: PRT
<213> ORGANISM: Schizophyllum commune

<400> SEQUENCE: 13

Met Phe Pro Ala Ala Ala Leu Val Ser Leu Thr Leu Ala Ala Ile Ala
1               5                   10                  15

Arg Ala Gln Gln Val Gly Asn Leu Thr Ala Glu Thr His Pro Ser Leu
            20                  25                  30

Ser Trp Gln Glu Cys Thr Ser Ser Gly Cys Thr Asp His Ser Ala Ala
        35                  40                  45

Ile Thr Ile Asp Ala Asn Trp Arg Trp Leu His Thr Val Glu Gly Tyr
    50                  55                  60

Asp Asn Cys Tyr Thr Gly Asn Glu Trp Asp Glu Ser Val Cys Thr Asp
65                  70                  75                  80

Gly Ala Thr Cys Ala Ser Ser Cys Ala Leu Asp Gly Ala Asp Tyr Ser
                85                  90                  95

Gly Thr Tyr Gly Ile Thr Thr Ser Gly Asp Ala Leu Ser Leu Lys Phe
            100                 105                 110

Val Thr Ser Gly Gln Gln Lys Asn Ile Gly Ser Arg Thr Tyr Leu Met
        115                 120                 125
```

```
Asn Gly Glu Asp Lys Tyr Gln Met Phe Lys Leu Lys Asn Lys Glu Phe
    130                 135                 140

Thr Phe Thr Val Asp Met Ser Thr Leu Pro Cys Gly Leu Asn Gly Ala
145                 150                 155                 160

Leu Tyr Phe Val Glu Met Asp Glu Asp Gly Gly Val Ser Lys Tyr Pro
                165                 170                 175

Thr Asn Lys Ala Gly Ala Lys Tyr Gly Thr Gly Tyr Cys Asp Ser Gln
            180                 185                 190

Cys Pro His Asp Ile Lys Phe Ile Asn Gly Glu Ala Asn Ser Glu Gly
        195                 200                 205

Trp Ala Gly Ser Asp Asn Asp Pro Asn Ala Gly Thr Gly Thr Tyr Gly
    210                 215                 220

Ser Cys Cys Ser Glu Met Asp Ile Trp Glu Ala Asn Ser Gln Ala Ala
225                 230                 235                 240

Ala Tyr Thr Pro His Val Cys Thr Val Glu Gly Gln Thr Arg Cys Glu
                245                 250                 255

Gly Thr Asp Cys Gly Asp Asp Asp Asp Arg Tyr Ser Gly Val Cys Asp
            260                 265                 270

Lys Asp Gly Cys Asp Phe Asn Ser Tyr Arg Met Gly Asp Thr Thr Phe
        275                 280                 285

Leu Gly Glu Gly Leu Thr Ile Asp Thr Thr Gln Pro Ile Thr Val Val
    290                 295                 300

Thr Gln Phe Ile Thr Ala Asp Asn Thr Thr Ser Gly Ala Leu Ser Glu
305                 310                 315                 320

Ile Arg Arg Leu Tyr Val Gln Gly Gly Glu Val Val Ala Asn Ser Ala
                325                 330                 335

Thr Lys Ile Glu Gly Leu Asp Asp Tyr Asp Ser Ile Thr Asp Gln Phe
            340                 345                 350

Cys Ala Asp Gln Lys Glu Val Phe Gly Asp Gln Asn Tyr Phe Gly Thr
        355                 360                 365

Leu Gly Gly Leu Glu Ala Met Gly Glu Ser Leu Asp Arg Gly His Val
    370                 375                 380

Leu Val Met Ser Ile Trp Asp Asp His Ala Val Asn Met Leu Trp Leu
385                 390                 395                 400

Asp Ser Asp Tyr Pro Leu Asp Lys Asp Pro Ser Glu Pro Gly Val Ser
                405                 410                 415

Arg Gly Pro Cys Gly Thr Asp Ser Gly Val Pro Thr Asp Val Glu Ala
            420                 425                 430

Gln Ser Pro Asp Ala Thr Val Ile Tyr Ser Ala Ile Lys Phe Gly Asp
        435                 440                 445

Ile Gly Thr Thr Tyr Ser Ala
    450                 455
```

<210> SEQ ID NO 14
<211> LENGTH: 506
<212> TYPE: PRT
<213> ORGANISM: Agaricus bisporus

<400> SEQUENCE: 14

```
Met Phe Pro Arg Ser Ile Leu Leu Ala Leu Ser Leu Thr Ala Val Ala
1               5                   10                  15

Leu Gly Gln Gln Val Gly Thr Asn Met Ala Glu Asn His Pro Ser Leu
            20                  25                  30

Thr Trp Gln Arg Cys Thr Ser Ser Gly Cys Gln Asn Val Asn Gly Lys
        35                  40                  45
```

-continued

```
Val Thr Leu Asp Ala Asn Trp Arg Trp Thr His Arg Ile Asn Asp Phe
    50                  55                  60

Thr Asn Cys Tyr Thr Gly Asn Glu Trp Asp Thr Ser Ile Cys Pro Asp
65                  70                  75                  80

Gly Val Thr Cys Ala Glu Asn Cys Ala Leu Asp Gly Ala Asp Tyr Ala
                85                  90                  95

Gly Thr Tyr Gly Val Thr Ser Ser Gly Thr Ala Leu Thr Leu Lys Phe
            100                 105                 110

Val Thr Glu Ser Gln Gln Lys Asn Ile Gly Ser Arg Leu Tyr Leu Met
        115                 120                 125

Ala Asp Asp Ser Asn Tyr Glu Ile Phe Asn Leu Leu Asn Lys Glu Phe
    130                 135                 140

Thr Phe Asp Val Asp Val Ser Lys Leu Pro Cys Gly Leu Asn Gly Ala
145                 150                 155                 160

Leu Tyr Phe Ser Glu Met Ala Ala Asp Gly Gly Met Ser Ser Thr Asn
                165                 170                 175

Thr Ala Gly Ala Lys Tyr Gly Thr Gly Tyr Cys Asp Ser Gln Cys Pro
            180                 185                 190

Arg Asp Ile Lys Phe Ile Asp Gly Glu Ala Asn Ser Glu Gly Trp Glu
        195                 200                 205

Gly Ser Pro Asn Asp Val Asn Ala Gly Thr Gly Asn Phe Gly Ala Cys
    210                 215                 220

Cys Gly Glu Met Asp Ile Trp Glu Ala Asn Ser Ile Ser Ser Ala Tyr
225                 230                 235                 240

Thr Pro His Pro Cys Arg Glu Pro Gly Leu Gln Arg Cys Glu Gly Asn
                245                 250                 255

Thr Cys Ser Val Asn Asp Arg Tyr Ala Thr Glu Cys Asp Pro Asp Gly
            260                 265                 270

Cys Asp Phe Asn Ser Phe Arg Met Gly Asp Lys Ser Phe Tyr Gly Pro
        275                 280                 285

Gly Met Thr Val Asp Thr Asn Gln Pro Ile Thr Val Val Thr Gln Phe
    290                 295                 300

Ile Thr Asp Asn Gly Ser Asp Asn Gly Asn Leu Gln Glu Ile Arg Arg
305                 310                 315                 320

Ile Tyr Val Gln Asn Gly Gln Val Ile Gln Asn Ser Asn Val Asn Ile
                325                 330                 335

Pro Gly Ile Asp Ser Gly Asn Ser Ile Ser Ala Glu Phe Cys Asp Gln
            340                 345                 350

Ala Lys Glu Ala Phe Gly Asp Glu Arg Ser Phe Gln Asp Arg Gly Gly
        355                 360                 365

Leu Ser Gly Met Gly Ser Ala Leu Asp Arg Gly Met Val Leu Val Leu
    370                 375                 380

Ser Ile Trp Asp Asp His Ala Val Asn Met Leu Trp Leu Asp Ser Asp
385                 390                 395                 400

Tyr Pro Leu Asp Ala Ser Pro Ser Gln Pro Gly Ile Ser Arg Gly Thr
                405                 410                 415

Cys Ser Arg Asp Ser Gly Lys Pro Glu Asp Val Glu Ala Asn Ala Gly
            420                 425                 430

Gly Val Gln Val Val Tyr Ser Asn Ile Lys Phe Gly Asp Ile Asn Ser
        435                 440                 445

Thr Phe Asn Asn Asn Gly Gly Gly Gly Gly Asn Pro Ser Pro Thr Thr
    450                 455                 460
```

```
Thr Arg Pro Asn Ser Pro Ala Gln Thr Met Trp Gly Gln Cys Gly Gly
465                 470                 475                 480

Gln Gly Trp Thr Gly Pro Thr Ala Cys Gln Ser Pro Ser Thr Cys His
                485                 490                 495

Val Ile Asn Asp Phe Tyr Ser Gln Cys Phe
            500                 505


<210> SEQ ID NO 15
<211> LENGTH: 8
<212> TYPE: PRT
<213> ORGANISM: Artificial Sequence
<220> FEATURE:
<223> OTHER INFORMATION: Synthetic polypeptide for cellobiohydrolase
      glutamine-containing Q117 motif
<220> FEATURE:
<221> NAME/KEY: VARIANT
<222> LOCATION: (2)..(3)
<223> OTHER INFORMATION: Xaa = any amino acid, may be present or absent
<220> FEATURE:
<221> NAME/KEY: VARIANT
<222> LOCATION: (5)..(6)
<223> OTHER INFORMATION: Xaa = any amino acid
<220> FEATURE:
<221> NAME/KEY: VARIANT
<222> LOCATION: (7)..(7)
<223> OTHER INFORMATION: Xaa = any amino acid, may be present or absent

<400> SEQUENCE: 15

Thr Xaa Xaa Gln Xaa Xaa Xaa Asn
1               5


<210> SEQ ID NO 16
<211> LENGTH: 8
<212> TYPE: PRT
<213> ORGANISM: Artificial Sequence
<220> FEATURE:
<223> OTHER INFORMATION: Synthetic polypeptide of cellobiohydrolase
      glutamine-containing Q117 motif
<220> FEATURE:
<221> NAME/KEY: VARIANT
<222> LOCATION: (2)..(3)
<223> OTHER INFORMATION: Xaa = any amino acid
<220> FEATURE:
<221> NAME/KEY: VARIANT
<222> LOCATION: (5)..(6)
<223> OTHER INFORMATION: Xaa = any amino acid
<220> FEATURE:
<221> NAME/KEY: VARIANT
<222> LOCATION: (7)..(7)
<223> OTHER INFORMATION: Xaa = any amino acid, may be present or absent

<400> SEQUENCE: 16

Thr Xaa Xaa Gln Xaa Xaa Xaa Asn
1               5


<210> SEQ ID NO 17
<211> LENGTH: 14
<212> TYPE: PRT
<213> ORGANISM: Artificial Sequence
<220> FEATURE:
<223> OTHER INFORMATION: Symthetic polypeptide of cellobiohydrolase
      glutamine-containing Q117 motif
<220> FEATURE:
<221> NAME/KEY: VARIANT
<222> LOCATION: (4)..(5)
<223> OTHER INFORMATION: Xaa = any amino acid
<220> FEATURE:
<221> NAME/KEY: VARIANT
<222> LOCATION: (7)..(8)
<223> OTHER INFORMATION: Xaa = any amino acid
<220> FEATURE:
<221> NAME/KEY: VARIANT
```

<222> LOCATION: (9)..(9)
<223> OTHER INFORMATION: Xaa = any amino acid may be present or absent
<220> FEATURE:
<221> NAME/KEY: VARIANT
<222> LOCATION: (11)..(11)
<223> OTHER INFORMATION: Xaa = Ile or Val

<400> SEQUENCE: 17

Phe Val Thr Xaa Xaa Gln Xaa Xaa Xaa Asn Xaa Gly Ser Arg
1 5 10

<210> SEQ ID NO 18
<211> LENGTH: 12
<212> TYPE: PRT
<213> ORGANISM: Artificial Sequence
<220> FEATURE:
<223> OTHER INFORMATION: Synmthetic polypeptide of cellobiohydrolase glutamine-containing Q117 motif
<220> FEATURE:
<221> NAME/KEY: VARIANT
<222> LOCATION: (2)..(2)
<223> OTHER INFORMATION: Xaa = Val or Ile
<220> FEATURE:
<221> NAME/KEY: VARIANT
<222> LOCATION: (4)..(4)
<223> OTHER INFORMATION: Xaa = Lys, Asn, Gln, Glu, Ser or Thr
<220> FEATURE:
<221> NAME/KEY: VARIANT
<222> LOCATION: (5)..(5)
<223> OTHER INFORMATION: Xaa = Gly, Ser or His
<220> FEATURE:
<221> NAME/KEY: VARIANT
<222> LOCATION: (7)..(7)
<223> OTHER INFORMATION: Xaa = Tyr or absent
<220> FEATURE:
<221> NAME/KEY: VARIANT
<222> LOCATION: (8)..(8)
<223> OTHER INFORMATION: Xaa = Gln, Ser or Gly
<220> FEATURE:
<221> NAME/KEY: VARIANT
<222> LOCATION: (9)..(9)
<223> OTHER INFORMATION: Xaa = Thr or Lys
<220> FEATURE:
<221> NAME/KEY: VARIANT
<222> LOCATION: (11)..(11)
<223> OTHER INFORMATION: Xaa = Ile or Val

<400> SEQUENCE: 18

Phe Xaa Thr Xaa Xaa Gln Xaa Xaa Xaa Asn Xaa Gly
1 5 10

<210> SEQ ID NO 19
<211> LENGTH: 15
<212> TYPE: PRT
<213> ORGANISM: Artificial Sequence
<220> FEATURE:
<223> OTHER INFORMATION: Synthetic polypeptide of cellobiohydrolase glutamine-containing Q117 motif
<220> FEATURE:
<221> NAME/KEY: VARIANT
<222> LOCATION: (1)..(1)
<223> OTHER INFORMATION: Xaa = Lys, Asn, Gln or Thr
<220> FEATURE:
<221> NAME/KEY: VARIANT
<222> LOCATION: (3)..(3)
<223> OTHER INFORMATION: Xaa = Ile or Val
<220> FEATURE:
<221> NAME/KEY: VARIANT
<222> LOCATION: (5)..(5)
<223> OTHER INFORMATION: Xaa = Lys, Asn, Gln, Glu, Ser or Thr
<220> FEATURE:
<221> NAME/KEY: VARIANT
<222> LOCATION: (6)..(6)
<223> OTHER INFORMATION: Xaa = Gly, Ser or His
<220> FEATURE:

<221> NAME/KEY: VARIANT
<222> LOCATION: (8)..(8)
<223> OTHER INFORMATION: Xaa = Tyr or absent
<220> FEATURE:
<221> NAME/KEY: VARIANT
<222> LOCATION: (9)..(9)
<223> OTHER INFORMATION: Xaa = Gln, Ser or Gly
<220> FEATURE:
<221> NAME/KEY: VARIANT
<222> LOCATION: (10)..(10)
<223> OTHER INFORMATION: Xaa = Thr or Lys
<220> FEATURE:
<221> NAME/KEY: VARIANT
<222> LOCATION: (12)..(12)
<223> OTHER INFORMATION: Xaa = Ile or Val

<400> SEQUENCE: 19

Xaa Phe Xaa Thr Xaa Xaa Gln Xaa Xaa Xaa Asn Xaa Gly Ser Arg
1               5                   10                  15

<210> SEQ ID NO 20
<211> LENGTH: 18
<212> TYPE: PRT
<213> ORGANISM: Artificial Sequence
<220> FEATURE:
<223> OTHER INFORMATION: Synthetic polypeptide of cellobiohydrolase
      glutamine-containing Q117 motif
<220> FEATURE:
<221> NAME/KEY: VARIANT
<222> LOCATION: (2)..(2)
<223> OTHER INFORMATION: Xaa = any amino acid
<220> FEATURE:
<221> NAME/KEY: VARIANT
<222> LOCATION: (4)..(4)
<223> OTHER INFORMATION: Xaa = Lys, Asn, Gln or Thr
<220> FEATURE:
<221> NAME/KEY: VARIANT
<222> LOCATION: (6)..(6)
<223> OTHER INFORMATION: Xaa = Ile or Val
<220> FEATURE:
<221> NAME/KEY: VARIANT
<222> LOCATION: (8)..(8)
<223> OTHER INFORMATION: Xaa = Lys, Asn, Gln, Glu, Ser or Thr
<220> FEATURE:
<221> NAME/KEY: VARIANT
<222> LOCATION: (9)..(9)
<223> OTHER INFORMATION: Xaa = Gly, Ser or His
<220> FEATURE:
<221> NAME/KEY: VARIANT
<222> LOCATION: (11)..(11)
<223> OTHER INFORMATION: Xaa = Tyr or absent
<220> FEATURE:
<221> NAME/KEY: VARIANT
<222> LOCATION: (12)..(12)
<223> OTHER INFORMATION: Xaa = Gln, Ser or Gly
<220> FEATURE:
<221> NAME/KEY: VARIANT
<222> LOCATION: (13)..(13)
<223> OTHER INFORMATION: Xaa = Thr or Lys
<220> FEATURE:
<221> NAME/KEY: VARIANT
<222> LOCATION: (15)..(15)
<223> OTHER INFORMATION: Xaa = Ile or Val

<400> SEQUENCE: 20

Leu Xaa Leu Xaa Phe Xaa Thr Xaa Xaa Gln Xaa Xaa Xaa Asn Xaa Gly
1               5                   10                  15

Ser Arg

<210> SEQ ID NO 21
<211> LENGTH: 500
<212> TYPE: PRT
<213> ORGANISM: Artificial Sequence
<220> FEATURE:

```
<223> OTHER INFORMATION: Synthetic polypeptide of cellobiohydrolase
      CBH1a truncated variant

<400> SEQUENCE: 21

Gln Asn Ala Cys Thr Leu Thr Ala Glu Asn His Pro Ser Leu Thr Trp
1               5                   10                  15

Ser Lys Cys Thr Ser Gly Gly Ser Cys Thr Ser Val Gln Gly Ser Ile
            20                  25                  30

Thr Ile Asp Ala Asn Trp Arg Trp Thr His Arg Thr Asp Ser Ala Thr
        35                  40                  45

Asn Cys Tyr Glu Gly Asn Lys Trp Asp Thr Ser Tyr Cys Ser Asp Gly
    50                  55                  60

Pro Ser Cys Ala Ser Lys Cys Cys Ile Asp Gly Ala Asp Tyr Ser Ser
65                  70                  75                  80

Thr Tyr Gly Ile Thr Thr Ser Gly Asn Ser Leu Asn Leu Lys Phe Val
                85                  90                  95

Thr Lys Gly Gln Tyr Ser Thr Asn Ile Gly Ser Arg Thr Tyr Leu Met
            100                 105                 110

Glu Ser Asp Thr Lys Tyr Gln Met Phe Gln Leu Leu Gly Asn Glu Phe
        115                 120                 125

Thr Phe Asp Val Asp Val Ser Asn Leu Gly Cys Gly Leu Asn Gly Ala
    130                 135                 140

Leu Tyr Phe Val Ser Met Asp Ala Asp Gly Gly Met Ser Lys Tyr Ser
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Glu Ala Asn Val Glu Asn
            180                 185                 190

Trp Gln Ser Ser Thr Asn Asp Ala Asn Ala Gly Thr Gly Lys Tyr Gly
        195                 200                 205

Ser Cys Cys Ser Glu Met Asp Val Trp Glu Ala Asn Asn Met Ala Ala
    210                 215                 220

Ala Phe Thr Pro His Pro Cys Thr Val Ile Gly Gln Ser Arg Cys Glu
225                 230                 235                 240

Gly Asp Ser Cys Gly Gly Thr Tyr Ser Thr Asp Arg Tyr Ala Gly Ile
                245                 250                 255

Cys Asp Pro Asp Gly Cys Asp Phe Asn Ser Tyr Arg Gln Gly Asn Lys
            260                 265                 270

Thr Phe Tyr Gly Lys Gly Met Thr Val Asp Thr Thr Lys Lys Ile Thr
        275                 280                 285

Val Val Thr Gln Phe Leu Lys Asn Ser Ala Gly Glu Leu Ser Glu Ile
    290                 295                 300

Lys Arg Phe Tyr Val Gln Asn Gly Lys Val Ile Pro Asn Ser Glu Ser
305                 310                 315                 320

Thr Ile Pro Gly Val Glu Gly Asn Ser Ile Thr Gln Asp Trp Cys Asp
                325                 330                 335

Arg Gln Lys Ala Ala Phe Gly Asp Val Thr Asp Phe Gln Asp Lys Gly
            340                 345                 350

Gly Met Val Gln Met Gly Lys Ala Leu Ala Gly Pro Met Val Leu Val
        355                 360                 365

Met Ser Ile Trp Asp Asp His Ala Val Asn Met Leu Trp Leu Asp Ser
    370                 375                 380

Thr Trp Pro Ile Asp Gly Ala Gly Lys Pro Gly Ala Glu Arg Gly Ala
385                 390                 395                 400
```

Cys Pro Thr Thr Ser Gly Val Pro Ala Glu Val Glu Ala Glu Ala Pro
405 410 415

Asn Ser Asn Val Ile Phe Ser Asn Ile Arg Phe Gly Pro Ile Gly Ser
420 425 430

Thr Val Ser Gly Leu Pro Asp Gly Gly Ser Gly Asn Pro Asn Pro Pro
435 440 445

Val Ser Ser Ser Thr Pro Val Pro Ser Ser Ser Thr Thr Ser Ser Gly
450 455 460

Ser Ser Gly Pro Thr Gly Gly Thr Gly Val Ala Lys His Tyr Glu Gln
465 470 475 480

Cys Gly Gly Ile Gly Phe Thr Gly Pro Thr Gln Cys Glu Ala Arg Thr
485 490 495

Leu Ala Pro Ser
500

<210> SEQ ID NO 22
<211> LENGTH: 7
<212> TYPE: PRT
<213> ORGANISM: Artificial Sequence
<220> FEATURE:
<223> OTHER INFORMATION: Synthetic polypeptide of cellobiohydrolase CBH1a truncated variant C-terminus 7-mer

<400> SEQUENCE: 22

Ala Arg Thr Leu Ala Pro Ser
1 5

<210> SEQ ID NO 23
<211> LENGTH: 2487
<212> TYPE: DNA
<213> ORGANISM: Myceliophthora thermophila

<400> SEQUENCE: 23
atgaggacct cctctcgttt aatcggtgcc cttgcggcgg cactcttgcc gtctgccctt 60
gcgcagaaca acgcgccggt aacccttcacc gacccggact cgggcattac cttcaacacg 120
tggggtctcg ccgaggattc tccccagact aagggcggtt tcacttttgg tgttgctctg 180
ccctctgatg ccctcacgac agacgccaag gagttcatcg gttacttgaa atgcgcgagg 240
aacgatgaga gcggttggtg cggtgtctcc ctgggcggcc ccatgaccaa ctcgctcctc 300
atcgcggcct ggccccacga ggacaccgtc tacacctctc tccgcttcgc caccggctat 360
gccatgccgg atgtctacca gggggacgcc gagatcaccc aggtctcctc ctctgtcaac 420
tcgacgcact tcagcctcat cttcaggtgc gagaactgcc tgcaatggag tcaaagcggc 480
gccaccggcg gtgcctccac ctcgaacggc gtgttggtcc tcggctgggt ccaggcattc 540
gccgaccccg gcaacccgac ctgccccgac cagatcaccc tcgagcagca cgacaacggc 600
atgggtatct ggggtgccca gctcaactcc gacgccgcca gcccgtccta caccgagtgg 660
gccgcccagg ccaccaagac cgtcacgggt gactgcggcg gtcccaccga gacctctgtc 720
gtcggtgtcc ccgttccgac gggcgtctcg ttcgattaca tcgtcgtggg cggcggtgcc 780
ggtggcatcc ccgccgccga caagctcagc gaggccggca agagtgtgct gctcatcgag 840
aagggctttg cctcgaccgc caacaccgga ggcactctcg gccccgagtg gctcgagggc 900
cacgacctta cccgctttga cgtgccgggt ctgtgcaacc agatctgggt tgactccaag 960
gggatcgctt gcgaggatac cgaccagatg gctggctgtg tcctcggcgg cggtaccgcc 1020
gtgaatgccg gcctgtggtt caagccctac tcgctcgact gggactacct cttccctagt 1080

```
ggttggaagt acaaagacgt ccagccggcc atcaaccgcg ccctctcgcg catcccgggc   1140

accgatgctc cctcgaccga cggcaagcgc tactaccaac agggcttcga cgtcctctcc   1200

aagggcctgg ccggcggcgg ctggacctcg gtcacggcca ataacgcgcc agacaagaag   1260

aaccgcacct tctcccatgc ccccttcatg ttcgccggcg gcgagcgcaa cggcccgctg   1320

ggcacctact tccagaccgc caagaagcgc agcaacttca agctctggct caacacgtcg   1380

gtcaagcgcg tcatccgcca gggcggccac atcaccggcg tcgaggtcga gccgttccgc   1440

gacggcggtt accaaggcat cgtccccgtc accaaggtta cgggccgcgt catcctctct   1500

gccggtacct ttggcagtgc aaagatcctg ctgaggagcg gtatcggtcc gaacgatcag   1560

ctgcaggttg tcgcggcctc ggagaaggat ggccctacca tgatcagcaa ctcgtcctgg   1620

atcaacctgc ctgtcggcta caacctggat gaccacctca acaccgacac tgtcatctcc   1680

caccccgacg tcgtgttcta cgacttctac gaggcgtggg acaatcccat ccagtctgac   1740

aaggacagct acctcaactc gcgcacgggc atcctcgccc aagccgctcc caacattggg   1800

cctatgttct gggaagagat caagggtgcg gacggcattg ttcgccagct ccagtggact   1860

gcccgtgtcg agggcagcct gggtgccccc aacggcaaga ccatgaccat gtcgcagtac   1920

ctcggtcgtg gtgccacctc gcgcggccgc atgaccatca ccccgtccct gacaactgtc   1980

gtctcggacg tgccctacct caaggacccc aacgacaagg aggccgtcat ccagggcatc   2040

atcaacctgc agaacgccct caagaacgtc gccaacctga cctggctctt ccccaactcg   2100

accatcacgc cgcgccaata cgttgacagc atggtcgtct ccccgagcaa ccggcgctcc   2160

aaccactgga tgggcaccaa caagatcggc accgacgacg ggcgcaaggg cggctccgcc   2220

gtcgtcgacc tcaacaccaa ggtctacggc accgacaacc tcttcgtcat cgacgcctcc   2280

atcttccccg gcgtgcccac caccaacccc acctcgtaca tcgtgacggc gtcggagcac   2340

gcctcggccc gcatcctcgc cctgcccgac ctcacgcccg tccccaagta cgggcagtgc   2400

ggcggccgcg aatggagcgg cagcttcgtc tgcgccgacg gctccacgtg ccagatgcag   2460

aacgagtggt actcgcagtg cttgtga                                        2487
```

<210> SEQ ID NO 24
<211> LENGTH: 828
<212> TYPE: PRT
<213> ORGANISM: Myceliophthora thermophila

<400> SEQUENCE: 24

```
Met Arg Thr Ser Ser Arg Leu Ile Gly Ala Leu Ala Ala Ala Leu Leu
1               5                   10                  15

Pro Ser Ala Leu Ala Gln Asn Asn Ala Pro Val Thr Phe Thr Asp Pro
            20                  25                  30

Asp Ser Gly Ile Thr Phe Asn Thr Trp Gly Leu Ala Glu Asp Ser Pro
        35                  40                  45

Gln Thr Lys Gly Gly Phe Thr Phe Gly Val Ala Leu Pro Ser Asp Ala
    50                  55                  60

Leu Thr Thr Asp Ala Lys Glu Phe Ile Gly Tyr Leu Lys Cys Ala Arg
65                  70                  75                  80

Asn Asp Glu Ser Gly Trp Cys Gly Val Ser Leu Gly Gly Pro Met Thr
                85                  90                  95

Asn Ser Leu Leu Ile Ala Ala Trp Pro His Glu Asp Thr Val Tyr Thr
            100                 105                 110

Ser Leu Arg Phe Ala Thr Gly Tyr Ala Met Pro Asp Val Tyr Gln Gly
```

```
        115                 120                 125

Asp Ala Glu Ile Thr Gln Val Ser Ser Ser Val Asn Ser Thr His Phe
    130                 135                 140

Ser Leu Ile Phe Arg Cys Glu Asn Cys Leu Gln Trp Ser Gln Ser Gly
145                 150                 155                 160

Ala Thr Gly Gly Ala Ser Thr Ser Asn Gly Val Leu Val Leu Gly Trp
                165                 170                 175

Val Gln Ala Phe Ala Asp Pro Gly Asn Pro Thr Cys Pro Asp Gln Ile
            180                 185                 190

Thr Leu Glu Gln His Asp Asn Gly Met Gly Ile Trp Gly Ala Gln Leu
        195                 200                 205

Asn Ser Asp Ala Ala Ser Pro Ser Tyr Thr Glu Trp Ala Ala Gln Ala
    210                 215                 220

Thr Lys Thr Val Thr Gly Asp Cys Gly Gly Pro Thr Glu Thr Ser Val
225                 230                 235                 240

Val Gly Val Pro Val Pro Thr Gly Val Ser Phe Asp Tyr Ile Val Val
                245                 250                 255

Gly Gly Gly Ala Gly Gly Ile Pro Ala Ala Asp Lys Leu Ser Glu Ala
            260                 265                 270

Gly Lys Ser Val Leu Leu Ile Glu Lys Gly Phe Ala Ser Thr Ala Asn
        275                 280                 285

Thr Gly Gly Thr Leu Gly Pro Glu Trp Leu Glu Gly His Asp Leu Thr
    290                 295                 300

Arg Phe Asp Val Pro Gly Leu Cys Asn Gln Ile Trp Val Asp Ser Lys
305                 310                 315                 320

Gly Ile Ala Cys Glu Asp Thr Asp Gln Met Ala Gly Cys Val Leu Gly
                325                 330                 335

Gly Gly Thr Ala Val Asn Ala Gly Leu Trp Phe Lys Pro Tyr Ser Leu
            340                 345                 350

Asp Trp Asp Tyr Leu Phe Pro Ser Gly Trp Lys Tyr Lys Asp Val Gln
        355                 360                 365

Pro Ala Ile Asn Arg Ala Leu Ser Arg Ile Pro Gly Thr Asp Ala Pro
    370                 375                 380

Ser Thr Asp Gly Lys Arg Tyr Tyr Gln Gln Gly Phe Asp Val Leu Ser
385                 390                 395                 400

Lys Gly Leu Ala Gly Gly Gly Trp Thr Ser Val Thr Ala Asn Asn Ala
                405                 410                 415

Pro Asp Lys Lys Asn Arg Thr Phe Ser His Ala Pro Phe Met Phe Ala
            420                 425                 430

Gly Gly Glu Arg Asn Gly Pro Leu Gly Thr Tyr Phe Gln Thr Ala Lys
        435                 440                 445

Lys Arg Ser Asn Phe Lys Leu Trp Leu Asn Thr Ser Val Lys Arg Val
    450                 455                 460

Ile Arg Gln Gly Gly His Ile Thr Gly Val Glu Val Glu Pro Phe Arg
465                 470                 475                 480

Asp Gly Gly Tyr Gln Gly Ile Val Pro Val Thr Lys Val Thr Gly Arg
                485                 490                 495

Val Ile Leu Ser Ala Gly Thr Phe Gly Ser Ala Lys Ile Leu Leu Arg
            500                 505                 510

Ser Gly Ile Gly Pro Asn Asp Gln Leu Gln Val Val Ala Ala Ser Glu
        515                 520                 525

Lys Asp Gly Pro Thr Met Ile Ser Asn Ser Ser Trp Ile Asn Leu Pro
    530                 535                 540
```

-continued

Val Gly Tyr Asn Leu Asp Asp His Leu Asn Thr Asp Thr Val Ile Ser
545 550 555 560

His Pro Asp Val Val Phe Tyr Asp Phe Tyr Glu Ala Trp Asp Asn Pro
565 570 575

Ile Gln Ser Asp Lys Asp Ser Tyr Leu Asn Ser Arg Thr Gly Ile Leu
580 585 590

Ala Gln Ala Ala Pro Asn Ile Gly Pro Met Phe Trp Glu Glu Ile Lys
595 600 605

Gly Ala Asp Gly Ile Val Arg Gln Leu Gln Trp Thr Ala Arg Val Glu
610 615 620

Gly Ser Leu Gly Ala Pro Asn Gly Lys Thr Met Thr Met Ser Gln Tyr
625 630 635 640

Leu Gly Arg Gly Ala Thr Ser Arg Gly Arg Met Thr Ile Thr Pro Ser
645 650 655

Leu Thr Thr Val Val Ser Asp Val Pro Tyr Leu Lys Asp Pro Asn Asp
660 665 670

Lys Glu Ala Val Ile Gln Gly Ile Ile Asn Leu Gln Asn Ala Leu Lys
675 680 685

Asn Val Ala Asn Leu Thr Trp Leu Phe Pro Asn Ser Thr Ile Thr Pro
690 695 700

Arg Gln Tyr Val Asp Ser Met Val Val Ser Pro Ser Asn Arg Arg Ser
705 710 715 720

Asn His Trp Met Gly Thr Asn Lys Ile Gly Thr Asp Asp Gly Arg Lys
725 730 735

Gly Gly Ser Ala Val Val Asp Leu Asn Thr Lys Val Tyr Gly Thr Asp
740 745 750

Asn Leu Phe Val Ile Asp Ala Ser Ile Phe Pro Gly Val Pro Thr Thr
755 760 765

Asn Pro Thr Ser Tyr Ile Val Thr Ala Ser Glu His Ala Ser Ala Arg
770 775 780

Ile Leu Ala Leu Pro Asp Leu Thr Pro Val Pro Lys Tyr Gly Gln Cys
785 790 795 800

Gly Gly Arg Glu Trp Ser Gly Ser Phe Val Cys Ala Asp Gly Ser Thr
805 810 815

Cys Gln Met Gln Asn Glu Trp Tyr Ser Gln Cys Leu
820 825

<210> SEQ ID NO 25
<211> LENGTH: 2364
<212> TYPE: DNA
<213> ORGANISM: Myceliophthora thermophila

<400> SEQUENCE: 25
atgaagctac tcagccgcgt tggggcgacc gccctagcgg cgacgttgtc actgcagcaa 60
tgtgcagccc agatgaccga ggggacctac accgatgagg ctaccggtat ccaattcaag 120
acgtggaccg cctccgaggg cgcccctttc acgtttggct tgaccctccc cgcggacgcg 180
ctggaaaagg atgccaccga gtacattggt ctcctgcgtt gccaaatcac cgatcccgcc 240
tcgcccagct ggtgcggtat ctcccacggc cagtccggcc agatgacgca ggcgctgctg 300
ctggtcgcct gggccagcga ggacaccgtc tacacgtcgt tccgctacgc caccggctac 360
acgctccccg gcctctacac gggcgacgcc aagctgaccc agatctcctc ctcggtcagc 420
gaggacagct tcgaggtgct gttccgctgc gaaaactgct tctcctggga ccaggatggc 480

-continued

```
accaagggca acgtctcgac cagcaacggc aacctggtcc tcggccgcgc cgccgcgaag    540
gatggtgtga cgggccccac gtgcccggac acggccgagt tcggtttcca tgataacggt    600
ttcggacagt ggggtgccgt gcttgagggt gctacttcgg actcgtacga ggagtgggct    660
aagctggcca cgaccacgcc cgagaccacc tgcgatggca ctggccccgg cgacaaggag    720
tgcgttccgg ctcccgagga cacgtatgat tacatcgttg tcggtgccgg cgccggtggt    780
atcaccgtcg ccgacaagct cagcgaggcc ggccacaagg tccttctcat cgagaaggga    840
ccccccttcga ccggcctgtg gaacgggacc atgaagcccg agtggctcga gagcaccgac    900
cttacccgct tcgacgttcc cggcctgtgc aaccagatct gggtcgactc tgccggcatc    960
gcctgcaccg ataccgacca gatggcgggc tgcgttctcg gcggtggcac cgctgtcaac   1020
gctggtttgt ggtggaagcc ccaccccgct gactgggatg agaacttccc cgaagggtgg   1080
aagtcgagcg atctcgcgga tgcgaccgag cgtgtcttca agcgcatccc cggcacgtcg   1140
cacccgtcgc aggacggcaa gttgtaccgc caggagggct tcgaggtcat cagcaagggc   1200
ctggccaacg ccggctggaa ggaaatcagc gccaacgagg cgcccagcga gaagaaccac   1260
acctatgcac acaccgagtt catgttctcg ggcggtgagc gtggcggccc cctggcgacg   1320
taccttgcct cggctgccga gcgcagcaac ttcaacctgt ggctcaacac tgccgtccgg   1380
agggccgtcc gcagcggcag caaggtcacc ggcgtcgagc tcgagtgcct cacggacggt   1440
ggcttcagcg ggaccgtcaa cctgaatgag ggcggtggtg tcatcttctc ggccggcgct   1500
ttcggctcgg ccaagctgct ccttcgcagc ggtatcggtc ctgaggacca gctcgagatt   1560
gtggcgagct ccaaggacgg cgagaccttc actcccaagg acgagtggat caacctcccc   1620
gtcggccaca acctgatcga ccatctcaac actgacctca ttatcacgca cccggatgtc   1680
gttttctatg acttctatgc ggcctgggac gagcccatca cggaggataa ggaggcctac   1740
ctgaactcgc ggtccggcat tctcgcccag gcggcgccca atatcggccc tatgatgtgg   1800
gatcaagtca cgccgtccga cggcatcacc cgccagttcc agtggacatg ccgtgttgag   1860
ggcgacagct ccaagaccaa ctcgacccac gccatgaccc tcagccagta cctcggccgt   1920
ggcgtcgtct cgcgcggccg gatgggcatc acctccgggc tgagcacgac ggtggccgag   1980
cacccgtacc tgcacaacaa cggcgacctg gaggcggtca tccaggggat ccagaacgtg   2040
gtggacgcgc tcagccaggt ggccgacctc gagtgggtgc tcccgccgcc cgacgggacg   2100
gtggccgact acgtcaacag cctgatcgtc tcgccggcca accgccgggc caaccactgg   2160
atgggcacgg ccaagctggg caccgacgac ggccgctcgg gcggcacctc ggtcgtcgac   2220
ctcgacacca aggtgtacgg caccgacaac ctgttcgtcg tcgacgcgtc cgtcttcccc   2280
ggcatgtcga cgggcaaccc gtcggccatg atcgtcatcg tggccgagca ggcggcgcag   2340
cgcatcctgg ccctgcggtc ttaa                                          2364
```

<210> SEQ ID NO 26
<211> LENGTH: 787
<212> TYPE: PRT
<213> ORGANISM: Myceliophthora thermophila

<400> SEQUENCE: 26

```
Met Lys Leu Leu Ser Arg Val Gly Ala Thr Ala Leu Ala Ala Thr Leu
1               5                   10                  15

Ser Leu Gln Gln Cys Ala Ala Gln Met Thr Glu Gly Thr Tyr Thr Asp
            20                  25                  30

Glu Ala Thr Gly Ile Gln Phe Lys Thr Trp Thr Ala Ser Glu Gly Ala
```

```
        35                  40                  45

Pro Phe Thr Phe Gly Leu Thr Leu Pro Ala Asp Ala Leu Glu Lys Asp
    50                  55                  60

Ala Thr Glu Tyr Ile Gly Leu Leu Arg Cys Gln Ile Thr Asp Pro Ala
65                  70                  75                  80

Ser Pro Ser Trp Cys Gly Ile Ser His Gly Gln Ser Gly Gln Met Thr
                85                  90                  95

Gln Ala Leu Leu Leu Val Ala Trp Ala Ser Glu Asp Thr Val Tyr Thr
            100                 105                 110

Ser Phe Arg Tyr Ala Thr Gly Tyr Thr Leu Pro Gly Leu Tyr Thr Gly
        115                 120                 125

Asp Ala Lys Leu Thr Gln Ile Ser Ser Ser Val Ser Glu Asp Ser Phe
    130                 135                 140

Glu Val Leu Phe Arg Cys Glu Asn Cys Phe Ser Trp Asp Gln Asp Gly
145                 150                 155                 160

Thr Lys Gly Asn Val Ser Thr Ser Asn Gly Asn Leu Val Leu Gly Arg
                165                 170                 175

Ala Ala Ala Lys Asp Gly Val Thr Gly Pro Thr Cys Pro Asp Thr Ala
            180                 185                 190

Glu Phe Gly Phe His Asp Asn Gly Phe Gly Gln Trp Gly Ala Val Leu
        195                 200                 205

Glu Gly Ala Thr Ser Asp Ser Tyr Glu Glu Trp Ala Lys Leu Ala Thr
    210                 215                 220

Thr Thr Pro Glu Thr Thr Cys Asp Gly Thr Gly Pro Gly Asp Lys Glu
225                 230                 235                 240

Cys Val Pro Ala Pro Glu Asp Thr Tyr Asp Tyr Ile Val Val Gly Ala
                245                 250                 255

Gly Ala Gly Gly Ile Thr Val Ala Asp Lys Leu Ser Glu Ala Gly His
            260                 265                 270

Lys Val Leu Leu Ile Glu Lys Gly Pro Pro Ser Thr Gly Leu Trp Asn
        275                 280                 285

Gly Thr Met Lys Pro Glu Trp Leu Glu Ser Thr Asp Leu Thr Arg Phe
    290                 295                 300

Asp Val Pro Gly Leu Cys Asn Gln Ile Trp Val Asp Ser Ala Gly Ile
305                 310                 315                 320

Ala Cys Thr Asp Thr Asp Gln Met Ala Gly Cys Val Leu Gly Gly Gly
                325                 330                 335

Thr Ala Val Asn Ala Gly Leu Trp Trp Lys Pro His Pro Ala Asp Trp
            340                 345                 350

Asp Glu Asn Phe Pro Glu Gly Trp Lys Ser Ser Asp Leu Ala Asp Ala
        355                 360                 365

Thr Glu Arg Val Phe Lys Arg Ile Pro Gly Thr Ser His Pro Ser Gln
    370                 375                 380

Asp Gly Lys Leu Tyr Arg Gln Glu Gly Phe Glu Val Ile Ser Lys Gly
385                 390                 395                 400

Leu Ala Asn Ala Gly Trp Lys Glu Ile Ser Ala Asn Glu Ala Pro Ser
                405                 410                 415

Glu Lys Asn His Thr Tyr Ala His Thr Glu Phe Met Phe Ser Gly Gly
            420                 425                 430

Glu Arg Gly Gly Pro Leu Ala Thr Tyr Leu Ala Ser Ala Ala Glu Arg
        435                 440                 445

Ser Asn Phe Asn Leu Trp Leu Asn Thr Ala Val Arg Arg Ala Val Arg
    450                 455                 460
```

Ser Gly Ser Lys Val Thr Gly Val Glu Leu Glu Cys Leu Thr Asp Gly
465 470 475 480

Gly Phe Ser Gly Thr Val Asn Leu Asn Glu Gly Gly Gly Val Ile Phe
485 490 495

Ser Ala Gly Ala Phe Gly Ser Ala Lys Leu Leu Leu Arg Ser Gly Ile
500 505 510

Gly Pro Glu Asp Gln Leu Glu Ile Val Ala Ser Ser Lys Asp Gly Glu
515 520 525

Thr Phe Thr Pro Lys Asp Glu Trp Ile Asn Leu Pro Val Gly His Asn
530 535 540

Leu Ile Asp His Leu Asn Thr Asp Leu Ile Ile Thr His Pro Asp Val
545 550 555 560

Val Phe Tyr Asp Phe Tyr Ala Ala Trp Asp Glu Pro Ile Thr Glu Asp
565 570 575

Lys Glu Ala Tyr Leu Asn Ser Arg Ser Gly Ile Leu Ala Gln Ala Ala
580 585 590

Pro Asn Ile Gly Pro Met Met Trp Asp Gln Val Thr Pro Ser Asp Gly
595 600 605

Ile Thr Arg Gln Phe Gln Trp Thr Cys Arg Val Glu Gly Asp Ser Ser
610 615 620

Lys Thr Asn Ser Thr His Ala Met Thr Leu Ser Gln Tyr Leu Gly Arg
625 630 635 640

Gly Val Val Ser Arg Gly Arg Met Gly Ile Thr Ser Gly Leu Ser Thr
645 650 655

Thr Val Ala Glu His Pro Tyr Leu His Asn Asn Gly Asp Leu Glu Ala
660 665 670

Val Ile Gln Gly Ile Gln Asn Val Val Asp Ala Leu Ser Gln Val Ala
675 680 685

Asp Leu Glu Trp Val Leu Pro Pro Pro Asp Gly Thr Val Ala Asp Tyr
690 695 700

Val Asn Ser Leu Ile Val Ser Pro Ala Asn Arg Arg Ala Asn His Trp
705 710 715 720

Met Gly Thr Ala Lys Leu Gly Thr Asp Asp Gly Arg Ser Gly Gly Thr
725 730 735

Ser Val Val Asp Leu Asp Thr Lys Val Tyr Gly Thr Asp Asn Leu Phe
740 745 750

Val Val Asp Ala Ser Val Phe Pro Gly Met Ser Thr Gly Asn Pro Ser
755 760 765

Ala Met Ile Val Ile Val Ala Glu Gln Ala Ala Gln Arg Ile Leu Ala
770 775 780

Leu Arg Ser
785

<210> SEQ ID NO 27
<211> LENGTH: 1581
<212> TYPE: DNA
<213> ORGANISM: Artificial Sequence
<220> FEATURE:
<223> OTHER INFORMATION: Synthetic DNA for cellobiohydrolase CBH1a variant 5

<400> SEQUENCE: 27
atgtacgcca agttcgcgac cctcgccgcc cttgtggctg gcgccgctgc tcagaacgcc 60
tgcactctga ccgctgagaa ccacccctcg ctgacgtggt ccaagtgcac gtctggcggc 120

-continued

```
agctgcacca gcgtccaggg ttccatcacc atcgacgcca actggcggtg gactcaccgg    180

accgatagcg ccaccaactg ctacgagggc aacaagtggg atacttcgta ctgcccagat    240

ggtccttctt gcgcctccaa gtgctgcatc gacggcgctg actactcgag cacctatggc    300

atcaccacga gcggtaactc cctgaacctc aagttcgtca ccaagggcca gtactcgacc    360

aacatcggct cgcgtaccta cctgatggag agcgacacca agtaccagat gttccagctc    420

ctcggcaacg agttcacctt cgatgtcgac gtctccaacc tcccgtgcgg cctcaatggc    480

gccctctact tcgtgtccat ggatgccgat ggtggcatgt ccaagtaccc tggcaacaag    540

gcaggtgcca agtacggtac cggctactgt gattctcagt gcccccgcga cctcaagttc    600

atcaacggcg aggccaacgt agagaactgg cagccatcga ccaacgatgc caacgccggc    660

acgggcaagt acggcagctg ctgctccgag atggacgtct gggaggccaa caacatggcc    720

gccgccttca ctccccaccc ttgcaccgtg atcggccagt cgcgctgcga gggcgactcg    780

tgcggcggta cctacagcac cgaccgctat gccggcatct gcgaccccga cggatgcgac    840

ttcaactcgt accgccaggg caacaagacc ttctacggcc cgggcatgac ggtcgacacg    900

accaagaaga tcacggtcgt cacccagttc ctcaagaact cggccggcga gctctccgag    960

atcaagcggt tctacgtcca gaacggcaag gtcatcccca actccgagtc caccatcccg   1020

ggcgtcccag gcaactccat cacccaggac tggtgcgacc gccagaaggc cgccttcggc   1080

gacgtgaccg acttccagga caagggcggc atggtccaga tgggcaaggc cctcgcgggg   1140

cccatggtcc tcgtcatgtc catctgggac gaccacgccg tcaacatgct ctggctcgac   1200

tccacctggc ccatcgacgg cgccggcaag ccgggcgccg agcgcggtgc ctgccccacc   1260

acctcgggcg tccccgctga ggtcgaggcc gaggccccca actccaacgt catcttctcc   1320

aacatccgct tcggccccat cggctccacc gtctccggcc tgcccgacgg cggcagcggc   1380

aaccccaacc cgcccgtcag ctcgtccacc ccggtcccct cctcgtccac cacatcctcc   1440

ggttcctccg gcccgactgg cggcacgggt gtcgctaagc actatgagca atgcggagga   1500

atcgggttca ctggccctac ccagtgcgag agcccctaca cttgcaccaa gctgaatgac   1560

tggtactcgc agtgcctgta a                                             1581
```

<210> SEQ ID NO 28
<211> LENGTH: 526
<212> TYPE: PRT
<213> ORGANISM: Artificial Sequence
<220> FEATURE:
<223> OTHER INFORMATION: Synthetic polypeptide of cellobiohydrolase
      CBH1a variant 5

<400> SEQUENCE: 28

```
Met Tyr Ala Lys Phe Ala Thr Leu Ala Ala Leu Val Ala Gly Ala Ala
1               5                   10                  15

Ala Gln Asn Ala Cys Thr Leu Thr Ala Glu Asn His Pro Ser Leu Thr
            20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Thr His Arg Thr Asp Ser Ala
    50                  55                  60

Thr Asn Cys Tyr Glu Gly Asn Lys Trp Asp Thr Ser Tyr Cys Pro Asp
65                  70                  75                  80

Gly Pro Ser Cys Ala Ser Lys Cys Cys Ile Asp Gly Ala Asp Tyr Ser
                85                  90                  95
```

```
Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Pro Cys Gly Leu Asn Gly
145                 150                 155                 160

Ala Leu Tyr Phe Val Ser Met Asp Ala Asp Gly Gly Met Ser Lys Tyr
                165                 170                 175

Pro Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Asn Trp Gln Pro Ser Thr Asn Asp Ala Asn Ala Gly Thr Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
        275                 280                 285

Lys Thr Phe Tyr Gly Pro Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Pro Gly Asn Ser Ile Thr Gln Asp Trp Cys
            340                 345                 350

Asp Arg Gln Lys Ala Ala Phe Gly Asp Val Thr Asp Phe Gln Asp Lys
        355                 360                 365

Gly Gly Met Val Gln Met Gly Lys Ala Leu Ala Gly Pro Met Val Leu
    370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
    450                 455                 460

Pro Val Ser Ser Ser Thr Pro Val Pro Ser Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
```

515 520 525

<210> SEQ ID NO 29
<211> LENGTH: 1581
<212> TYPE: DNA
<213> ORGANISM: Artificial Sequence
<220> FEATURE:
<223> OTHER INFORMATION: Synthetic DNA for cellobiohydrolase CBH1a variant 8

<400> SEQUENCE: 29
atgtacgcca agttcgcgac cctcgccgcc cttgtggctg gcgccgctgc tcagaacgcc 60
tgcactctga ccgctgagaa ccacccctcg ctgacgtggt ccaagtgcac gtctggcggc 120
agctgcacca gcgtccaggg ttccatcacc atcgacgcca actggcggtg gactcaccgg 180
accgatagcg ccaccaactg ctacgagggc aacaagtggg atacttcgta ctgcccagat 240
ggtccttctt gcgcctccaa gtgctgcatc gacggcgctg actactcgag cacctatggc 300
atcaccacga gcggtaactc cctgaacctc aagttcgtca ccaagggcaa ctactcgacc 360
aacatcggct cgcgtaccta cctgatggag agcgacacca agtaccagat gttccagctc 420
ctcggcaacg agttcacctt cgatgtcgac gtctccaacc tcccgtgcgg cctcaatggc 480
gccctctact tcgtgtccat ggatgccgat ggtggcatgt ccaagtaccc tggcaacaag 540
gcaggtgcca agtacggtac cggctactgt gattctcagt gcccccgcga cctcaagttc 600
atcaacggcg aggccaacgt agagaactgg cagccatcga ccaacgatgc caacgccggc 660
acgggcaagt acggcagctg ctgctccgag atggacgtct gggaggccaa caacatggcc 720
gccgccttca ctccccaccc ttgcaccgtg atcggccagt cgcgctgcga gggcgactcg 780
tgcggcggta cctacagcac cgaccgctat gccggcatct gcgacccccga cggatgcgac 840 ttcaactcgt accgccaggg caacaagacc ttctacggcc cgggcatgac ggtcgacacg 900
accaagaaga tcacggtcgt cacccagttc ctcaagaact cggccggcga gctctccgag 960
atcaagcggt tctacgtcca gaacggcaag gtcatcccca actccgagtc caccatcccg 1020
ggcgtcccag gcaactccat cacccaggac tggtgcgacc gccagaaggc cgccttcggc 1080
gacgtgaccg acttccagga caagggcggc atggtccaga tgggcaaggc cctcgcgggg 1140
ggcatggtcc tcgtcatgtc catctgggac gaccacgccg tcaacatgct ctggctcgac 1200
tccacctggc ccatcgacgg cgccggcaag ccgggcgccg agcgcggtcc gtgccccacc 1260
acctcgggcg tccccgctga ggtcgaggcc gaggccccca actccaacgt catcttctcc 1320
aacatccgct tcggccccat cggctccacc gtctccggcc tgcccgacgg cggcagcggc 1380
aaccccaacc cgcccgtcag ctcgtccacc ccggtcccct cctcgtccac cacatcctcc 1440
ggttcctccg gcccgactgg cggcacgggt gtcgctaagc actatgagca atgcggagga 1500
atcgggttca ctggccctac ccagtgcgag agcccctaca cttgcaccaa gctgaatgac 1560
tggtactcgc agtgcctgta a 1581

<210> SEQ ID NO 30
<211> LENGTH: 526
<212> TYPE: PRT
<213> ORGANISM: Artificial Sequence
<220> FEATURE:
<223> OTHER INFORMATION: Synthetic polypeptide of cellobiohydrolase CBH1a variant 8

<400> SEQUENCE: 30

Met Tyr Ala Lys Phe Ala Thr Leu Ala Ala Leu Val Ala Gly Ala Ala

-continued

```
1               5                   10                  15

Ala Gln Asn Ala Cys Thr Leu Thr Ala Glu Asn His Pro Ser Leu Thr
            20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Thr His Arg Thr Asp Ser Ala
    50                  55                  60

Thr Asn Cys Tyr Glu Gly Asn Lys Trp Asp Thr Ser Tyr Cys Pro Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Asn Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Pro Cys Gly Leu Asn Gly
145                 150                 155                 160

Ala Leu Tyr Phe Val Ser Met Asp Ala Asp Gly Gly Met Ser Lys Tyr
                165                 170                 175

Pro Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Asn Trp Gln Pro Ser Thr Asn Asp Ala Asn Ala Gly Thr Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
        275                 280                 285

Lys Thr Phe Tyr Gly Pro Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Pro Gly Asn Ser Ile Thr Gln Asp Trp Cys
            340                 345                 350

Asp Arg Gln Lys Ala Ala Phe Gly Asp Val Thr Asp Phe Gln Asp Lys
        355                 360                 365

Gly Gly Met Val Gln Met Gly Lys Ala Leu Ala Gly Gly Met Val Leu
    370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Pro Cys Pro Thr Thr Ser Gly Val Pro Ala Glu Val Glu Ala Glu Ala
            420                 425                 430
```

-continued

```
Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
    450                 455                 460

Pro Val Ser Ser Ser Thr Pro Val Pro Ser Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525


<210> SEQ ID NO 31
<211> LENGTH: 1581
<212> TYPE: DNA
<213> ORGANISM: Artificial Sequence
<220> FEATURE:
<223> OTHER INFORMATION: Synthetic DNA for cellobiohydrolase CBH1a
      variant 15

<400> SEQUENCE: 31

atgtacgcca agttcgcgac cctcgccgcc cttgtggctg gcgccgctgc tcagaacgcc      60

tgcactctga ccgctgagaa ccaccccccg ctgacgtggt ccaagtgcac gtctggcggc     120

agctgcacca gcgtccaggg ttccatcacc atcgacgcca actggcggtg gatccaccgg     180

accgatagcg ccaccaactg ctacgagggc aacaagtggg atacttcgta ctgcccagat     240

ggtatgtctt gcgcctccaa gtgctgcatc gacggcgctg actactcgag cacctatggc     300

atcaccacga gcggtaactc cctgaacctc aagttcgtca ccaagggcaa ctactcgacc     360

aacatcggct cgcgtaccta cctgatggag agcgacacca agtaccagat gttccagctc     420

ctcggcaacg agttcacctt cgatgtcgac gtctccaacc tcccgtgcgg cctcaatggc     480

gccctctact tcgtgtccat ggatgccgat ggtggcatgt ccaagtacca gggcaacaag     540

gcaggtgcca agtacggtac cggctactgt gattctcagt gcccccgcga cctcaagttc     600

atcaacggcg aggccaacgt agagaactgg cagccatcga ccaacgatgc caacgccggc     660

acgggcaagt acggcagctg ctgctccgag atggacgtct gggaggccaa caacatggcc     720

gccgccttca ctccccaccc ttgcaccgtg atcggccagt cgcgctgcga gggcgactcg     780

tgcggcggta cctacagcac cgaccgctat gccggcatct gcgaccccga cggatgcgac     840

ttcaactcgt accgccaggg caacaagacc ttctacggcc cgggcatgac ggtcgacacg     900

accaagaaga tcacggtcgt cacccagttc ctcaagaact cggccggcga gctctccgag     960

atcaagcggt tctacgtcca gaacggcaag gtcatcccca actccgagtc caccatcccg    1020

ggcgtcccag gcaactccat cacccaggac tggtgcgacc gccagaaggc cgccttcggc    1080

gacgtgaccg acttccagga caagggcggc atggtccaga tgggcaaggc cctcgcgggg    1140

ggcatggtcc tcgtcatgtc catctgggac gaccacgccg tcaacatgct ctggctcgac    1200

tccacctggc ccatcgacgg cgccggcaag ccgggcgccg agcgcggtcc gtgccccacc    1260

acctcgggcg tccccgctga ggtcgaggcc gaggccccca actccaacgt catcttctcc    1320

aacatccgct tcggccccat cggctccacc gtctccggcc tgcccgacgg cggcagcggc    1380

aaccccaacc cgcccgtcag ctcgtccacc ccggtcccct cctcgtccac cacatcctcc    1440

ggttcctccg gcccgactgg cggcacgggt gtcgctaagc actatgagca atgcggagga    1500
```

```
atcgggttca ctggccctac ccagtgcgag agcccctaca cttgcaccaa gctgaatgac   1560

tggtactcgc agtgcctgta a                                              1581


<210> SEQ ID NO 32
<211> LENGTH: 526
<212> TYPE: PRT
<213> ORGANISM: Artificial Sequence
<220> FEATURE:
<223> OTHER INFORMATION: Synthetic polypeptide of cellobiohydrolase
      CBH1a variant 15

<400> SEQUENCE: 32

Met Tyr Ala Lys Phe Ala Thr Leu Ala Ala Leu Val Ala Gly Ala Ala
1               5                   10                  15

Ala Gln Asn Ala Cys Thr Leu Thr Ala Glu Asn His Pro Pro Leu Thr
            20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Ile His Arg Thr Asp Ser Ala
    50                  55                  60

Thr Asn Cys Tyr Glu Gly Asn Lys Trp Asp Thr Ser Tyr Cys Pro Asp
65                  70                  75                  80

Gly Met Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Asn Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Pro Cys Gly Leu Asn Gly
145                 150                 155                 160

Ala Leu Tyr Phe Val Ser Met Asp Ala Asp Gly Gly Met Ser Lys Tyr
                165                 170                 175

Gln Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Asn Trp Gln Pro Ser Thr Asn Asp Ala Asn Ala Gly Thr Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
        275                 280                 285

Lys Thr Phe Tyr Gly Pro Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335
```

-continued

```
Ser Thr Ile Pro Gly Val Pro Gly Asn Ser Ile Thr Gln Asp Trp Cys
            340                 345                 350

Asp Arg Gln Lys Ala Ala Phe Gly Asp Val Thr Asp Phe Gln Asp Lys
        355                 360                 365

Gly Gly Met Val Gln Met Gly Lys Ala Leu Ala Gly Gly Met Val Leu
    370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Pro Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
    450                 455                 460

Pro Val Ser Ser Ser Thr Pro Val Pro Ser Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525


<210> SEQ ID NO 33
<211> LENGTH: 1581
<212> TYPE: DNA
<213> ORGANISM: Artificial Sequence
<220> FEATURE:
<223> OTHER INFORMATION: Synthetic DNA for cellobiohydrolase CBH1a
      variant 17

<400> SEQUENCE: 33

atgtacgcca agttcgcgac cctcgccgcc cttgtggctg gcgccgctgc tcagaacgcc      60

tgcactctga ccgctgagaa ccacccccg ctgacgtggt ccaagtgcac gtctggcggc      120

agctgcacca gcgtccaggg ttccatcacc atcgacgcca actggcggtg gatccaccgg     180

accgatagcg ccaccaactg ctacgagggc aacaagtggg atacttcgta ctgcccagat     240

ggtatgtctt gcgcctccaa gtgctgcgtc gacggcgctg actactcgag cacctatggc     300

atcaccacga gcggtaactc cctgaacctc aagttcgtca ccaagggcaa ctactcgacc     360

aacatcggct cgcgtaccta cctgatggag agcgacacca agtaccagat gttccagctc     420

ctcggcaacg agttcacctt cgatgtcgac gtctccaacc tcccgtgcgg cctcaatggc     480

gccctctact tcgtgtccat ggatgccgat ggtggcatgt ccaagtaccc gggcaacaag     540

gcaggtgcca agtacggtac cggctactgt gattctcagt gcccccgcga cctcaagttc     600

atcaacggcg aggccaacgt agagggctgg cagccatcga ccaacgatgc caacgccggc     660

tggggcaagt acggcagctg ctgctccgag atggacgtct gggaggccaa caacatggcc     720

gccgccttca ctccccaccc ttgcaccgtg atcggccagt cgcgctgcga gggcgactcg     780

tgcggcggta cctacagcac cgaccgctat gccggcatct gcgaccccga cggatgcgac     840

ttcaactcgt accgcatggg caacaagacc ttctacggcc cgggcatgac ggtcgacacg     900

accaagaaga tcacggtcgt cacccagttc ctcaagaact cggccggcga gctctccgag     960
```

-continued

```
atcaagcggt tctacgtcca gaacggcaag gtcatcccca actccgagtc caccatcccg   1020

ggcgtcccag gcaactccat cacccaggac tggtgcgacc gccagaaggc cgccttcggc   1080

gacgtgaccg acttccagga caagggcggc atggtccaga tgggcaaggc cctcgcgggg   1140

ggcatggtcc tcgtcatgtc catctgggac gaccacgccg tcaacatgct ctggctcgac   1200

tccacctggc ccatcgacgg cgccggcaag ccgggcgccg agcgcggtcc gtgccccacc   1260

acctcgggcg tccccgctga ggtcgaggcc gaggccccca actccaacgt catcttctcc   1320

aacatccgct tcggccccat cggctccacc gtctccggcc tgcccgacgg cggcagcggc   1380

aaccccaacc cgcccgtcag ctcgtccacc ccggtcccct cctcgtccac cacatcctcc   1440

ggttcctccg gcccgactgg cggcacgggt gtcgctaagc actatgagca atgcggagga   1500

atcgggttca ctggccctac ccagtgcgag agcccctaca cttgcaccaa gctgaatgac   1560

tggtactcgc agtgcctgta a                                             1581


<210> SEQ ID NO 34
<211> LENGTH: 526
<212> TYPE: PRT
<213> ORGANISM: Artificial Sequence
<220> FEATURE:
<223> OTHER INFORMATION: Synthetic polypeptides of cellobiohydrolase
      CBH1a variant 17

<400> SEQUENCE: 34

Met Tyr Ala Lys Phe Ala Thr Leu Ala Ala Leu Val Ala Gly Ala Ala
1               5                   10                  15

Ala Gln Asn Ala Cys Thr Leu Thr Ala Glu Asn His Pro Pro Leu Thr
            20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Ile His Arg Thr Asp Ser Ala
    50                  55                  60

Thr Asn Cys Tyr Glu Gly Asn Lys Trp Asp Thr Ser Tyr Cys Pro Asp
65                  70                  75                  80

Gly Met Ser Cys Ala Ser Lys Cys Cys Val Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Asn Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Pro Cys Gly Leu Asn Gly
145                 150                 155                 160

Ala Leu Tyr Phe Val Ser Met Asp Ala Asp Gly Gly Met Ser Lys Tyr
                165                 170                 175

Pro Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Gly Trp Gln Pro Ser Thr Asn Asp Ala Asn Ala Gly Trp Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
```

-continued

```
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Met Gly Asn
        275                 280                 285

Lys Thr Phe Tyr Gly Pro Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Pro Gly Asn Ser Ile Thr Gln Asp Trp Cys
            340                 345                 350

Asp Arg Gln Lys Ala Ala Phe Gly Asp Val Thr Asp Phe Gln Asp Lys
        355                 360                 365

Gly Gly Met Val Gln Met Gly Lys Ala Leu Ala Gly Gly Met Val Leu
    370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Pro Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
    450                 455                 460

Pro Val Ser Ser Ser Thr Pro Val Pro Ser Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525


<210> SEQ ID NO 35
<211> LENGTH: 1581
<212> TYPE: DNA
<213> ORGANISM: Artificial Sequence
<220> FEATURE:
<223> OTHER INFORMATION: Synthetic DNA for cellobiohydrolase CBH1a
      variant 20

<400> SEQUENCE: 35

atgtacgcca agttcgcgac cctcgccgcc cttgtggctg gcgccgctgc tcagaacgcc      60

tgcactctga ccgctgagaa ccaccccccg ctgacgtggt ccaagtgcac gtctggcggc     120

agctgcacca gcgtccaggg ttccatcacc atcgacgcca actggcggtg gatccaccgg     180

accgatagcg ccaccaactg ctacgagggc aacaagtggg atacttcgta ctgcccagat     240

ggtatgtctt gcgcctccaa gtgctgcgtc gacggcgctg actactcgag cacctatggc     300

atcaccacga gcggtaactc cctgaacctc aagttcgtca ccaagggcaa ctactcgacc     360

aacatcggct cgcgtaccta cctgatggag agcgacacca agtaccagat gttccagctc     420

ctcggcaacg agttcacctt cgatgtcgac gtctccaacc tcccgtgcgg cctcaatggc     480
```

```
gccctctact tcgtgtccat ggatgccgat ggtggcatgt ccaagtaccc gggcaacaag    540

gcaggtgcca agtacggtac cggctactgt gattctcagt gcccccgcga cctcaagttc    600

atcaacggcg aggccaacgt agagggctgg cagccatcga ccaacgatgc caacgccggc    660

tggggcaagt acggcagctg ctgctccgag atggacgtct gggaggccaa caacatggcc    720

gccgccttca ctccccaccc ttgcaccgtg atcggccagt cgcgctgcga gggcgactcg    780

tgcggcggta cctacagcac cgaccgctat gccggcatct gcgacccgga cggatgcgac    840

ttcaactcgt accgcatggg caacaagacc ttctacggcc cgggcatgac ggtcgacacg    900

accaagaaga tcacggtcgt cacccagttc ctcaagaact cggccggcga gctctccgag    960

atcaagcggt tctacgtcca gaacggcaag gtcatcccca actccgagtc caccatcccg   1020

ggcgtcccag gcaactccat cacccaggac tggtgcgacc gccagaaggc cgccttcggc   1080

gacgtgaccg acttccagga caagggcggc atggtccaga tgggcaaggc cctcgcgggg   1140

ggcatggtcc tcgtcatgtc catctgggac gaccacgccg tcaacatgct ctggctcgac   1200

gatacctggc ccatcgacgg cgccggcaag ccgggcgccg agcgcggtcc gtgccccacc   1260

acctcgggcg tccccgctga ggtcgaggcc gaggccccca actccaacgt catcttctcc   1320

aacatccgct tcggccccat cggctccacc gtctccggcc tgcccgacgg cggcagcggc   1380

aaccccaacc cgcccgtcag ctcgtccacc ccggtcccct cctcgtccac cacatcctcc   1440

ggttcctccg gcccgactgg cggcacgggt gtcgctaagc actatgagca atgcggagga   1500

atcgggttca ctggccctac ccagtgcgag agcccctaca cttgcaccaa gctgaatgac   1560

tggtactcgc agtgcctgta a                                             1581
```

```
<210> SEQ ID NO 36
<211> LENGTH: 526
<212> TYPE: PRT
<213> ORGANISM: Artificial Sequence
<220> FEATURE:
<223> OTHER INFORMATION: Synthetic polypeptide of cellobiohydrolase
      CBH1a variant 20

<400> SEQUENCE: 36

Met Tyr Ala Lys Phe Ala Thr Leu Ala Ala Leu Val Ala Gly Ala Ala
1               5                   10                  15

Ala Gln Asn Ala Cys Thr Leu Thr Ala Glu Asn His Pro Pro Leu Thr
            20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Ile His Arg Thr Asp Ser Ala
    50                  55                  60

Thr Asn Cys Tyr Glu Gly Asn Lys Trp Asp Thr Ser Tyr Cys Pro Asp
65                  70                  75                  80

Gly Met Ser Cys Ala Ser Lys Cys Cys Val Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Asn Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Pro Cys Gly Leu Asn Gly
145                 150                 155                 160
```

-continued

```
Ala Leu Tyr Phe Val Ser Met Asp Ala Asp Gly Gly Met Ser Lys Tyr
                165                 170                 175

Pro Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Gly Trp Gln Pro Ser Thr Asn Asp Ala Asn Ala Gly Trp Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Met Gly Asn
        275                 280                 285

Lys Thr Phe Tyr Gly Pro Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Pro Gly Asn Ser Ile Thr Gln Asp Trp Cys
            340                 345                 350

Asp Arg Gln Lys Ala Ala Phe Gly Asp Val Thr Asp Phe Gln Asp Lys
        355                 360                 365

Gly Gly Met Val Gln Met Gly Lys Ala Leu Ala Gly Gly Met Val Leu
    370                 375                 380

Val Met Ser Ile Trp Asp Asp His Ala Val Asn Met Leu Trp Leu Asp
385                 390                 395                 400

Asp Thr Trp Pro Ile Asp Gly Ala Gly Lys Pro Gly Ala Glu Arg Gly
                405                 410                 415

Pro Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
    450                 455                 460

Pro Val Ser Ser Ser Thr Pro Val Pro Ser Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525
```

<210> SEQ ID NO 37
<211> LENGTH: 1581
<212> TYPE: DNA
<213> ORGANISM: Artificial Sequence
<220> FEATURE:
<223> OTHER INFORMATION: Synthetic DNA for cellobiohydrolase CBH1a variant 32

<400> SEQUENCE: 37
atgtacgcca agttcgcgac cctcgccgcc cttgtggctg gcgccgctgc tcagaacgcc 60
tgcactctga ccgctgagaa ccacccccccg ctgacgtggt ccaagtgcac gtctggcggc 120
agctgcacca gcgtccaggg ttccatcacc atcgacgcca actggcggtg gatccaccgg 180
accgatagcg ccaccaactg ctacgagggc aacaagtggg atacttcgta ctgcccagat 240
ggtccttctt gcgcctccaa gtgctgcctc gacggcgctg actactcgag cacctatggc 300
atcaccacga gcggtaactc cctgaacctc aagttcgtca ccaagggcaa ctactcgacc 360
aacatcggct cgcgtaccta cctgatggag agcgacacca agtaccagat gttccagctc 420
ctcggcaacg agttcacctt cgatgtcgac gtctccaacc tcccgtgcgg cctcaatggc 480
gccctctact tcgtgtccat ggatgccgat ggtggcatgt ccaagtaccc gggcaacaag 540
gcaggtgcca agtacggtac cggctactgt gattctcagt gcccccgcga cctcaagttc 600
atcaacggcg aggccaacgt agagggctgg cagccatcga ccaacgatgc caacgccggc 660
tggggcaagt acggcagctg ctgctccgag atggacgtct gggaggccaa caacatggcc 720
gccgccttca ctccccaccc ttgcaccgtg atcggccagt cgcgctgcga gggcgactcg 780
tgcggcggta cctacagcac cgaccgctat gccggcatct gcgaccccga cggatgcgac 840
ttcaactcgt accgcatggg caacaagacc ttctacggcc cgggcatgac ggtcgacacg 900
accaagaaga tcacggtcgt cacccagttc ctcaagaact cggccggcga gctctccgag 960
atcaagcggt tctacgtcca gaacggcaag gtcatcccca actccgagtc caccatcccg 1020
ggcgtcccag gcaactccat cacccaggac tggtgcgacc gccagaaggc cgccttcggc 1080
gacgtgaccg acttccagga caagggcggc atggtccaga tgggcaaggc cctcgcgggg 1140
ggcatggtcc tcgtcatgtc catctgggac gaccacgccg ccaacatgct ctggctcgac 1200
gatacctggc ccatcgacgg cgccggcaag ccgggcgccg agcgcggtcc gtgccccacc 1260
acctcgggcg tccccgctga ggtcgaggcc gaggccccca actccaacgt catcttctcc 1320
aacatccgct tcggccccat cggctccacc gtctccggcc tgcccgacgg cggcagcggc 1380
aaccccaacc cgcccgtcag ctcgtccacc ccggtcccct cctcgtccac cacatcctcc 1440
ggttcctccg gcccgactgg cggcacgggt gtcgctaagc actatgagca atgcggagga 1500
atcgggttca ctggccctac ccagtgcgag agcccctaca cttgcaccaa gctgaatgac 1560
tggtactcgc agtgcctgta a 1581

<210> SEQ ID NO 38
<211> LENGTH: 526
<212> TYPE: PRT
<213> ORGANISM: Artificial Sequence
<220> FEATURE:
<223> OTHER INFORMATION: Synthetic polypeptide of cellobiohydrolase
CBH1a variant 32

<400> SEQUENCE: 38

Met Tyr Ala Lys Phe Ala Thr Leu Ala Ala Leu Val Ala Gly Ala Ala
1 5 10 15

Ala Gln Asn Ala Cys Thr Leu Thr Ala Glu Asn His Pro Pro Leu Thr
20 25 30

Trp Ser Lys Cys Thr Ser Gly Gly Ser Cys Thr Ser Val Gln Gly Ser
35 40 45

Ile Thr Ile Asp Ala Asn Trp Arg Trp Ile His Arg Thr Asp Ser Ala
50 55 60

-continued

```
Thr Asn Cys Tyr Glu Gly Asn Lys Trp Asp Thr Ser Tyr Cys Pro Asp
65                  70                  75                  80

Gly Pro Ser Cys Ala Ser Lys Cys Cys Leu Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Asn Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Pro Cys Gly Leu Asn Gly
145                 150                 155                 160

Ala Leu Tyr Phe Val Ser Met Asp Ala Asp Gly Gly Met Ser Lys Tyr
                165                 170                 175

Pro Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Gly Trp Gln Pro Ser Thr Asn Asp Ala Asn Ala Gly Trp Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Met Gly Asn
        275                 280                 285

Lys Thr Phe Tyr Gly Pro Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Pro Gly Asn Ser Ile Thr Gln Asp Trp Cys
            340                 345                 350

Asp Arg Gln Lys Ala Ala Phe Gly Asp Val Thr Asp Phe Gln Asp Lys
        355                 360                 365

Gly Gly Met Val Gln Met Gly Lys Ala Leu Ala Gly Gly Met Val Leu
    370                 375                 380

Val Met Ser Ile Trp Asp Asp His Ala Ala Asn Met Leu Trp Leu Asp
385                 390                 395                 400

Asp Thr Trp Pro Ile Asp Gly Ala Gly Lys Pro Gly Ala Glu Arg Gly
                405                 410                 415

Pro Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
    450                 455                 460

Pro Val Ser Ser Ser Thr Pro Val Pro Ser Ser Ser Thr Thr Ser Ser
465                 470                 475                 480

Gly Ser Ser Gly Pro Thr Gly Gly Thr Gly Val Ala Lys His Tyr Glu
```

```
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525


<210> SEQ ID NO 39
<211> LENGTH: 522
<212> TYPE: PRT
<213> ORGANISM: Artificial Sequence
<220> FEATURE:
<223> OTHER INFORMATION: Synthetic polypeptide of thermophilic fungus
      Humicola grisea var. thermoidea cellulase cbh-1,
      cellobiohydrolase, glycosyl hydrolase family 7 partial sequence

<400> SEQUENCE: 39

Ala Lys Phe Ala Thr Leu Ala Ala Leu Val Ala Ser Ala Ala Ala Gln
1               5                   10                  15

Gln Ala Cys Ser Leu Thr Thr Glu Arg His Pro Ser Leu Ser Trp Lys
            20                  25                  30

Lys Cys Thr Ala Gly Gly Gln Cys Gln Thr Val Gln Ala Ser Ile Thr
        35                  40                  45

Leu Asp Ser Asn Trp Arg Trp Thr His Gln Val Ser Gly Ser Thr Asn
    50                  55                  60

Cys Tyr Thr Gly Asn Lys Trp Asp Thr Ser Ile Cys Thr Asp Ala Lys
65                  70                  75                  80

Ser Cys Ala Gln Asn Cys Cys Val Asp Gly Ala Asp Tyr Thr Ser Thr
                85                  90                  95

Tyr Gly Ile Thr Thr Asn Gly Asp Ser Leu Ser Leu Lys Phe Val Thr
            100                 105                 110

Lys Gly Gln Tyr Ser Thr Asn Val Gly Ser Arg Thr Tyr Leu Met Asp
        115                 120                 125

Gly Glu Asp Lys Tyr Gln Thr Phe Glu Leu Leu Gly Asn Glu Phe Thr
    130                 135                 140

Phe Asp Val Asp Val Ser Asn Ile Gly Cys Gly Leu Asn Gly Ala Leu
145                 150                 155                 160

Tyr Phe Val Ser Met Asp Ala Asp Gly Gly Leu Ser Arg Tyr Pro Gly
                165                 170                 175

Asn Lys Ala Gly Ala Lys Tyr Gly Thr Gly Tyr Cys Asp Ala Gln Cys
            180                 185                 190

Pro Arg Asp Ile Lys Phe Ile Asn Gly Glu Ala Asn Ile Glu Gly Trp
        195                 200                 205

Thr Gly Ser Thr Asn Asp Pro Asn Ala Gly Ala Gly Arg Tyr Gly Thr
    210                 215                 220

Cys Cys Ser Glu Met Asp Ile Trp Glu Ala Asn Asn Met Ala Thr Ala
225                 230                 235                 240

Phe Thr Pro His Pro Cys Thr Ile Ile Gly Gln Ser Arg Cys Glu Gly
                245                 250                 255

Asp Ser Cys Gly Gly Thr Tyr Ser Asn Glu Arg Tyr Ala Gly Val Cys
            260                 265                 270

Asp Pro Asp Gly Cys Asp Phe Asn Ser Tyr Arg Gln Gly Asn Lys Thr
        275                 280                 285

Phe Tyr Gly Lys Gly Met Thr Val Asp Thr Thr Lys Lys Ile Thr Val
    290                 295                 300

Val Thr Gln Phe Leu Lys Asp Ala Asn Gly Asp Leu Gly Glu Ile Lys
305                 310                 315                 320
```

```
Arg Phe Tyr Val Gln Asp Gly Lys Ile Ile Pro Asn Ser Glu Ser Thr
                325                 330                 335

Ile Pro Gly Val Glu Gly Asn Ser Ile Thr Gln Asp Trp Cys Asp Arg
            340                 345                 350

Gln Lys Val Ala Phe Gly Asp Ile Asp Asp Phe Asn Arg Lys Gly Gly
        355                 360                 365

Met Lys Gln Met Gly Lys Ala Leu Ala Gly Pro Met Val Leu Val Met
    370                 375                 380

Ser Ile Trp Asp Asp His Ala Ser Asn Met Leu Trp Leu Asp Ser Thr
385                 390                 395                 400

Phe Pro Val Asp Ala Ala Gly Lys Pro Gly Ala Glu Arg Gly Ala Cys
                405                 410                 415

Pro Thr Thr Ser Gly Val Pro Ala Glu Val Glu Ala Glu Ala Pro Asn
            420                 425                 430

Ser Asn Val Val Phe Ser Asn Ile Arg Phe Gly Pro Ile Gly Ser Thr
        435                 440                 445

Val Ala Gly Leu Pro Gly Ala Gly Asn Gly Gly Asn Asn Gly Gly Asn
    450                 455                 460

Pro Pro Pro Pro Thr Thr Thr Thr Ser Ser Ala Pro Ala Thr Thr Thr
465                 470                 475                 480

Thr Ala Ser Ala Gly Pro Lys Ala Gly Arg Trp Gln Gln Cys Gly Gly
                485                 490                 495

Ile Gly Phe Thr Gly Pro Thr Gln Cys Glu Glu Pro Tyr Thr Cys Thr
            500                 505                 510

Lys Leu Asn Asp Trp Tyr Ser Gln Cys Leu
        515                 520
```

<210> SEQ ID NO 40
<211> LENGTH: 524
<212> TYPE: PRT
<213> ORGANISM: Artificial Sequence
<220> FEATURE:
<223> OTHER INFORMATION: Synthetic polypeptide of cellobiohydrolase partial consensus sequence
<220> FEATURE:
<221> NAME/KEY: VARIANT
<222> LOCATION: (12)..(12)
<223> OTHER INFORMATION: Xaa = Ser or Gly
<220> FEATURE:
<221> NAME/KEY: VARIANT
<222> LOCATION: (17)..(17)
<223> OTHER INFORMATION: Xaa = Gln or Asn
<220> FEATURE:
<221> NAME/KEY: VARIANT
<222> LOCATION: (20)..(20)
<223> OTHER INFORMATION: Xaa = Ser or Thr
<220> FEATURE:
<221> NAME/KEY: VARIANT
<222> LOCATION: (23)..(23)
<223> OTHER INFORMATION: Xaa = Thr or Ala
<220> FEATURE:
<221> NAME/KEY: VARIANT
<222> LOCATION: (25)..(25)
<223> OTHER INFORMATION: Xaa = Arg or Asn
<220> FEATURE:
<221> NAME/KEY: VARIANT
<222> LOCATION: (30)..(30)
<223> OTHER INFORMATION: Xaa = Ser or Thr
<220> FEATURE:
<221> NAME/KEY: VARIANT
<222> LOCATION: (32)..(32)
<223> OTHER INFORMATION: Xaa = Lys or Ser
<220> FEATURE:
<221> NAME/KEY: VARIANT
<222> LOCATION: (36)..(36)

<223> OTHER INFORMATION: Xaa = Ala or Ser
<220> FEATURE:
<221> NAME/KEY: VARIANT
<222> LOCATION: (39)..(39)
<223> OTHER INFORMATION: Xaa = Gln or Ser
<220> FEATURE:
<221> NAME/KEY: VARIANT
<222> LOCATION: (41)..(41)
<223> OTHER INFORMATION: Xaa = Gln or Thr
<220> FEATURE:
<221> NAME/KEY: VARIANT
<222> LOCATION: (42)..(42)
<223> OTHER INFORMATION: Xaa = Thr or Ser
<220> FEATURE:
<221> NAME/KEY: VARIANT
<222> LOCATION: (45)..(45)
<223> OTHER INFORMATION: Xaa = Ala or Gly
<220> FEATURE:
<221> NAME/KEY: VARIANT
<222> LOCATION: (49)..(49)
<223> OTHER INFORMATION: Xaa = Leu or Ile
<220> FEATURE:
<221> NAME/KEY: VARIANT
<222> LOCATION: (51)..(51)
<223> OTHER INFORMATION: Xaa = Ser or Ala
<220> FEATURE:
<221> NAME/KEY: VARIANT
<222> LOCATION: (58)..(58)
<223> OTHER INFORMATION: Xaa = Gln or Arg
<220> FEATURE:
<221> NAME/KEY: VARIANT
<222> LOCATION: (59)..(59)
<223> OTHER INFORMATION: Xaa = Val or Thr
<220> FEATURE:
<221> NAME/KEY: VARIANT
<222> LOCATION: (60)..(60)
<223> OTHER INFORMATION: Xaa = Ser or Asp
<220> FEATURE:
<221> NAME/KEY: VARIANT
<222> LOCATION: (61)..(61)
<223> OTHER INFORMATION: Xaa = Gly or Ser
<220> FEATURE:
<221> NAME/KEY: VARIANT
<222> LOCATION: (62)..(62)
<223> OTHER INFORMATION: Xaa = Ser or Ala
<220> FEATURE:
<221> NAME/KEY: VARIANT
<222> LOCATION: (67)..(67)
<223> OTHER INFORMATION: Xaa = Thr or Glu
<220> FEATURE:
<221> NAME/KEY: VARIANT
<222> LOCATION: (75)..(75)
<223> OTHER INFORMATION: Xaa = Ile or Tyr
<220> FEATURE:
<221> NAME/KEY: VARIANT
<222> LOCATION: (77)..(77)
<223> OTHER INFORMATION: Xaa = Thr or Ser
<220> FEATURE:
<221> NAME/KEY: VARIANT
<222> LOCATION: (79)..(79)
<223> OTHER INFORMATION: Xaa = Ala or Gly
<220> FEATURE:
<221> NAME/KEY: VARIANT
<222> LOCATION: (80)..(80)
<223> OTHER INFORMATION: Xaa = Lys or Pro
<220> FEATURE:
<221> NAME/KEY: VARIANT
<222> LOCATION: (84)..(84)
<223> OTHER INFORMATION: Xaa = Gln or Ser
<220> FEATURE:
<221> NAME/KEY: VARIANT
<222> LOCATION: (85)..(85)
<223> OTHER INFORMATION: Xaa = Asn or Lys
<220> FEATURE:
<221> NAME/KEY: VARIANT
<222> LOCATION: (88)..(88)
<223> OTHER INFORMATION: Xaa = Val or Ile
<220> FEATURE:
<221> NAME/KEY: VARIANT

<222> LOCATION: (94)..(94)
<223> OTHER INFORMATION: Xaa = Thr or Ser
<220> FEATURE:
<221> NAME/KEY: VARIANT
<222> LOCATION: (102)..(102)
<223> OTHER INFORMATION: Xaa = Asn or Ser
<220> FEATURE:
<221> NAME/KEY: VARIANT
<222> LOCATION: (104)..(104)
<223> OTHER INFORMATION: Xaa = Asp or Asn
<220> FEATURE:
<221> NAME/KEY: VARIANT
<222> LOCATION: (107)..(107)
<223> OTHER INFORMATION: Xaa = Ser or Asn
<220> FEATURE:
<221> NAME/KEY: VARIANT
<222> LOCATION: (120)..(120)
<223> OTHER INFORMATION: Xaa = Val or Ile
<220> FEATURE:
<221> NAME/KEY: VARIANT
<222> LOCATION: (128)..(128)
<223> OTHER INFORMATION: Xaa = Asp or Glu
<220> FEATURE:
<221> NAME/KEY: VARIANT
<222> LOCATION: (129)..(129)
<223> OTHER INFORMATION: Xaa = Gly or Ser
<220> FEATURE:
<221> NAME/KEY: VARIANT
<222> LOCATION: (130)..(130)
<223> OTHER INFORMATION: Xaa = Glu or Asp
<220> FEATURE:
<221> NAME/KEY: VARIANT
<222> LOCATION: (131)..(131)
<223> OTHER INFORMATION: Xaa = Asp or Thr
<220> FEATURE:
<221> NAME/KEY: VARIANT
<222> LOCATION: (135)..(135)
<223> OTHER INFORMATION: Xaa = Thr or Met
<220> FEATURE:
<221> NAME/KEY: VARIANT
<222> LOCATION: (137)..(137)
<223> OTHER INFORMATION: Xaa = Glu or Gln
<220> FEATURE:
<221> NAME/KEY: VARIANT
<222> LOCATION: (152)..(152)
<223> OTHER INFORMATION: Xaa = Ile or Leu
<220> FEATURE:
<221> NAME/KEY: VARIANT
<222> LOCATION: (171)..(171)
<223> OTHER INFORMATION: Xaa = Leu or Met
<220> FEATURE:
<221> NAME/KEY: VARIANT
<222> LOCATION: (173)..(173)
<223> OTHER INFORMATION: Xaa = Arg or Lys
<220> FEATURE:
<221> NAME/KEY: VARIANT
<222> LOCATION: (175)..(175)
<223> OTHER INFORMATION: Xaa = Pro or Ser
<220> FEATURE:
<221> NAME/KEY: VARIANT
<222> LOCATION: (190)..(190)
<223> OTHER INFORMATION: Xaa = Ala or Ser
<220> FEATURE:
<221> NAME/KEY: VARIANT
<222> LOCATION: (196)..(196)
<223> OTHER INFORMATION: Xaa = Ile or Leu
<220> FEATURE:
<221> NAME/KEY: VARIANT
<222> LOCATION: (205)..(205)
<223> OTHER INFORMATION: Xaa = Ile or Val
<220> FEATURE:
<221> NAME/KEY: VARIANT
<222> LOCATION: (207)..(207)
<223> OTHER INFORMATION: Xaa = Gly or Asn
<220> FEATURE:
<221> NAME/KEY: VARIANT
<222> LOCATION: (209)..(209)
<223> OTHER INFORMATION: Xaa = Thr or Gln
<220> FEATURE:

```
<221> NAME/KEY: VARIANT
<222> LOCATION: (210)..(210)
<223> OTHER INFORMATION: Xaa = Gly or Ser
<220> FEATURE:
<221> NAME/KEY: VARIANT
<222> LOCATION: (215)..(215)
<223> OTHER INFORMATION: Xaa = Pro or Ala
<220> FEATURE:
<221> NAME/KEY: VARIANT
<222> LOCATION: (219)..(219)
<223> OTHER INFORMATION: Xaa = Ala or Thr
<220> FEATURE:
<221> NAME/KEY: VARIANT
<222> LOCATION: (221)..(221)
<223> OTHER INFORMATION: Xaa = Arg or Lys
<220> FEATURE:
<221> NAME/KEY: VARIANT
<222> LOCATION: (224)..(224)
<223> OTHER INFORMATION: Xaa = Thr or Ser
<220> FEATURE:
<221> NAME/KEY: VARIANT
<222> LOCATION: (231)..(231)
<223> OTHER INFORMATION: Xaa = Ile or Val
<220> FEATURE:
<221> NAME/KEY: VARIANT
<222> LOCATION: (239)..(239)
<223> OTHER INFORMATION: Xaa = Thr or Ala
<220> FEATURE:
<221> NAME/KEY: VARIANT
<222> LOCATION: (248)..(248)
<223> OTHER INFORMATION: Xaa = Ile or Val
<220> FEATURE:
<221> NAME/KEY: VARIANT
<222> LOCATION: (265)..(265)
<223> OTHER INFORMATION: Xaa = Asn or Thr
<220> FEATURE:
<221> NAME/KEY: VARIANT
<222> LOCATION: (266)..(266)
<223> OTHER INFORMATION: Xaa = Glu or Asp
<220> FEATURE:
<221> NAME/KEY: VARIANT
<222> LOCATION: (271)..(271)
<223> OTHER INFORMATION: Xaa = Val or Ile
<220> FEATURE:
<221> NAME/KEY: VARIANT
<222> LOCATION: (311)..(311)
<223> OTHER INFORMATION: Xaa = Asp or Asn
<220> FEATURE:
<221> NAME/KEY: VARIANT
<222> LOCATION: (312)..(312)
<223> OTHER INFORMATION: Xaa = Ala or Ser
<220> FEATURE:
<221> NAME/KEY: VARIANT
<222> LOCATION: (313)..(313)
<223> OTHER INFORMATION: Xaa = Asn or Ala
<220> FEATURE:
<221> NAME/KEY: VARIANT
<222> LOCATION: (315)..(315)
<223> OTHER INFORMATION: Xaa = Asp or Glu
<220> FEATURE:
<221> NAME/KEY: VARIANT
<222> LOCATION: (317)..(317)
<223> OTHER INFORMATION: Xaa = Gly or Ser
<220> FEATURE:
<221> NAME/KEY: VARIANT
<222> LOCATION: (326)..(326)
<223> OTHER INFORMATION: Xaa = Asp or Asn
<220> FEATURE:
<221> NAME/KEY: VARIANT
<222> LOCATION: (329)..(329)
<223> OTHER INFORMATION: Xaa = Ile or Val
<220> FEATURE:
<221> NAME/KEY: VARIANT
<222> LOCATION: (355)..(355)
<223> OTHER INFORMATION: Xaa = Val or Ala
<220> FEATURE:
<221> NAME/KEY: VARIANT
<222> LOCATION: (360)..(360)
<223> OTHER INFORMATION: Xaa = Ile or Val
```

<220> FEATURE:
<221> NAME/KEY: VARIANT
<222> LOCATION: (361)..(361)
<223> OTHER INFORMATION: Xaa = Asp or Thr
<220> FEATURE:
<221> NAME/KEY: VARIANT
<222> LOCATION: (364)..(364)
<223> OTHER INFORMATION: Xaa = Asn or Gln
<220> FEATURE:
<221> NAME/KEY: VARIANT
<222> LOCATION: (365)..(365)
<223> OTHER INFORMATION: Xaa = Arg or Asp
<220> FEATURE:
<221> NAME/KEY: VARIANT
<222> LOCATION: (370)..(370)
<223> OTHER INFORMATION: Xaa = Lys or Val
<220> FEATURE:
<221> NAME/KEY: VARIANT
<222> LOCATION: (392)..(392)
<223> OTHER INFORMATION: Xaa = Ser or Val
<220> FEATURE:
<221> NAME/KEY: VARIANT
<222> LOCATION: (401)..(401)
<223> OTHER INFORMATION: Xaa = Phe or Trp
<220> FEATURE:
<221> NAME/KEY: VARIANT
<222> LOCATION: (403)..(403)
<223> OTHER INFORMATION: Xaa = Val or Ile
<220> FEATURE:
<221> NAME/KEY: VARIANT
<222> LOCATION: (405)..(405)
<223> OTHER INFORMATION: Xaa = Ala or Gly
<220> FEATURE:
<221> NAME/KEY: VARIANT
<222> LOCATION: (436)..(436)
<223> OTHER INFORMATION: Xaa = Val or Ile
<220> FEATURE:
<221> NAME/KEY: VARIANT
<222> LOCATION: (450)..(450)
<223> OTHER INFORMATION: Xaa = Ala or Ser
<220> FEATURE:
<221> NAME/KEY: VARIANT
<222> LOCATION: (454)..(454)
<223> OTHER INFORMATION: Xaa = Gly or Asp
<220> FEATURE:
<221> NAME/KEY: VARIANT
<222> LOCATION: (455)..(455)
<223> OTHER INFORMATION: Xaa = Ala or Gly
<220> FEATURE:
<221> NAME/KEY: VARIANT
<222> LOCATION: (457)..(457)
<223> OTHER INFORMATION: Xaa = Asn or Ser
<220> FEATURE:
<221> NAME/KEY: VARIANT
<222> LOCATION: (459)..(459)
<223> OTHER INFORMATION: Xaa = Gly or Asn
<220> FEATURE:
<221> NAME/KEY: VARIANT
<222> LOCATION: (460)..(460)
<223> OTHER INFORMATION: Xaa = Asn or Pro
<220> FEATURE:
<221> NAME/KEY: VARIANT
<222> LOCATION: (462)..(463)
<223> OTHER INFORMATION: Xaa = Gly or Pro
<220> FEATURE:
<221> NAME/KEY: VARIANT
<222> LOCATION: (464)..(464)
<223> OTHER INFORMATION: Xaa = Asn or Val
<220> FEATURE:
<221> NAME/KEY: VARIANT
<222> LOCATION: (465)..(467)
<223> OTHER INFORMATION: Xaa = Pro or Ser
<220> FEATURE:
<221> NAME/KEY: VARIANT
<222> LOCATION: (468)..(469)
<223> OTHER INFORMATION: Xaa = Pro or or Thr
<220> FEATURE:
<221> NAME/KEY: VARIANT
<222> LOCATION: (470)..(470)

<223> OTHER INFORMATION: Xaa = Thr or Val
<220> FEATURE:
<221> NAME/KEY: VARIANT
<222> LOCATION: (471)..(471)
<223> OTHER INFORMATION: Xaa = Thr or Pro
<220> FEATURE:
<221> NAME/KEY: VARIANT
<222> LOCATION: (472)..(472)
<223> OTHER INFORMATION: Xaa = Thr or Ser
<220> FEATURE:
<221> NAME/KEY: VARIANT
<222> LOCATION: (475)..(475)
<223> OTHER INFORMATION: Xaa = Ala or Thr
<220> FEATURE:
<221> NAME/KEY: VARIANT
<222> LOCATION: (476)..(476)
<223> OTHER INFORMATION: Xaa = Pro or Thr
<220> FEATURE:
<221> NAME/KEY: VARIANT
<222> LOCATION: (477)..(477)
<223> OTHER INFORMATION: Xaa = Ala or Ser
<220> FEATURE:
<221> NAME/KEY: VARIANT
<222> LOCATION: (478)..(478)
<223> OTHER INFORMATION: Xaa = Thr or Ser
<220> FEATURE:
<221> NAME/KEY: VARIANT
<222> LOCATION: (479)..(479)
<223> OTHER INFORMATION: Xaa = Thr or Gly
<220> FEATURE:
<221> NAME/KEY: VARIANT
<222> LOCATION: (480)..(481)
<223> OTHER INFORMATION: Xaa = Thr or Ser
<220> FEATURE:
<221> NAME/KEY: VARIANT
<222> LOCATION: (482)..(482)
<223> OTHER INFORMATION: Xaa = Ala or Gly
<220> FEATURE:
<221> NAME/KEY: VARIANT
<222> LOCATION: (483)..(483)
<223> OTHER INFORMATION: Xaa = Ser or Pro
<220> FEATURE:
<221> NAME/KEY: VARIANT
<222> LOCATION: (484)..(484)
<223> OTHER INFORMATION: Xaa = Ala or Thr
<220> FEATURE:
<221> NAME/KEY: VARIANT
<222> LOCATION: (486)..(486)
<223> OTHER INFORMATION: Xaa = Pro or Gly
<220> FEATURE:
<221> NAME/KEY: VARIANT
<222> LOCATION: (487)..(487)
<223> OTHER INFORMATION: Xaa = Lys or Thr
<220> FEATURE:
<221> NAME/KEY: VARIANT
<222> LOCATION: (488)..(488)
<223> OTHER INFORMATION: Xaa = Gly or absent
<220> FEATURE:
<221> NAME/KEY: VARIANT
<222> LOCATION: (489)..(489)
<223> OTHER INFORMATION: Xaa = Val or absent
<220> FEATURE:
<221> NAME/KEY: VARIANT
<222> LOCATION: (491)..(491)
<223> OTHER INFORMATION: Xaa = Gly or Lys
<220> FEATURE:
<221> NAME/KEY: VARIANT
<222> LOCATION: (492)..(492)
<223> OTHER INFORMATION: Xaa = Arg or His
<220> FEATURE:
<221> NAME/KEY: VARIANT
<222> LOCATION: (493)..(493)
<223> OTHER INFORMATION: Xaa = Trp or Tyr
<220> FEATURE:
<221> NAME/KEY: VARIANT
<222> LOCATION: (494)..(494)
<223> OTHER INFORMATION: Xaa = Gln or Glu
<220> FEATURE:
<221> NAME/KEY: VARIANT
<222> LOCATION: (509)..(509)
<223> OTHER INFORMATION: Xaa = Glu or Ser

<400> SEQUENCE: 40

Ala Lys Phe Ala Thr Leu Ala Ala Leu Val Ala Xaa Ala Ala Ala Gln
1 5 10 15

Xaa Ala Cys Xaa Leu Thr Xaa Glu Xaa His Pro Ser Leu Xaa Trp Xaa
20 25 30

Lys Cys Thr Xaa Gly Gly Xaa Cys Xaa Xaa Val Gln Xaa Ser Ile Thr
35 40 45

Xaa Asp Xaa Asn Trp Arg Trp Thr His Xaa Xaa Xaa Xaa Xaa Thr Asn
50 55 60

Cys Tyr Xaa Gly Asn Lys Trp Asp Thr Ser Xaa Cys Xaa Asp Xaa Xaa
65 70 75 80

Ser Cys Ala Xaa Xaa Cys Cys Xaa Asp Gly Ala Asp Tyr Xaa Ser Thr
85 90 95

Tyr Gly Ile Thr Thr Xaa Gly Xaa Ser Leu Xaa Leu Lys Phe Val Thr
100 105 110

Lys Gly Gln Tyr Ser Thr Asn Xaa Gly Ser Arg Thr Tyr Leu Met Xaa
115 120 125

Xaa Xaa Xaa Lys Tyr Gln Xaa Phe Xaa Leu Leu Gly Asn Glu Phe Thr
130 135 140

Phe Asp Val Asp Val Ser Asn Xaa Gly Cys Gly Leu Asn Gly Ala Leu
145 150 155 160

Tyr Phe Val Ser Met Asp Ala Asp Gly Gly Xaa Ser Xaa Tyr Xaa Gly
165 170 175

Asn Lys Ala Gly Ala Lys Tyr Gly Thr Gly Tyr Cys Asp Xaa Gln Cys
180 185 190

Pro Arg Asp Xaa Lys Phe Ile Asn Gly Glu Ala Asn Xaa Glu Xaa Trp
195 200 205

Xaa Xaa Ser Thr Asn Asp Xaa Asn Ala Gly Xaa Gly Xaa Tyr Gly Xaa
210 215 220

Cys Cys Ser Glu Met Asp Xaa Trp Glu Ala Asn Asn Met Ala Xaa Ala
225 230 235 240

Phe Thr Pro His Pro Cys Thr Xaa Ile Gly Gln Ser Arg Cys Glu Gly
245 250 255

Asp Ser Cys Gly Gly Thr Tyr Ser Xaa Xaa Arg Tyr Ala Gly Xaa Cys
260 265 270

Asp Pro Asp Gly Cys Asp Phe Asn Ser Tyr Arg Gln Gly Asn Lys Thr
275 280 285

Phe Tyr Gly Lys Gly Met Thr Val Asp Thr Thr Lys Lys Ile Thr Val
290 295 300

Val Thr Gln Phe Leu Lys Xaa Xaa Xaa Gly Xaa Leu Xaa Glu Ile Lys
305 310 315 320

Arg Phe Tyr Val Gln Xaa Gly Lys Xaa Ile Pro Asn Ser Glu Ser Thr
325 330 335

Ile Pro Gly Val Glu Gly Asn Ser Ile Thr Gln Asp Trp Cys Asp Arg
340 345 350

Gln Lys Xaa Ala Phe Gly Asp Xaa Xaa Asp Phe Xaa Xaa Lys Gly Gly
355 360 365

Met Xaa Gln Met Gly Lys Ala Leu Ala Gly Pro Met Val Leu Val Met
370 375 380

Ser Ile Trp Asp Asp His Ala Xaa Asn Met Leu Trp Leu Asp Ser Thr
385 390 395 400

```
Xaa Pro Xaa Asp Xaa Ala Gly Lys Pro Gly Ala Glu Arg Gly Ala Cys
                405                 410                 415

Pro Thr Thr Ser Gly Val Pro Ala Glu Val Glu Ala Glu Ala Pro Asn
            420                 425                 430

Ser Asn Val Xaa Phe Ser Asn Ile Arg Phe Gly Pro Ile Gly Ser Thr
        435                 440                 445

Val Xaa Gly Leu Pro Xaa Xaa Gly Xaa Gly Xaa Xaa Asn Xaa Xaa Xaa
    450                 455                 460

Xaa Xaa Xaa Xaa Xaa Xaa Xaa Xaa Ser Ser Xaa Xaa Xaa Xaa Xaa Xaa
465                 470                 475                 480

Xaa Xaa Xaa Xaa Gly Xaa Xaa Xaa Xaa Ala Xaa Xaa Xaa Xaa Gln Cys
                485                 490                 495

Gly Gly Ile Gly Phe Thr Gly Pro Thr Gln Cys Glu Xaa Pro Tyr Thr
            500                 505                 510

Cys Thr Lys Leu Asn Asp Trp Tyr Ser Gln Cys Leu
        515                 520
```

<210> SEQ ID NO 41
<211> LENGTH: 524
<212> TYPE: PRT
<213> ORGANISM: Artificial Sequence
<220> FEATURE:
<223> OTHER INFORMATION: Synthetic polypeptide of wild-type thermophilic fungus strain C1 cellobiohydrolase type 1a (CBH1a) pre-protein, 1,4-beta-D-glucan cellobiohydrolase (exoglucanase, cellobiohydrolase, CBH) partial sequence

<400> SEQUENCE: 41

```
Ala Lys Phe Ala Thr Leu Ala Ala Leu Val Ala Gly Ala Ala Ala Gln
1               5                   10                  15

Asn Ala Cys Thr Leu Thr Ala Glu Asn His Pro Ser Leu Thr Trp Ser
            20                  25                  30

Lys Cys Thr Ser Gly Gly Ser Cys Thr Ser Val Gln Gly Ser Ile Thr
        35                  40                  45

Ile Asp Ala Asn Trp Arg Trp Thr His Arg Thr Asp Ser Ala Thr Asn
    50                  55                  60

Cys Tyr Glu Gly Asn Lys Trp Asp Thr Ser Tyr Cys Ser Asp Gly Pro
65                  70                  75                  80

Ser Cys Ala Ser Lys Cys Cys Ile Asp Gly Ala Asp Tyr Ser Ser Thr
                85                  90                  95

Tyr Gly Ile Thr Thr Ser Gly Asn Ser Leu Asn Leu Lys Phe Val Thr
            100                 105                 110

Lys Gly Gln Tyr Ser Thr Asn Ile Gly Ser Arg Thr Tyr Leu Met Glu
        115                 120                 125

Ser Asp Thr Lys Tyr Gln Met Phe Gln Leu Leu Gly Asn Glu Phe Thr
    130                 135                 140

Phe Asp Val Asp Val Ser Asn Leu Gly Cys Gly Leu Asn Gly Ala Leu
145                 150                 155                 160

Tyr Phe Val Ser Met Asp Ala Asp Gly Gly Met Ser Lys Tyr Ser Gly
                165                 170                 175

Asn Lys Ala Gly Ala Lys Tyr Gly Thr Gly Tyr Cys Asp Ser Gln Cys
            180                 185                 190

Pro Arg Asp Leu Lys Phe Ile Asn Gly Glu Ala Asn Val Glu Asn Trp
        195                 200                 205

Gln Ser Ser Thr Asn Asp Ala Asn Ala Gly Thr Gly Lys Tyr Gly Ser
    210                 215                 220
```

-continued

```
Cys Cys Ser Glu Met Asp Val Trp Glu Ala Asn Asn Met Ala Ala Ala
225                 230                 235                 240

Phe Thr Pro His Pro Cys Thr Val Ile Gly Gln Ser Arg Cys Glu Gly
                245                 250                 255

Asp Ser Cys Gly Gly Thr Tyr Ser Thr Asp Arg Tyr Ala Gly Ile Cys
            260                 265                 270

Asp Pro Asp Gly Cys Asp Phe Asn Ser Tyr Arg Gln Gly Asn Lys Thr
        275                 280                 285

Phe Tyr Gly Lys Gly Met Thr Val Asp Thr Thr Lys Lys Ile Thr Val
    290                 295                 300

Val Thr Gln Phe Leu Lys Asn Ser Ala Gly Glu Leu Ser Glu Ile Lys
305                 310                 315                 320

Arg Phe Tyr Val Gln Asn Gly Lys Val Ile Pro Asn Ser Glu Ser Thr
                325                 330                 335

Ile Pro Gly Val Glu Gly Asn Ser Ile Thr Gln Asp Trp Cys Asp Arg
            340                 345                 350

Gln Lys Ala Ala Phe Gly Asp Val Thr Asp Phe Gln Asp Lys Gly Gly
        355                 360                 365

Met Val Gln Met Gly Lys Ala Leu Ala Gly Pro Met Val Leu Val Met
    370                 375                 380

Ser Ile Trp Asp Asp His Ala Val Asn Met Leu Trp Leu Asp Ser Thr
385                 390                 395                 400

Trp Pro Ile Asp Gly Ala Gly Lys Pro Gly Ala Glu Arg Gly Ala Cys
                405                 410                 415

Pro Thr Thr Ser Gly Val Pro Ala Glu Val Glu Ala Glu Ala Pro Asn
            420                 425                 430

Ser Asn Val Ile Phe Ser Asn Ile Arg Phe Gly Pro Ile Gly Ser Thr
        435                 440                 445

Val Ser Gly Leu Pro Asp Gly Gly Ser Gly Asn Pro Asn Pro Pro Val
    450                 455                 460

Ser Ser Ser Thr Pro Val Pro Ser Ser Ser Thr Thr Ser Ser Gly Ser
465                 470                 475                 480

Ser Gly Pro Thr Gly Gly Thr Gly Val Ala Lys His Tyr Glu Gln Cys
                485                 490                 495

Gly Gly Ile Gly Phe Thr Gly Pro Thr Gln Cys Glu Ser Pro Tyr Thr
            500                 505                 510

Cys Thr Lys Leu Asn Asp Trp Tyr Ser Gln Cys Leu
        515                 520


<210> SEQ ID NO 42
<211> LENGTH: 48
<212> TYPE: PRT
<213> ORGANISM: Artificial Sequence
<220> FEATURE:
<223> OTHER INFORMATION: Synthetic polypeptide of wild-type thermophilic
      fungus strain C1 cellobiohydrolase type 1a (CBH1a) pre-protein,
      1,4-beta-D-glucan cellobiohydrolase (exoglucanase,
      cellobiohydrolase, CBH) C-terminus

<400> SEQUENCE: 42

Ser Ser Gly Ser Ser Gly Pro Thr Gly Gly Thr Gly Val Ala Lys His
1               5                   10                  15

Tyr Glu Gln Cys Gly Gly Ile Gly Phe Thr Gly Pro Thr Gln Cys Glu
            20                  25                  30

Ser Pro Tyr Thr Cys Thr Lys Leu Asn Asp Trp Tyr Ser Gln Cys Leu
        35                  40                  45
```

-continued

```
<210> SEQ ID NO 43
<211> LENGTH: 39
<212> TYPE: PRT
<213> ORGANISM: Artificial Sequence
<220> FEATURE:
<223> OTHER INFORMATION: Synthetic polypeptide of CBH1a truncated
      variant C-terminus

<400> SEQUENCE: 43

Ser Ser Gly Ser Ser Gly Pro Thr Gly Gly Thr Gly Val Ala Lys His
1               5                   10                  15

Tyr Glu Gln Cys Gly Gly Ile Gly Phe Thr Gly Pro Thr Gln Cys Glu
            20                  25                  30

Ala Arg Thr Leu Ala Pro Ser
        35
```